(12) United States Patent
Naor et al.

(10) Patent No.: US 7,534,605 B2
(45) Date of Patent: May 19, 2009

(54) CD44 POLYPEPTIDES, POLYNUCLEOTIDES ENCODING SAME, ANTIBODIES DIRECTED THEREAGAINST AND METHOD OF USING SAME FOR DIAGNOSING AND TREATING INFLAMMATORY DISEASES

(75) Inventors: David Naor, Jerusalem (IL); Shlomo Nedvetzki, Jerusalem (IL); Itshak Golan, Ashdod (IL); Irina Kessel, Maoz-Zion (IL); Lora Melnik, Rishon le Zion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 18 days.

(21) Appl. No.: 11/130,206

(22) Filed: May 17, 2005

(65) Prior Publication Data

US 2006/0019340 A1 Jan. 26, 2006

Related U.S. Application Data

(63) Continuation-in-part of application No. PCT/IL2004/000639, filed on Jul. 15, 2004, application No. 11/130,206, which is a continuation-in-part of application No. 10/012,969, filed on Dec. 7, 2001, now abandoned, which is a continuation-in-part of application No. PCT/IL00/00326, filed on Jun. 7, 2000.

(60) Provisional application No. 60/495,876, filed on Aug. 19, 2003, provisional application No. 60/486,919, filed on Jul. 15, 2003.

(30) Foreign Application Priority Data

Jun. 8, 1999 (IL) .................................. 130356
Dec. 21, 1999 (IL) .................................. 133647

(51) Int. Cl.
*C12N 5/20* (2006.01)
*C07K 16/00* (2006.01)
*C07K 16/28* (2006.01)
*A61K 39/395* (2006.01)

(52) U.S. Cl. ................. 435/326; 530/388.2; 530/387.1; 435/810; 435/975; 424/143.1

(58) Field of Classification Search ........................ None
See application file for complete search history.

(56) References Cited

U.S. PATENT DOCUMENTS

| | | | |
|---|---|---|---|
| 3,687,808 A | 8/1972 | Merigan et al. |
| 3,791,932 A | 2/1974 | Schuurs et al. |
| 3,839,153 A | 10/1974 | Schuurs et al. |
| 3,850,578 A | 11/1974 | McConnell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,036,945 A | 7/1977 | Haber |
| 4,098,876 A | 7/1978 | Piasio et al. |
| 4,331,647 A | 5/1982 | Goldenberg |
| 4,469,863 A | 9/1984 | Ts'o et al. |
| 4,476,301 A | 10/1984 | Imbach et al. |
| 4,666,828 A | 5/1987 | Gusella |
| 4,683,202 A | 7/1987 | Mullis |
| 4,801,531 A | 1/1989 | Frossard |
| 4,816,567 A | 3/1989 | Cabilly et al. |
| 4,879,219 A | 11/1989 | Wands et al. |
| H000735 H | 2/1990 | Srivastava et al. |
| 4,946,778 A | 8/1990 | Ladner et al. |
| 5,011,771 A | 4/1991 | Bellet et al. |
| 5,023,243 A | 6/1991 | Tullis |
| 5,034,506 A | 7/1991 | Summerton et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |

(Continued)

FOREIGN PATENT DOCUMENTS

EP 0239400 9/1987

(Continued)

OTHER PUBLICATIONS

Rudikoff et al Single amino acid substitution altering antigen-binding specificity. Proc Natl Acad Sci U S A. Mar. 1982;79(6):1979-83.*
Owens RJ, Young RJ. The genetic engineering of monoclonal antibodies. J Immunol Methods. 168(2):149-165, 1994.*
Naor and Nedvetzki. CD44 in rheumatoid arthritis. Arthritis Res Ther. 5:105-115, 2003.*
Naor and Golan. Generation of anti-aCD44-rheumatoid arthrits-specific monoclonal antibodies. Human Antibodies 13:13-14, 2004.*
Colman PM. Effects of amino acid sequence changes on antibody-antigen interactions. Res Immunol. 145(1):33-36, 1994.*
Abaza MS, Atassi MZ. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44.*

(Continued)

*Primary Examiner*—Maher M. Haddad

(57) ABSTRACT

An isolated polypeptide is provided. The isolated polypeptide comprising an antigen recognition domain capable of specifically binding a CD44 polypeptide as set forth in SEQ ID NO: 2 and incapable of binding a CD44 polypeptide selected from the group consisting of: SEQ ID NO: 4 or 6.

11 Claims, 30 Drawing Sheets
(19 of 30 Drawing Sheet(s) Filed in Color)

U.S. PATENT DOCUMENTS

| | | | |
|---|---|---|---|
| 5,264,423 | A | 11/1993 | Cohen et al. |
| 5,264,562 | A | 11/1993 | Matteucci |
| 5,264,564 | A | 11/1993 | Matteucci et al. |
| 5,272,057 | A | 12/1993 | Smulson et al. |
| 5,276,019 | A | 1/1994 | Cohen et al. |
| 5,278,302 | A | 1/1994 | Caruthers et al. |
| 5,281,521 | A | 1/1994 | Trojanowski et al. |
| 5,286,717 | A | 2/1994 | Cohen et al. |
| 5,321,131 | A | 6/1994 | Agrawal et al. |
| 5,399,676 | A | 3/1995 | Froehler |
| 5,405,938 | A | 4/1995 | Summerton et al. |
| 5,405,939 | A | 4/1995 | Suhadolnik et al. |
| 5,434,257 | A | 7/1995 | Matteucci et al. |
| 5,453,496 | A | 9/1995 | Caruthers et al. |
| 5,455,233 | A | 10/1995 | Spielvogel et al. |
| 5,466,677 | A | 11/1995 | Baxter et al. |
| 5,470,967 | A | 11/1995 | Huie et al. |
| 5,476,925 | A | 12/1995 | Letsinger et al. |
| 5,489,677 | A | 2/1996 | Sanghvi et al. |
| 5,519,126 | A | 5/1996 | Hecht |
| 5,536,821 | A | 7/1996 | Agrawal et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,545,806 | A | 8/1996 | Lonberg et al. |
| 5,545,807 | A | 8/1996 | Surani et al. |
| 5,550,111 | A | 8/1996 | Suhadolnik et al. |
| 5,561,225 | A | 10/1996 | Maddry et al. |
| 5,563,253 | A | 10/1996 | Agrawal et al. |
| 5,569,825 | A | 10/1996 | Lonberg et al. |
| 5,571,799 | A | 11/1996 | Tkachuk et al. |
| 5,587,361 | A | 12/1996 | Cook et al. |
| 5,596,086 | A | 1/1997 | Matteucci et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,625,126 | A | 4/1997 | Lonberg et al. |
| 5,633,360 | A | 5/1997 | Bischofberger et al. |
| 5,633,425 | A | 5/1997 | Lonberg et al. |
| 5,661,016 | A | 8/1997 | Lonberg et al. |
| 5,663,312 | A | 9/1997 | Chaturvedula |
| 5,677,437 | A | 10/1997 | Teng et al. |
| 5,677,439 | A | 10/1997 | Weis et al. |
| 5,714,331 | A | 2/1998 | Buchardt et al. |
| 5,719,262 | A | 2/1998 | Buchardt et al. |
| 5,843,449 | A | 12/1998 | Boots et al. |
| 5,935,577 | A | 8/1999 | Weiner et al. |
| 5,951,982 | A | 9/1999 | Zöller |
| 5,961,977 | A | 10/1999 | Hafler et al. |
| 6,010,865 | A | 1/2000 | Ponta et al. |
| 6,019,970 | A | 2/2000 | Ghent et al. |
| 6,077,509 | A | 6/2000 | Weiner et al. |
| 6,303,374 | B1 | 10/2001 | Zhang et al. |
| 6,645,504 | B1 | 11/2003 | Weiner et al. |
| 6,703,361 | B2 | 3/2004 | Weiner et al. |
| 6,790,447 | B1 | 9/2004 | Wildner et al. |

FOREIGN PATENT DOCUMENTS

| | | |
|---|---|---|
| EP | 0368684 | 5/1990 |
| EP | 0438310 | 7/1991 |
| EP | 0501233 | 2/1992 |
| EP | 0519596 | 12/1992 |
| EP | 0538754 | 4/1993 |
| WO | WO 92/07075 | 4/1992 |
| WO | WO 92/22653 | 12/1992 |
| WO | WO 94/02610 | 2/1994 |
| WO | WO 94/09811 | 5/1994 |
| WO | WO 95/03832 | 2/1995 |
| WO | WO 95/00658 | 5/1995 |
| WO | WO 00/75312 A1 * | 12/2000 |
| WO | WO 02/078524 | 10/2002 |
| WO | WO 03/014160 | 2/2003 |
| WO | WO 03/072606 | 4/2003 |
| WO | WO 2005/007700 | 1/2005 |

OTHER PUBLICATIONS

Zheng et al. Monoclonal antibodies to CD44 and their influence on hyaluronan recognition. J Cell Biol. 130(2):485-495, 1995.*

Nedvetzki et al. "A Mutation in A CD44 Variant of Inflammatory Cells Enhances the Mitogenic Interaction of FGF With Its Receptor", Journal of Clinical Investigation, 111(8): 1211-1220, 2003. Abstract, p. 1212, col. 1, § 2, p. 1214, col. 1, § 3—col. 2, § 1., p. 1218, col. 2, § 2, p. 1219, col. 2, § 4.

Kugelman et al. "The Core Protein of Epican, A Heparan Sulfate Proteoglycan on Keratinocytes, Is An Alternative Form of CD44", Journal of Investigative Dermatology, 99(4): 381-385, 1992.

Naor et al. "CD44: Structure, Function and Association With the Malignant Process", Advances in Cancer Research, 71: 241-319, 1997. p. 286, last §—p. 287, first §.

Martegani et al. "Structural Variability of CD44v Molecules and Reliability of Immunodetection of CD44 Isoforms Using mAbs Specific for DC44 Variant Exon Products", American Journal of Pathology, 154(1): 291-300, 1999.

Harlow et al. "Antibodies", A Laboratory Manuel, Cold Spring Harbor, p. 141-155, 1988.

Ngo et al. "Computational Complexity, Protein Structure Prediction and the Levinthal Paradox", The Protein Folding Problem, Problem and Tertiary Structure Prediction, Chap. 14: 491-494, 1994.

Li et al. "β-Endorphin Omission Analogs: Dissociation of Immunoreactivity From Other Biological Activities", Proc. Natl. Acad. Sci. USA, 77(6): 3211-3114, 1980.

Koopman et al. "Activated Human Lymphocytes and Aggressive Non-Hodgkin's Lymphomas Express A Homologue of the Rat Metastasis-Associated Variant of CD44", Journal of Experimental Medicine, 177: 897-904, 1993. Abstract.

Screaton et al. "Genomic Structure of DNA Encoding the Lymphocyte Homing Receptor CD44 Reveals at Least 12 Alternatively Spliced Exons", Proc. Natl. Acad. Sci. USA, 89: 12160-12164, 1992. Abstract.

Verdrengh et al. "Administration of Antibodies to Hyaluronanreceptor (CD44) Delays the Start and Ameliorates the Severiy of Collagen II Arthritis", Scandivanian Journal of Immunology, 42: 353-358, 1995. Introduction.

Alexander et al. "Autoimmune Prostatitis: Evidence of T Cell Reactivity With Normal Prostate Proteins", Urology, 50:893-899, 1997.

Antoine et al. "Anti-Neuronal Antibodies and Central Nervous System Diseases: Contribution to Diagnosis and Pathophysiology", Reviews in Neurology, 156(1): 23-33, 2000.

Antoneli et al. "Extraocular Retinoblastoma: A 13-Year Experience", Cancer, 98: 1292-1298, 2003.

Barbas, III et al. "Human Monoclonnal Fab Fragments Derived From A Combinatorial Library Bind to Respiratory Syncytial Virus F Glycoprotein and Neutralize Infectivity", Proc. Natl. Acad. Sci. USA, 89: 10164-10168, 1992.

Bebbington et al. "High-Level Expression of A Recombinant Antibody From Myeloma Cells Using A Glutamine Synthetase Gene as An Amplifiable Selectable Marker", Bio/Technology, 10:169-175, 1992.

Beerli et al. "Intracellular Expression of Single Chain Antibodies Reverts ErbB-2 Transformation", The Journal of Biological Chemistry, 269(39): 23931-23936, 1994.

Biocca et al. "Intracellular Immunization With Cytosolic Recombinant Antibodies", Bio/Technology, 12: 396-399, 1994.

Bird et al. "Single-Chain Antigen-Binding Proteins", Science, 242(4877):423-426, 1988.

Boerner et al. "Production of Antigen-Specific Human Monoclonal Antibodies From In Vitro-Primed Human Splenocytes", The Journal of Immunology, 147(1): 86-95, 1991.

Braley-Mullen et al. "Early Requirement for B Cells for Development of Spntaneous Autoimmune Thyroiditis in NOD.H-2h4 Mice", The Journal of Immunology 165: 7262-7269, 2000.

Caprossi et al. "Autoimmune T-Cell Response to the CD4 Molecule in HIV-Infected Patients", Viral Immunology, 11(1): 9-17, 1998.

Carlson "A New Use for Intracellular Antibody Expression: Inactivation of Human Immunodeficiency Virus Type 1", Proc. Natl. Acad. Sci. USA, 90: 7427-7428, 1993.

Castano et al. "Type-I Diabetes: A Chronic Autoimmune Disease of Human, Mouse, and Rat", Annual Reviews in Immunology, 8: 647-679, 1990.

Chan et al. "The Central and Multiple Roles of B Cells in Lupus Pathogenesis", Immunological REviews, 169: 107-121, 1999.

Chaudhary et al. "A Recombinant Single-Chain Immunotoxin Composed of Anti-Tac Variable Regions and A Truncated Diphtheria Toxin", Proc. natl. Acad. Sci. USA, 87, 9491-9494, 1990.

Chen et al. "Combined Intra- and Extracellular Immunization Against Human Immunodeficiency Virus Type 1 Infection With A Human Anti-Gp120 Antibody", Proc. Natl. Acad. Sci. USA, 91:5932-5936, 1994.

Chen et al. "Intracellular Antibodies as A New Class of Therapeutic Molecules for Gene Therapy", Human Gene Therapy, 5: 595-601, 1994.

Cole et al. "Human Monoclonal Antibodies", Molecular and Cellular Biochemistry, 62: 109-120, 1984.

Cole et al. "The EBV-Hybridoma Technique and Its Application to Human Lung Cancer", Monclonal Antobodies and Cancer Therapy, pp. 77-96, 1985.

Coloma et al. "Novel Vectors for the Expression of Antibody Molecules Using Variable Regions Generated by Polymerase Chain Reaction", Journal of Immunological Methods, 152: 89-104, 1992.

Cross et al. "B Cells and Antibodies in CNS Demyelinating Disease", Journal of Neuroimmunology, 112: 1-14, 2001.

Cunha-Neto et. "Autoimmunity in Chagas' Disease", Journal of Clinical Investigation, 98: 1709-1712, 1996.

Datta "Production of Pathogeni Antibodies: Cognate Interactions Between Autoimmune T and B CElls", Lupus, 7: 591-596, 1998.

Deshane et al. "Intracellular Single-Chain Antibosy Against ErbB2 Down-Regulates Cell Surface ErbB2 and Exhibits A Selective Anti-Proliferative Effect in ErbB2 Overexpressing Cancer Cell Lines", Gene Therapy, 1: 332-337, 1994.

Diekman et al. "Anti-Sperm Antibodies From Infertile Patients and Their Cognate Sperm Antigens: A Review. Identify Between SAGA-1, the H6-3C4 Antigen, and CD52", American Journal of Reproductive Immunology, 43: 134-143, 2000.

Duan et al. "Potent Inhibition of Human Immunodeficiency Virus Type 1 Replication by An Intracellular Anti-Rev Single-Chain Antibody", Proc. Natl. Acad. Sci. USA, 91: 5075-5079, 1994.

Efremov et al. "The Pathologic Significance of the Immunoglobulins Expressed by Chronic Lymphcytic Leukemia B-Cells in the Development of Autoimmune Hemolytic Anemia", Leukemia and Lymphoma, 28: 285-293, 1998.

Englisch et al. "Chemically Modified Oligonucleotides as Probes and Inhibitors", Angewandte Chemie, International Edition in English, 30(6): 613-722, 1991.

Erikson et al. "Self-Reactive B Cells in Nonautoimmune and Autoimmune Mice", Immunologic Research, 17(1 & 2): 49-61, 1998.

Erlich et al. "Specific DNA Amplification", Nature, 331: 461-462, 1998.

Feist et al. "Diagnostic Importance of Anti-Proteasome Antibodies", International Archives of Allergy and Immunology, 123: 92-97, 2000.

Fingl et al. "General Principles", The Pharmacological Basis of Therapeutics, Ch.1(Sec.I): 1-46, 1975.

Fishwild et al. "High-Avidity Human IgGk Monoclonal Antibodies From A Novel Strain of Minilocus TRansgenic Mice", Nature Biotechnology, 14: 845-851, 1996.

Flamholz et al. "Therapeutic Plasma Exchange for the Acute Management of the Catastrophic Antiphospholipid Syndrome: Beta2-Flycoprotein I Antibodies as A Marker of Response to Therapy", Journal of Clinical Apheresis, 14: 171-176, 1999.

Franco et al. "Liver-Derived T Cell Clones in Autoimmune Chronic Active Hepatitis: Accessory Cell function of Hepatocytes Expressing Class II Major Histocompatibility Complex Molecules", Clinical Immunology and Immunopathology, 54: 382-394, 1990.

Friedman et al. "BR96 sFv-PE40, A Potent Single-Chain Immunotoxin That Selectively Kills Carcinoma Cells", Cancer Research, 53: 334-339, 1993.

Gait "Oligoribonucleotides", Antisense Research and Applications, CRC Press, Chap.16: 289-302, 1993.

Garza et al. "Mechanism of Ovarian Autoimmunity: Induction of T Cell and Antibody Responese by T Cell Epitope Mimicry and Epitope Spreading", Journal of Reproductive Immunology, 37: 87-101, 1998.

Gloddek et al. "Induction of An Inner-Ear-Specific Autoreactive T-Cell Line for the Diagnostic Evaluation of An Autoimmune Disease of the Inner Ear", Annals NY Academy of Sciences, 830: 266-276, 1997.

Goodwin "A New Approach to the Problem of Targeting Specific Monoclonal Antibodies to Human Tumors Using Anti-Hapten Chimeric Antobodies", Nuclear Medical Biology, 16(6): 645-651, 1989.

Gussow et al. "Humanization of Monoclonal Antibodies", Methods in Enzymology, 203: 99-121, 1991.

Hara et al. "GammaDelta T Lymphcyte Clonality in Pure Red Blood Cell Aplasia. Response", Blood, 77(5): 1127, 1991.

Hiemstra et al. "Cytomegalovirus in Autoimmunity: T Cell Crossreactivity to Viral antigen and Autoantigen Glutamic Acid Decarboxylase", Proc. Natl. Acad. Sci. USA, 98(7): 3988-3991, 2001.

Hoogenboom et al. "By-Passing Immunisation. Human Antibodies From Synthetic Repertoires of Germline VH Gene Segments Rearranged In Vitro", Journal of Molecular Biology, 227: 381-388, 1992.

Hulme et al. "Strategy and Tactics in Receptor-Binding Studies", Chap.4: 63-119, 124-167, 172-176. 1972

Inbar et al. "Localization of Antibody-Combining Sites Within the Variable Portions of Heavy and LIght Chains", Proc. Natl. Acad. Sci. USA, 69(9): 2659-2662, 1972.

Infante et al. "Myasthenia Gravis and Its Animal Model: T Cell Receptor Expression in An Antibody Mediated Autoimmune Disease", International Review in Immunology, 18: 83-109, 1999.

Jones "T-Cell Autoimmunity in Primary Biliary Cirrhosis", Clinical Science, 91: 551-558, 1996.

Jones et al. "Replacing the Complementary-Determining Regions in A Human Antibody With Those From A Mouse", Nature, 321: 522-525, 1986.

Kelly "T Cell Regulation of Autoimmune Interstitial Nephritis", Journal of the American Society of Nephrology, 1(2): 140-149, 1990.

Koehler et al. "Continuous Cultures of Fused Cells Secreting Antibody of Predefined Specificity", Nature, 256: 495-497, 1975.

Komminoth et al. "Correpondance to the Editor-in-Chief", AJP, 145(3): 742-744, 1994.

Komminoth et al. "Evaluation of Methods for Hepatitis C Virus Detection in Archival Liver Biopsies", Pathology Research Practice, 190: 1017-1025, 1994.

Kornberg "Anti-GM1 Ganglioside Antibodies: Their Role int he Diagnosis and Pathogenesis of Immune-Mediated Motor Neuropathies", Journal of Clinical Neuroscience, 7(3): 191-194, 2000.

Krenn et al. "Histopathology and Molecular Pathology of Synovial B-Lymphocytes in Rheumatoid Arthritis", Histology and Histopathology, 15: 791-798, 2000.

Kusunoki "Antiglycolipid Antibodies in Guillai-Barre Syndrome and Autoimmune Neuropathies", The American Journal of Medical Science, 319(4): 234-239, 2000.

Lacroix-Desmazes et al. "Natural Antibodies to Factor VIII", Seminars in Thrombosis and Hemostasis, 26(2): 157-165, 2000.

Larrick et al. "PCR Amplification of Antibody Genes", Methods: A Companion to Methods in Enzymology, 2(2): 106-110, 1991.

Lonberg et al. "Antigen-Specific Human Antibodies From Mice Comprising Four Distinct Genetic Modifications", Natyre, 368: 856-859, 1994.

Lonberg et al. "Human Antibodies from Transgenic Mice", International Review in Immunology, 13: 65-93, 1995.

Maloney et al. "Monoclonal Anti-Idiotype Antibodies Against the Murine B Cell Lymphoma 38C13: Characterization and Use as Probes for the Biology of the Tumor In Vivo and In Vitro", Hybridoma, 4(3): 191-209, 1985.

Mann "Antibodies to Soluble LIver Antigen: Specific Marker of Autoimmune Hepatitis", Journal of Hepatology, 33: 326-328, 2000.

Marasco et al. "Intracellular Antibodies Against HIV-1 Envelope Protein for AIDS Gene Therapy", HUman Gene THerapy, 9: 1627-1642, 1998.

Marks et al. "By-Passing Immunization. Human Antibodies from V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1982.

Matsuura et al. "Antiphospholipid Antibodies and Atherosclerosis", Lupus, 7(Suppl.2): S135-S139, 1998.

Mhashilkar et al. "Inhibition of HIV-1 Tat-Mediated LTR Transactivation and HIV-1 Infection by Anti-Tat Single Chain Intrabodies", The EMBO Journal, 14(7): 1542-1551, 1995.

Moccia "Two Cases of Autoimmune Thrombocytopenic Purpura Associated With Antiphospholipid Antibodies", Annali Italiani di Medicina Interna, 14(2): 114-117, 1999.

Morrison "Success in Specification", Nature, 368: 812-813, 1994.

Morrison "Transfectomas Provide Novel Chimeric Antibodies", Science, 229(4719): 1202-1207, 1985.

Mullis et al. "Specific Synthesis of DNA In Vitro Via A Polymerase-Catalyzed Chain Reaction", Methods in Enzymology, 155(Chap.21): 335-350, 1987.

Nagaoki et al. "Anti-Thyroglobulin Antibodies", Nippon Rinsho, 57(8): 122-126, 1999.

Nesbit et al. "Production of A Functional Monoclonal Antibody Recognizing Human Colorectal Carcinoma Cells from A Baculovirus Expression System", Journal of Immunological Methods, 151: 201-208, 1992.

Neuberger "Generating High-Avidity Human Mabs in Mice", Nature Biotechnology, 14: 826-827, 1996.

Nissim et al. "Antibody Fragments from A 'Single Plot' Phage Display Library as Immunochemical Reagents", THe EMBO Journal, 13(3): 692-698, 1994.

Nobile-Orazio et al. "Diagnostic Relevance of Anti-Neural Antibodies in Dysimmune Neuropathies", Electroencephalograpy & Clinical Neurophysiology: from Receptors to Perception, EEG, Suppl.50: 419-427, 1999.

Noel "Les Auto-Anticorps 'Anti-Cytoplasme des Polynucleaires' (ANCA): Description et Role Immunopatholoqique", Annales de la Medicine Interne, 151(3): 178-183, 2000.

Nuovo et al. "Intracellular Localization of Polymerase Chain Reaction (PCR)-Amplified Hepatitis C cDNA", The American Journal of Surgical Pathology, 17(7): 683-690, 1993.

Orgiazzi "Anti-TSH Receptor Antibodies in Clinical Practice", Endocrinology and Metabolism Clinics of North America, 29(2): 339-355, 2000.

Oron et al. "Animal Model and In Vitro Studies of Anti Neurofilament Antibodies Mediated Neurogeneration in Alzheimer's Disease", Journal of Neural Transm, Suppl. 49: 77-84, 1997.

Oshima et al. "Autoimmune T Cell Recognition of Human Acetylcholine Receptor: The Sites of T Cell Recognition in Myasthenia Gravis on the Extracellular Part of the Alpha Subunit", European Journal of Immunology, 20: 2563-2569, 1990.

Pack et al. "Imporoved Bivalent Miniantibodies, With Identical Avidity as Whole Antibodies, Produced by High Cell Density Fermentation of Escherichia Coli", Bio/Technology, 11: 1271-1277, 1993.

Porter "The Hydrolysis of Rabbit Gamma-Globulin and Antibodies With Crystalline Papain", Biochemical Journal, 73: 119-126, 1959.

Praprotnik et al. "Pathogenic Role of Anti-Endothelial Cell Antibodies in Systemic Vasculitis", Wiener Klinische Wochenschrift, The Middle European Journal of Medicine, 112(15-16): 660-664, 2000.

Presta "Antibody Engineering", Current Opinion in Structural Biology, 2: 593-596, 1992.

Renaudineau et al. "Anti-Endothelial Cell Antibodies in Systemic Sclerosis", Clinical and Diagnostic Laboratory Immunology, 6(2): 156-160, 1999.

Richardson et al. "Phenotypic Knockout of the High-Affinity Human Interleukin 2 Receptor by Intracellular Single-Chain Antibodies Against the Alpha Subunit of the Receptor", Proc. Natl. Acad. Sci. USA, 92: 3137-3141, 1995.

Riechmann et al. "Reshaping Human Antibodies for Therapy", Nature, 332 323-329, 1988.

Saiki et al. "Enzymatic Amplification of B-Globin Genomic Sequences and Restriction Site Analysis for Diagnosis of Sickle Cell Anemia", Science, 230(4732): 1350-1354, 1985.

Sakata et al. "Autoimmune T-Cell Recognition Sites of Human Thyrotropin Receptor in Graves' Disease", Molecular and Cellular Endocrinology, 92: 77-82, 1993.

Sallah et al. "Gamma/Delta T-Cell Hepatosplenic Lymphoma: Review of the Literature, Diagnosis by Flow Cytometry and Concomitant Autoimmune Hemolytic Anemia", Annals in Hematology, 74: 139-142, 1997.

Sanghvi "Antisense Research and Applications", CRC Press, 276-278, 1993.

Screaton et al. "Genomic Structure of DNA Encoding the Lymphocyte Homing Receptor CD44 Reveals at Least 12 Alternatively Spliced Exons", Proc. Natl. Acad. Sci. USA, 89: 12160-12164, 1992.

Semple et al. "Difference in Serum Cytokine Levels in Acute and Chronic Autoimmune Thrombocytopenic Purpura: Relationship to Platelet Phenotype and Antiplatelet T-Cell Reactivity", Blood, 10: 4245-4254, 1996.

Shaheen et al. "Targeting Human Immunodeficiency Virus Type 1 Reverse Transcriptase by Intracellular Expression of Single-Chain Variable Fragments to Inhibit Early Stages of the Viral Life Cycle", Journal of Virology, 70(6): 3392-3400, 1996.

Shin et al. "Production and Properties of Chimeric Antibody Molecules", Methods in Enzymology, 178: 459-476, 1989.

Soderstrom et al. "Autoimmune T Cell Repertoire in Optic Neuritis and Multiple Sclerosis: T Cells Recognising Multiple Myelin Proteins Are Accumulated in Cerebrospinal Fluid", Journal in Neurological and Neurosurgical Psychiatry, 57: 544-551, 1994.

Strassburg et al. "Anti-Mitochondrial Antibodies and Other Immunological Tests in Primary Biliary Cirrhosis", European Journal of Gastroenterology & Hepatology, 11: 595-601, 1999.

Takamori et al. "Antibodies to Calcium Channel and Synaptotagmin in Lambert-Eaton Myasthenic Syndrome", The American Journal of the Medical Science, 319(4): 204-208, 2000.

Terunori "Idiopathic Myxedema and Blocking Type Antibodies to TSH Receptor", Nippon Rinsho, 57(8): 71-75, 1999.

Tincani et al. "Anti Beta2-Glycoprotein 1 Antibodies: Clinical Significance", Lupus, 7(Suppl.2): S107-S109, 1998.

Tisch et al. "Antigen-Specific Immunotherapy: Is It A Real Possibility to Combat T-Cell-Mediated Autoimmunity?", Proc. Natl. Acad. Sci. USA, 91: 437-438, 1994.

Vaarala "Antiphospholipid Antibodies and Myocardial Infarction", Lupus, 7(Suppl.2): S132-S134, 1998.

Van Regenmortel "Improving the Quality of BIACORE-Based Affinity Measurements", Developments in Biologicals, 112: 141-151, 2003.

Verhoeyen et al. "Reshaping Human Antibodies: Grafting An Antilysozyme Activity", Science, 239(4847): 1534-1536, 1998.

Vincent et al. "Antibodies Affecting Ion Channel Function in Acquired Neurmyotonia, in Seropositive and Seronegative MYasthenia Gravis, and in Antibody-Mediated Arthrogryposis Multiplex Congenita", Annals ot the NY Academy of Sciences, 841: 482-496, 1998.

Voswinkel et al. "B Lymphocyte Involvement in Ankylosing Spondylitis: The Heavy Chain Variable Segment Gene Repertoire of B Lymphocytes from Germinal Center-Like Foci in the Synovial Membrane Indicates Antigen Selection", Arthritis Research, 3: 189-195, 2001.

Wallukat et al. "Agonist-Like Beta-Adrenoceptor Antibodies in Heart Failure", American Journal of Cardiology, 83: 75H-79H, 1999.

Weiner et al. "Binding and Cyrotoxicity Cahracteristics of the Bispecific Murine Monoclonal Antibody 2B1", The Journal of Immunology, 151(5): 2877-2886, 1993.

Werge et al. "Intracellular Immunization. Cloning and Intracellular Expression of A Monoclonal Antibody to the P21Ras Protein", FEBS Letters 274(1,2): 193-198, 1990.

Whitlow et al. "Single-Chain Fv Proteins and Their Fusion Proteins", Methods: A Companian to Methods in Enzymology, 2(2): 97-105, 1991.

Williams et al. "Anti-Tumor Necrosis Factor Ameliorates Joint Disease in Murine Collagen-Induced Arthritis", Proc. Natl. Acad. Sci. USA, 89: 9784-9788, 1992.

Winter et al. "Making Antibodies by Phage Display Technology", Annual Reviews in Immunology, 12: 433-455, 1994.

Yoo et al. "Epitope Especificity and T Cell Receptor Usage in Type II Collagen Induced Autoimmune Ear Disease", Cellular Immunology, 157: 249-262, 1994.

Zauli et al. "Auto-Antibodies in Hepatitis C", Biomedicine & Pharmacotherapy, 53: 234-241, 1999.

Zhang et al. "Membrane Heparan Sulfate Proteoglycan-Supported FGF2-FGFR1 Signaling", The Journal of Biological Chemistry, 276(45): 41921-41929, 2001.

Zimmet "Antibodies to Glutamic Acid Decarboxylase in the Prediction of Insulin Dependency", Diabetes Research and Clinical Practice, 34(Suppl.): S125-S131, 1996.

* cited by examiner

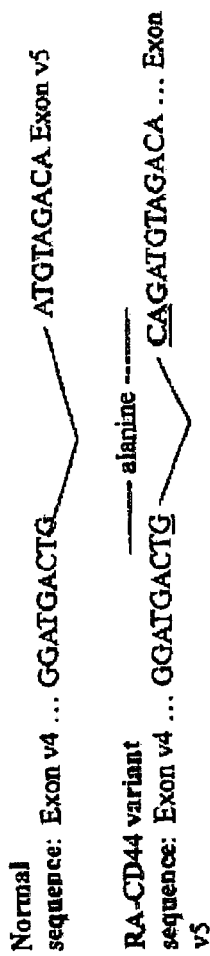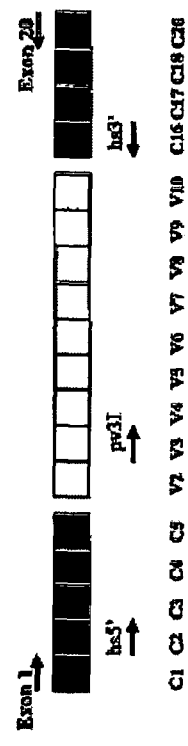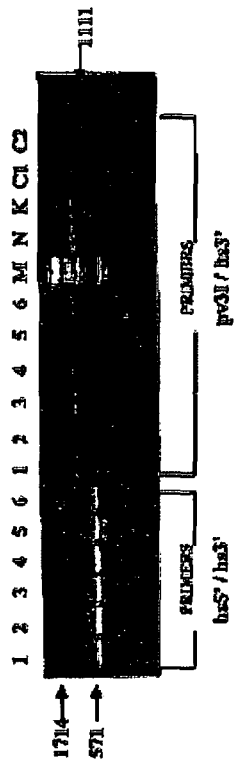

FIG. 1D

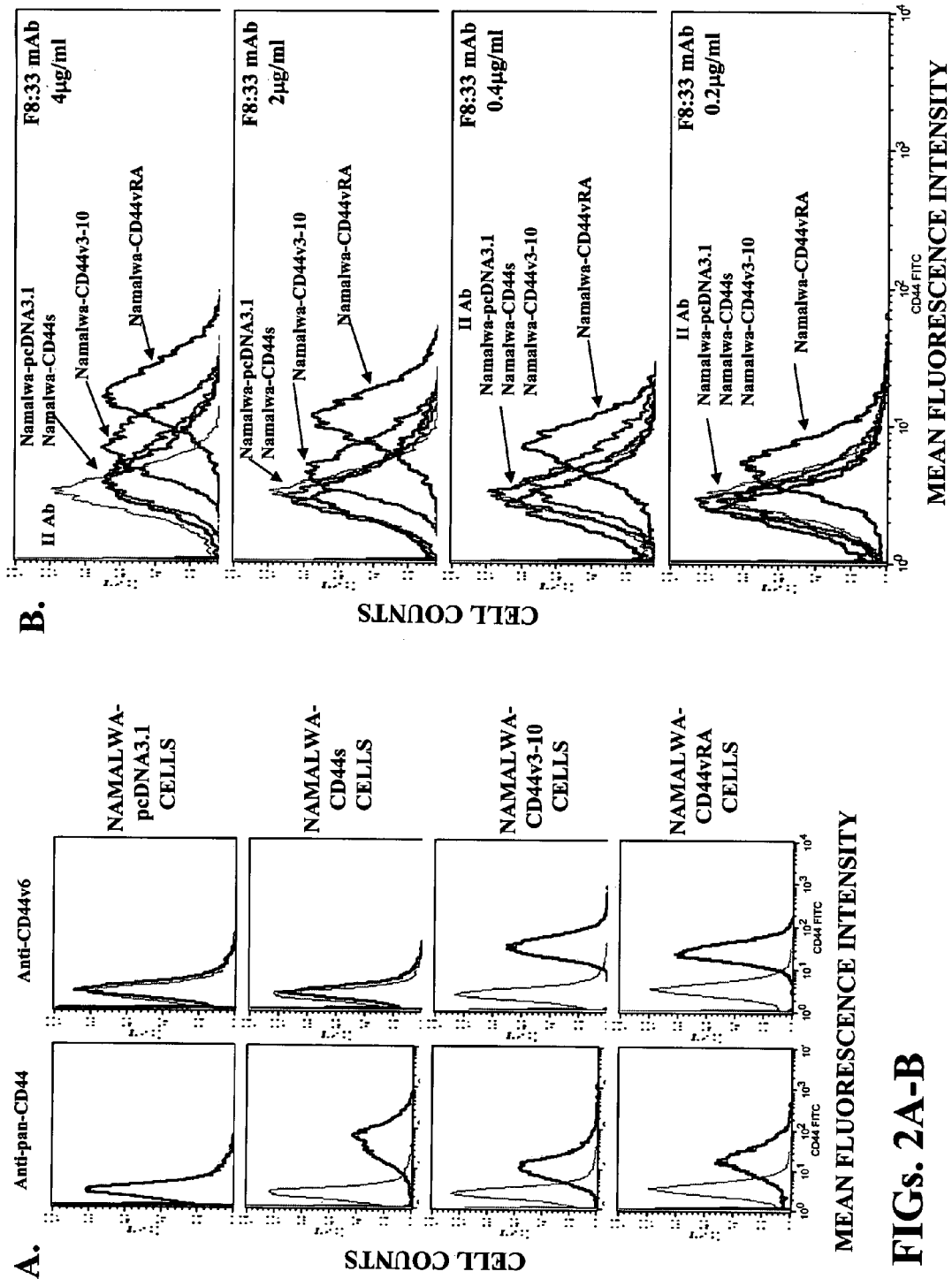
FIGs. 2A-B

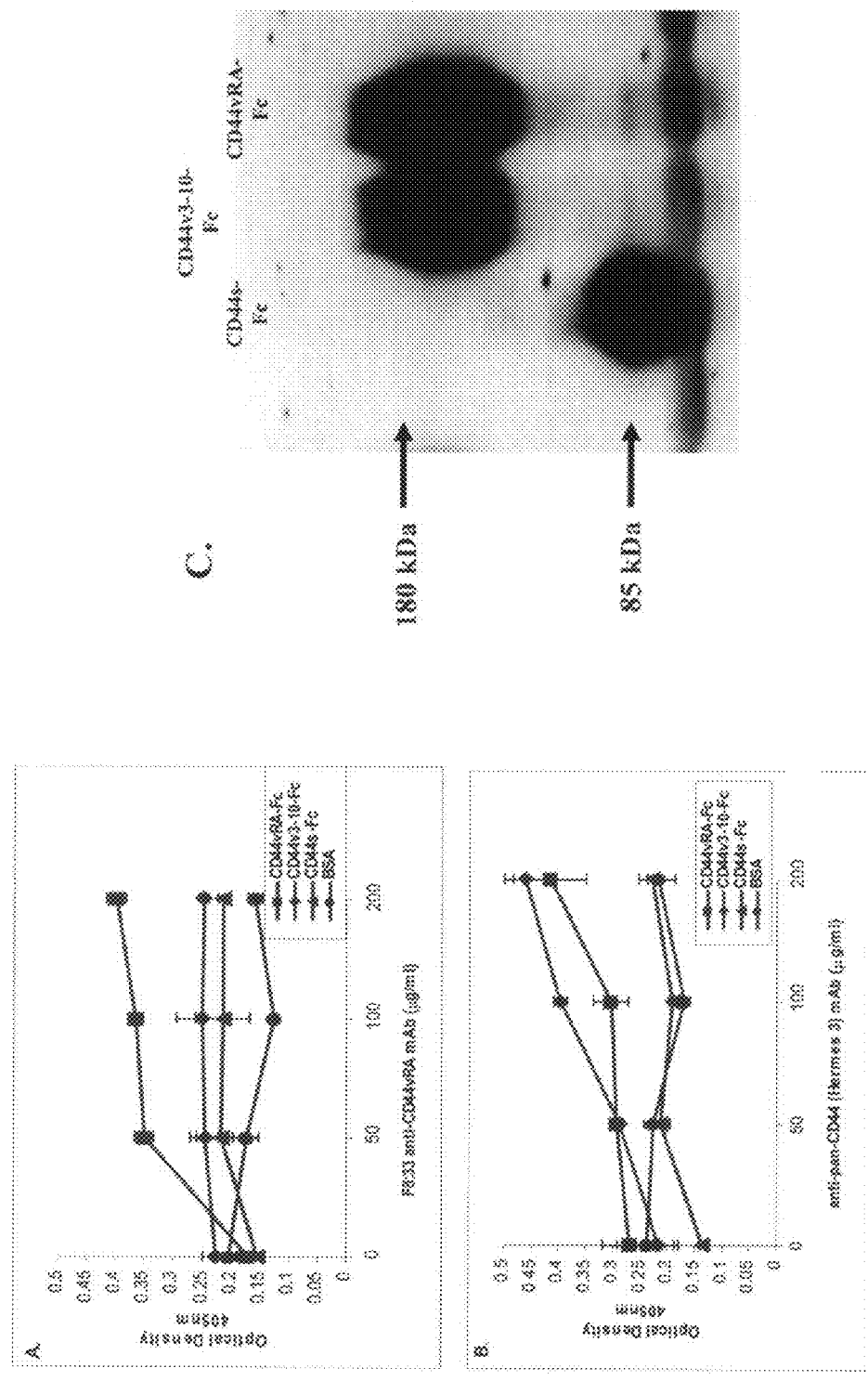
FIGs. 3A-C

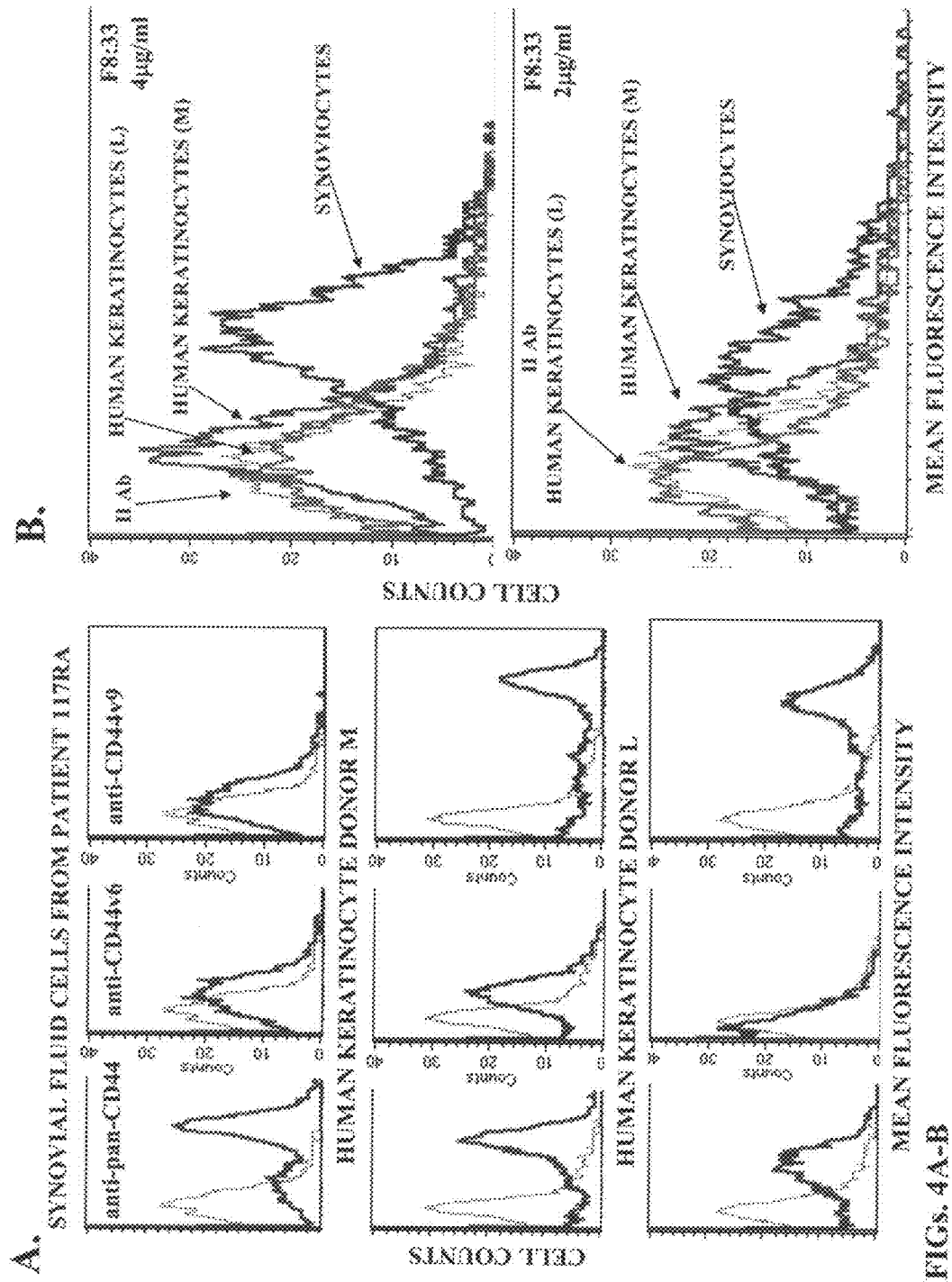
FIGs. 4A-B

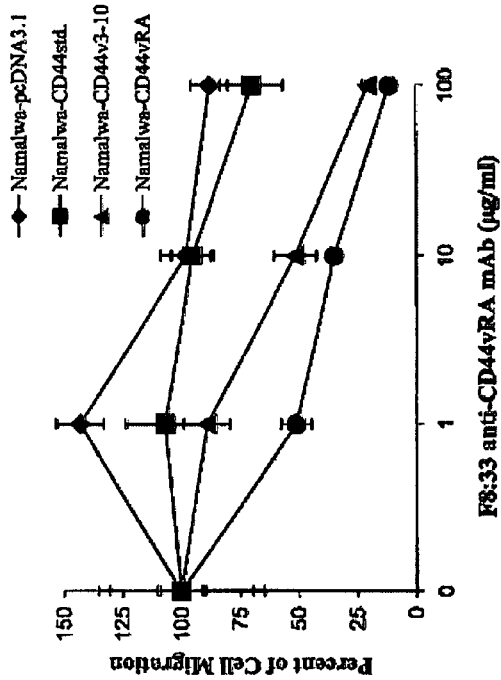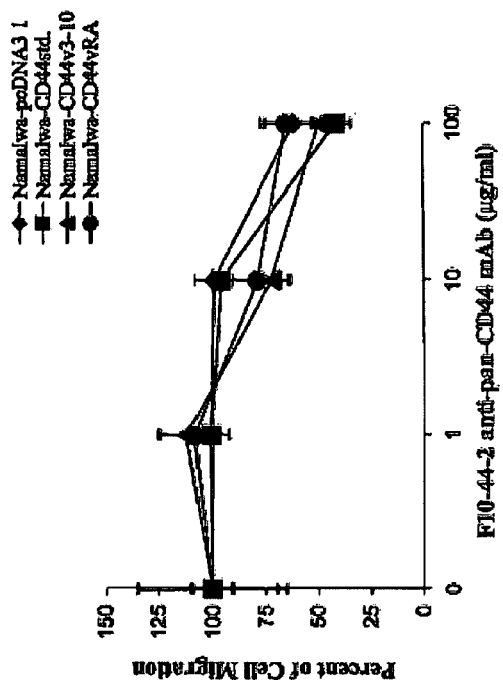
FIG. 5A
FIG. 5B

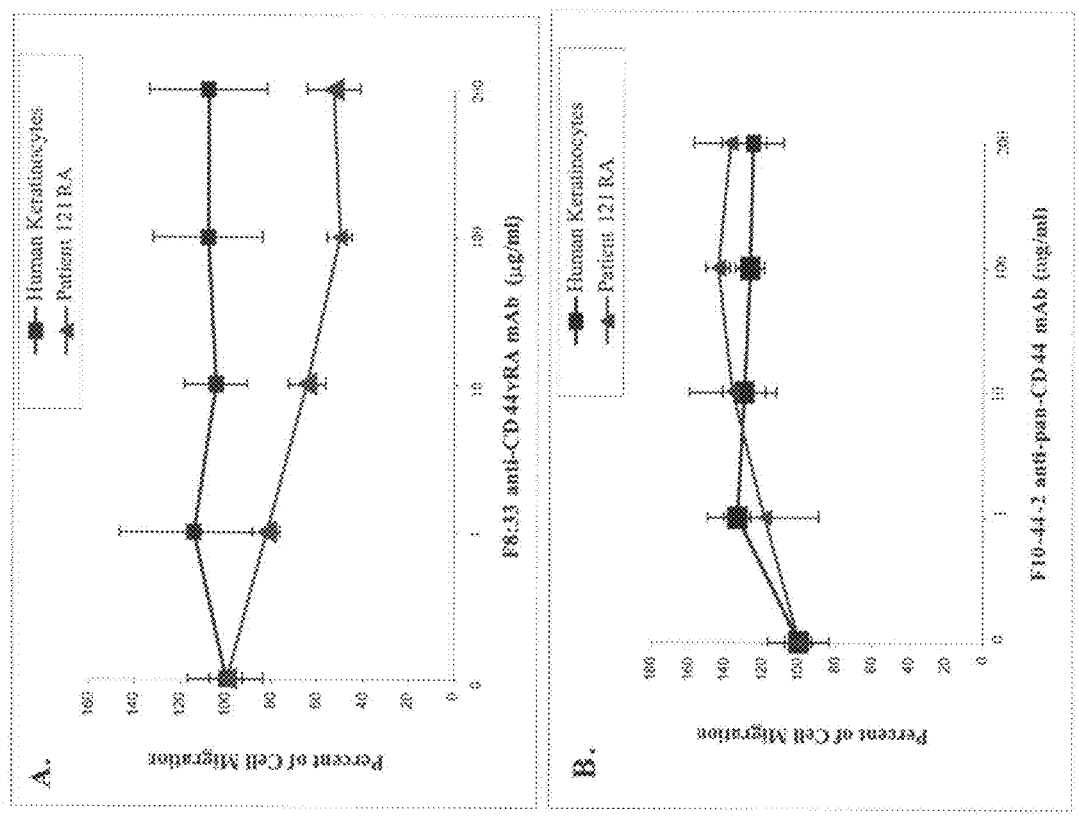
FIGs. 6A-B

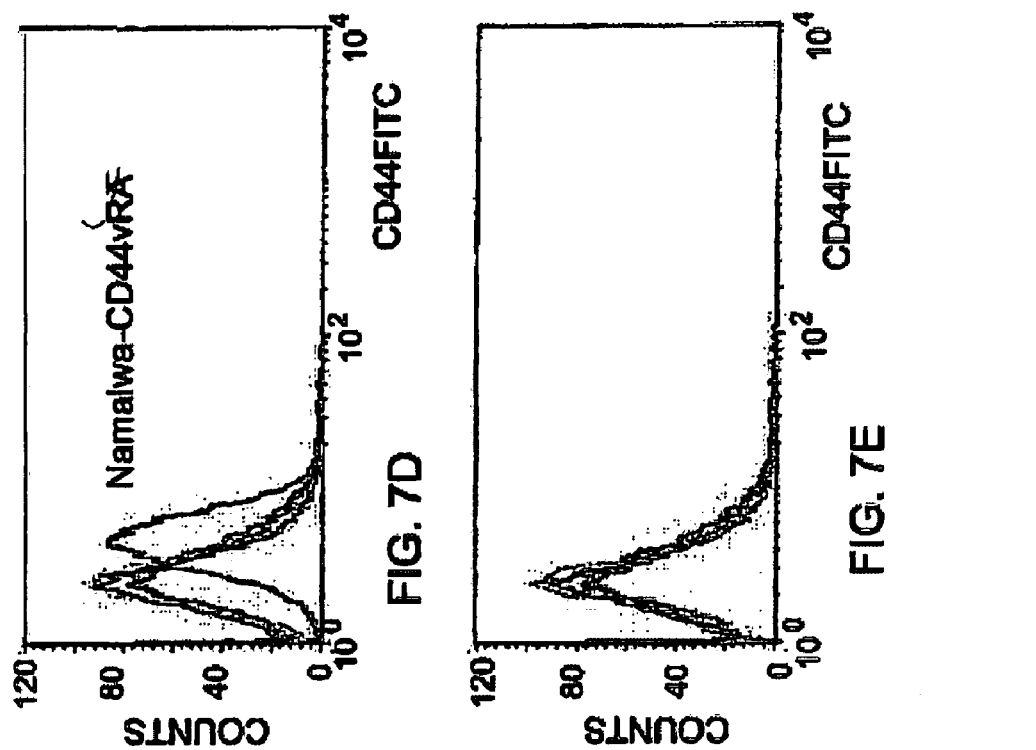
FIG. 7A
FIG. 7B
FIG. 7C
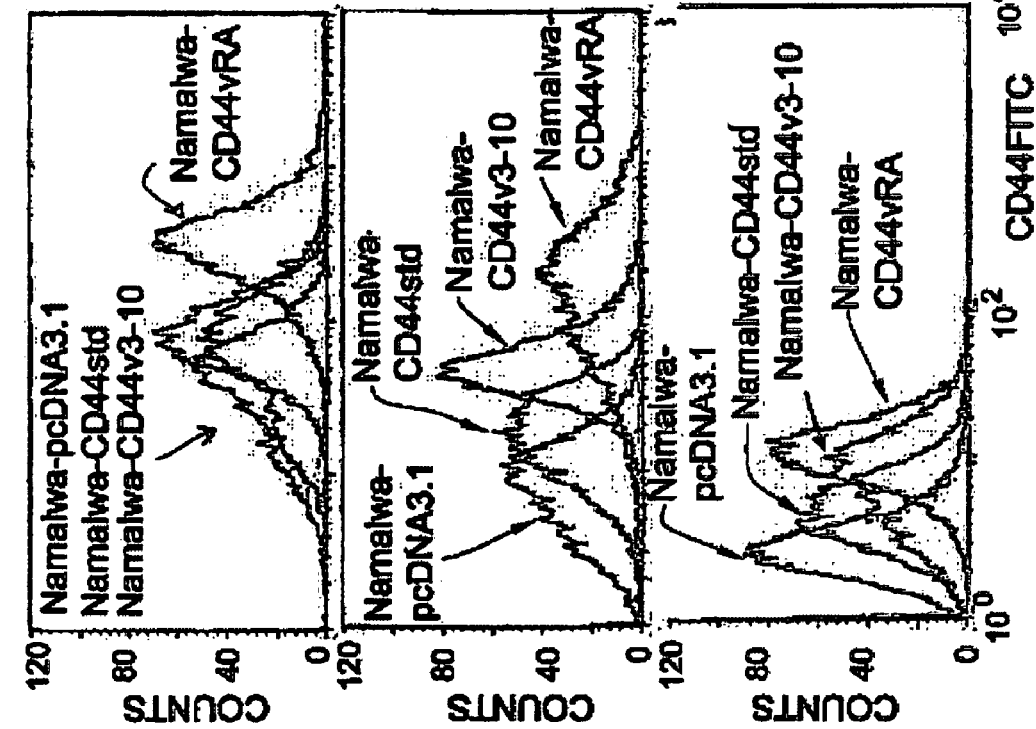
FIG. 7D
FIG. 7E

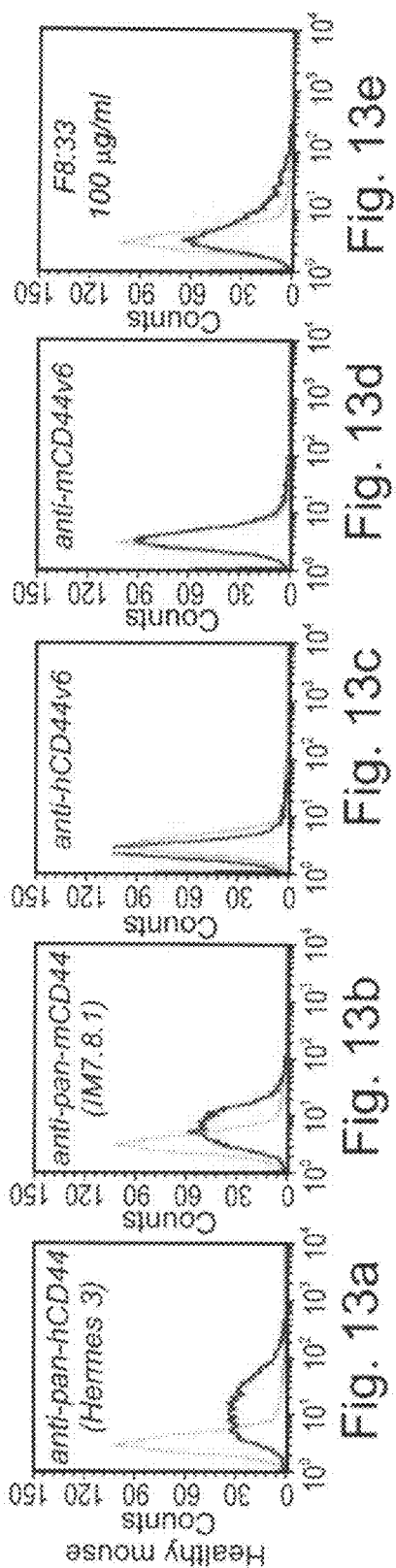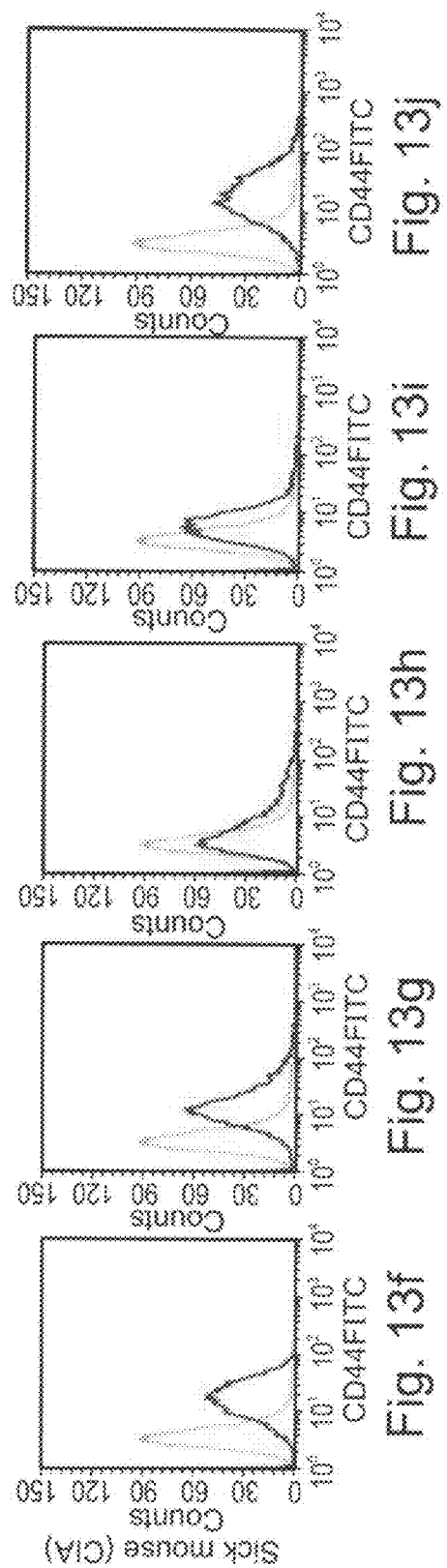

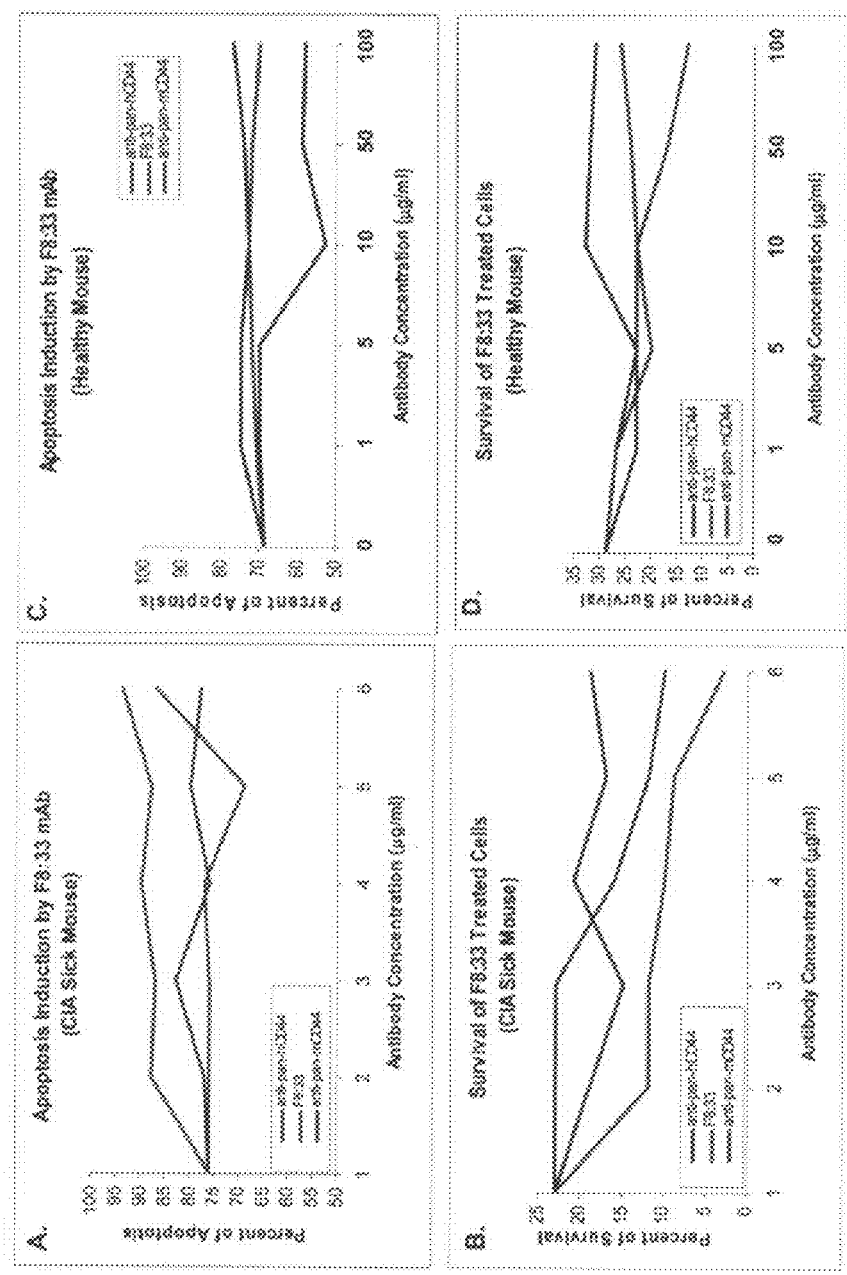
Figures 14A-D

Fig. 18A

```
  1  GTCGGCTTAG GTGAAACTGC AGCAGTCAGG CCTGGCCTGG
 41  TGGGCCCCTC ACAGAGCCTG TCCATCAGTT GCACTGTCTC
 81  TGGGTTTCA TTAACCAGCT ATGGTGTTGA CTGGGTTCGC
121  CAGCCTCCAG GAAAGGGTCT GGAGTGGCTG GGAGTAATAT
161  GGGGTGGTGG AAGCACAAAT TATAATTCAG CTCTCATGTC
201  CAGACTGAGC ATCAGCAAAG ACAACTCCAA GAGCCAAGTT
241  TTCTTAAAAA TGAACAGTCT GCAAACTGAT GACACAGCCA
281  TGTACTACTG TGCCAAACAT AATAGTAACT ACGGGGGGTT
321  TGCTTACTGG GGCCAAGGGA CCACGGTCAC CGTCTCCTCA
361  AAAGCC
```

```
                                                     CDR-1
                      FR-1                          =====          FR-3
  1  VGLGETAAVR PGLVAPSQSL SISCTVSGFS LT           SYGVD           RLSISKDNSKSQV   WVR
            FR-2                  CDR-2
            ====             ==============
 41  QPPGKGLEWL G            VIWGGGSTNYN SALMS
            FR-3                  CDR-3                            FR-4
            ====             ==========                            ====
 81  FLKMNSLQTD DTAMYYCAK    HNSNYGGFAY                            WGQGTTVTVS  S

```
  1 CTTGACATCC AGATGACACA GTCTCCAGCA ATCATGTCTG
 41 CATCTCCAGG GGAGAGGGTC ACCATGACCT GCAGTGCCAG
 81 CTCAAGTATA CGTTACATAT ATTGGTACCA ACAGAAGCCT
121 GGATCCTCCC CCAGACTCCT GATTTATGAC ACATCCAACG
161 TGGCTCCTGG AGTCCCTTTT CGCTTCAGTG GCAGTGGGTC
201 TGGGACTTCT TATTCTCTCA CAATCAACCG AATGGAGGCT
241 GAGGATGCTG CCACTTATTA CTGCCAGGAG TGGAGTGGTT
281 ATCCGTACAC GTTCGGAGGG GGGACCAAGC TGGAGCTGAA
321 ACGGAAG
```

Fig. 18C

```
                    FR-1                                        CDR-1       FR-2
 1   LDIQMTQSPA     IMSASPGERV    TMTC         SASSSIRYIY       WYQQKP

FR-2           CDR-2                       FR-3
41   GSSPRLLIY      DTSNVAP       GVPFRFSGSG    SGTSYSLTIN      RMEA

FR-3           CDR-3                       FR-4
81   EDAATYYC       QEWSGYPYT                   FGGGTKLELK      RK
```

Fig. 18D

```
  1  GGTGAAACTG CAGGAGTCTG GAACTGAAGT GGTAAAGCCT
 41  GGGGCTTCAG TGAAGTTGTC CTGCAAGGCT TCTGGCTACA
 81  TCTTCACAAG TTATGATATA GACTGGGTGA GGCAGACGCC
121  TGAACAGGGA CTTGAGTGGA TTGGATGGAT TTTCCTGGA
161  GAGGGGAGTA CTGAATACAA TGAGAAGTTC AAGGGCAGGG
201  CCACACTGAG TGTAGACAAG TCCTCCAGCA CAGCCTATAT
241  GGAGCTCACT AGGCTGACAT CTGAGGACTC TGCTGTCTAT
281  TTCTGTGCTA GAGGGGACAA CTATAGGCGC TACTTTGACT
321  TGGGGGCCA AGGGACCACG GTCACCGTCT CCTCAAAG
```

Fig. 18E

|     | FR-1 | | | CDR-1 | FR-2 |
|---|---|---|---|---|---|
| 1 | VKLQESGTEV | VKPGASVKLS | CKASGYIFT | SYDID | WVRQTP |

|     | FR-2 | CDR-2 | | FR-3 |
|---|---|---|---|---|
| 41 | EQGLEWIG | WIFPGEGSTEY | NEKFKG | RATLSVDKSS STAYM |

|     | FR-3 | | CDR-3 | FR-4 |
|---|---|---|---|---|
| 81 | ELTRLTSEDS | AVYFCAR | GDNYRRYFDL | GGQGTTVTVS SK |

Fig. 18F

```
1    CTTGACATCC AGATGACACA GTCTCCAGCA ATCATGTCTG
41   CATCTCCAGG GGAGAGGGTC ACCATGACCT GCAGTGCCAG
81   CTCAAGTATA CGTTACATAT ATTGGTACCA ACAGAAGCCT
121  GGATCCTCCC CCAGACTCCT GATTTATGAC ACATCCAACG
161  TGGCTCCTGG AGTCCCTTTT CGCTTCAGTG GCAGTGGGTC
201  TGGGACTTCT TATTCTCTCA CAATCAACCG AATGGAGGCT
241  GAGGATGCTG CCACTTATTA CTGCCAGGAG TGGAGTGGTT
281  ATCCGTACAC GTTCGGAGGG GGGACCAAGC TGGAGCTGAA
321  ACGGAAG
```

|     | FR-1 |  |  | CDR-1 | FR-2 |
|-----|------|--|--|-------|------|
| 1   | LDIQMTQSPA | IMSASPGERV | TMTC | SASSSIRYIY | WYQQKP |

|     | FR-2 |  | CDR-2 |  | FR-3 |  |
|-----|------|--|-------|--|------|--|
| 41  | GSSPRLLIY | DTSNVAP | GVPFRFSGSG | SGTSYSLTIN | RMEA |

|     | FR-3 | CDR-3 | FR-4 |  |
|-----|------|-------|------|--|
| 81  | EDAATYYC | QEWSGYPYT | FGGGTKLELK | RK |

```
  1  GCTGTCAAGC TGCAGGAGTC TGGACCTGGC CTGGTGGGGC
 41  CCTCACAGAG CCTGTCCATC AGTTGCACTG CTTCTGGCTA
 81  CATCTTCACA AGTTATGATA TAGACTGGGT GAGGCAGACG
121  CCTGAACAGG GACTTGAGTG GATTGGATGG ATTTTCCTG
161  GAGAGGGGAG TACTGAATAC AATGAGAAGT TCAAGGGCAG
201  GGCCACACTG AGTGTAGACA AGTCCTCCAG CACAGCCTAT
241  ATGGAGCTCA CTAGGCTGAC ATCTGAGGAC TCTGCTGTCT
281  ATTTCTGTGC TAGAGGGGAC TACTATAGGC GCTACTTTGA
321  CTTGTGGGGC CAAGGGACCA CGGTCACCGT CTCCTCAAAG
```

Fig. 18I

|    |                | FR-1      |                  | CDR-1  |        |
|----|----------------|---------------|------------------|-----------|--------|
| 1  | AVKLQESGPG     | LVAPSQSLSI    | SCTASGYIFT       | SYDID     | WVRQT  |

|    | FR-2   |                     | CDR-2          |           |         |
|----|------------|---------------------|--------------------|-----------|---------|
| 41 | PEQGLEWIG  | WIFPGEGSTEY         | NEKFKG             | RATLSVD   | KSSSTAY |

|    | FR-3   |            | CDR-3   | FR-4     |
|----|------------|------------|-------------|--------------|
| 81 | MELTRLTSED | SAVYFCAR   | GDYYRRYFDL  | WGQGTTVTVSSK |

Fig. 18J

```
  1  CTTGACATCC AGATGACACA GTCTCCAGCA ATCATGTCTG
 41  CATCTCCAGG GGAGAGGGTC ACCATGACCT GCAGTGCCAG
 81  CTCAAGTATA CGTTACATAT ACAGAAGCCT ACAGAAGCCT
121  GGATCCTCCC CCAGACTCCT GATTATGAC ACATCCAACG
161  TGGCTCCTGG AGTCCCTTTT CGCTTCAGTG GCAGTGGGTC
201  TGGGACTTCT TATTCTCTCA CAATCAACCG AATGGAGGCT
241  GAGGATGCTG CCACTTATTA CTGCCAGGAG TGGAGTGGTT
281  ATCCGTACAC GTTCGGAGGG GGGACCAAGC TGGAGCTGAA
321  ACGGAAG
```

```
 1  LDIQMTQSPA  IMSASPGERV  TMTC  SASSSIRYIY  WYQQKP
                            FR-1                CDR-1      FR-2
41  GSSPRLLIY   DTSNVAP           GVPFRFSGSG  SGTSYSLTIN  RMEA
     FR-2       CDR-2                         FR-3
81  EDAATYYC    QEWSGYPYT         FGGGTKLELK  RK
     FR-3       CDR-3              FR-4
```

… # CD44 POLYPEPTIDES, POLYNUCLEOTIDES ENCODING SAME, ANTIBODIES DIRECTED THEREAGAINST AND METHOD OF USING SAME FOR DIAGNOSING AND TREATING INFLAMMATORY DISEASES

This is a continuation-in-part of PCT patent application. No. PCT/IL2004/000639, filed Jul. 15, 2004, which claims the benefit of priority from U.S. provisional patent application No. 60/495,876, filed Aug. 19, 2003, and from U.S. provisional patent application No. 60/486,919, filed Jul. 15, 2003.

This is also a continuation-in-part of U.S. patent application Ser. No. 10/012,969, filed Dec. 7, 2001 now abandoned, which is a continuation-in-part of PCT patent application No. PCT/IL00/00326, filed Jun. 7, 2000, which claims the benefit of priority from Israel patent application No. 133647, filed Dec. 21, 1999, and from Israel patent application No. 130356, filed Jun. 8, 1999.

FIELD AND BACKGROUND OF THE INVENTION

The present invention relates to polypeptides of a novel CD44 variant and to polynucleotides encoding same. Specifically the present invention relates to oligonucleotides specific for the novel CD44 polynucleotide variant, antibodies specific for the novel CD44 polypeptide variant, a cell hybridoma expressing monoclonal antibodies (mAbs) specific for said RA specific CD44 variant and mAb expressed thereby, and the use of these antibodies and oligonucleotides in the diagnosis and treatment of inflammatory diseases such as rheumatoid arthritis.

The following is a list of references which are intended for better understanding of the background of the present invention:

Aune, T. M., et al., Published EP Application No. 501233 (1992).
Hale, L. P., et al., WO 9409811 (1994)/
Herrlich et al., European Patent No. 538754, (1991).
Jalkanen, S., et al., WO 9500658, (1993).
Koopman et al., J. Exp. Med. 177:897-904 (1993)
Naor, D., et al., Adv. Cancer Res., 71:241, (1997).
Screaton, G. R., et al., Proc. Natl. Acad. Sci. USA, 89:12160, (1992).
Verdrengh, M., et al., Scand J. Immunol., 42:353, (1995)

The cell surface adhesion molecule, designated CD44, has been shown to be implicated in cell-cell and cell-matrix interactions, as well as in cell traffic and cell transendothelial migration.

CD44 is a single chain molecule comprising a conserved amino terminal extracellular domain, a nonconserved membrane proximal region, a variable region expressing various combinations of variant exons, a conserved transmembrane spanning domain and a conserved cytoplasmic tail. The genomic sequence of mouse and human CD44 includes 5 constant exons at the 5' terminus, and 5 constant exons at the 3' end. The mouse CD44 gene includes 10 variant exons in the middle of the molecule, designated $V_1$-$V_{10}$, resulting in a total of 20 exons. The human CD44 gene comprises only 9 of these 10 variant exons ($V_2$-$V_{10}$) thus comprising a total of 19 exons (Screaton, G. R., et al., 1992). Differential $V_2$-$V_{10}$ alternative splicing generates many isoforms of CD44 that express various combinations of variant exons (designated exon Vx, x=1-10), which are inserted in the membrane proximal domain and constitute the variable region of the molecule. These molecules are designated CD44 variants (CD44v). To date, a few dozen isoforms of CD44 are known.

In standard CD44 (CD44s, SEQ ID NO:5), constant exon number 5 is spliced directly to constant exon number 16 and therefore this molecule lacks the entire variable region. The resulting protein product is expressed predominantly on hematopoietic cells and therefore, this product is also known as hematopoietic CD44 (CD44H) or standard CD44 product (CD44s product, SEQ ID NO:6). In keratinocyte CD44, the longest CD44 identified so far, exon V3 to exon V10 are inserted in tandem between the two constant regions of the molecule.

The CD44 N-terminus contains the ligand binding site of the molecule. Hyaluronic acid (HA) is the principal ligand of CD44, but other extracellular matrix (ECM) components (e.g. laminin, collagen, fibronectin and chondroitin sulfate) as well as non-ECM constituents (mucosal vascular addressin, serglycin, osteopontin and class II invariant chain) can also interact with the CD44 receptor. Marked accumulation of CD44, and sometimes hyaluronic acid, is detected in areas of intensive cell migration and cell proliferation, as in wound healing, tissue remodeling, inflammation (including auto inflammation), morphogenesis and carcinogenesis.

The involvement of CD44 protein and variants thereof in autoimmune diseases is known. For example, it has been shown that anti-CD44 monoclonal antibodies (mAbs) can ameliorate the severity of experimentally induced autoimmune arthritis in mice (Verdrengh, M. et al. 1995). However, these mAbs are directed against the constant region of CD44 (and are thus designated anti-pan CD44 mAbs shared by all CD44 isoforms). Therefore, such mAbs may also block CD44 expressed on normal cells, which is required for migratory activity of immune and inflammatory cells engaged in microorganism eradication.

Monoclonal Abs directed against various variant regions of CD44 have also been suggested as potential agents for treatment of autoimmune diseases. Herrlich et al. describe mAbs directed against metastasis-specific variants of CD44v surface protein of a rat pancreatic adenocarcinoma (Herrlich et al., 1991). Anti-CD44-monoclonal antibodies, which inhibit T-cell proliferation, were also provided for treatment of various autoimmune diseases (Aune, T. M. et al., 1992). Monoclonal antibodies specific for forms of CD44 containing exon v6 were also reported as being useful for diagnosing inflammatory diseases (Jalkanen, S. et al., 1994). In addition, it has been reported (Hale, L. P., 1992) that administration of a CD44 protein, peptide or derivative can be used for treating various autoimmune diseases.

In an experimental arthritis mouse model (collagen-induced arthritis), injection of one of three different anti-CD44 mAbs, but not of the isotype-matched control mAbs, at disease onset, prevented an increase in footpad swelling and helped to maintain the clinical score at a very low level (Nedvetzki et al. 1999). Each of the three different types of anti-CD44 mAb recognized a distinct constant epitope of the CD44 receptor. All three antibodies displayed a similar anti-arthritic effect.

The involvement of CD44 in malignant processes has also been described (Naor, D., 1997). Anti-CD44 mAbs which were injected into mice, were shown to inhibit or prevent infiltration of various lymphoma and carcinoma cells into their target organs. In addition, transfection of a variant CD44 isoform into non metastatic rat pancreatic adenocarcinoma cells conferred metastatic potential to these cells.

SUMMARY OF THE INVENTION

According to one aspect of the present invention there is provided an isolated polypeptide comprising an antigen recognition domain capable of specifically binding a CD44 polypeptide as set forth in SEQ ID NO: 2 and incapable of binding a CD44 polypeptide selected from the group consisting of: SEQ ID NO: 4 or 6.

According to another aspect of the present invention there is provided an isolated polypeptide comprising a CD44 variant polypeptide which comprises contiguously a first amino acid sequence being at least 90% homologous to amino acid coordinates 1-302 of SEQ ID NO: 2, an alanine residue and a second amino acid sequence being at least 90% homologous to amino acid coordinates 304-700 of SEQ ID NO:2.

According to yet another aspect of the present invention there is provided an isolated polypeptide comprising an amino acid sequence as set forth in SEQ ID NO: 2.

According to still another aspect of the present invention there is provided a peptide of at least 8 amino acids derived from the isolated polypeptide and which comprises the alanine residue.

According to an additional aspect of the present invention there is provided an isolated polypeptide comprising an antigen recognition domain capable of specifically binding the isolated polypeptide of claim 7 and incapable of binding a CD44 polypeptide devoid of the alanine residue.

According to still further features in the described preferred embodiments the polypeptide is an antibody or an antibody fragment.

According to still further features in the described preferred embodiments the antibody or antibody fragment is humanized.

According to still further features in the described preferred embodiments the antibody or the antibody fragment is selected from the group consisting of a Fab fragment, an Fv fragment, a single chain antibody and a single domain antibody.

According to still further features in the described preferred embodiments the antibody is produced by a cell hybridoma having the depository Accession No. CNCM I-3015 (F8:33 hybridoma) or CNCM I-3016 (F8:33-6-8-10 hybridoma).

According to still further features in the described preferred embodiments the polypeptide is a CDR-containing recombinant polypeptide.

According to still further features in the described preferred embodiments a sequence of the CDR is selected from the group consisting of SEQ ID NOs: 22, 23, 24, 26, 27, 28, 30, 31, 32, 34, 35, 36, 38, 39, 40, 42, 43 and 44.

According to a further aspect of the present invention there is provided an isolated polynucleotide comprising a nucleic acid sequence encoding the polypeptide.

According to yet a further aspect of the present invention there is provided an isolated polynucleotide comprising a nucleic acid sequence encoding the peptide.

According to still a further aspect of the present invention there is provided a nucleic acid construct comprising the polynucleotide.

According to still further features in the described preferred embodiments the nucleic acid construct further comprising a promoter for regulating expression of the polynucleotide.

According to still a further aspect of the present invention there is provided an oligonucleotide capable of specifically hybridizing to the isolated polynucleotide and not to a polynucleotide encoding a CD44 polypeptide devoid of the alanine residue under stringent hybridization conditions.

According to still a further aspect of the present invention there is provided a pharmaceutical composition comprising as an active ingredient the polypeptide of and a pharmaceutically effective carrier or diluent.

According to still a further aspect of the present invention there is provided a pharmaceutical composition comprising as an active ingredient the oligonucleotide and a pharmaceutically effective carrier or diluent.

According to still a further aspect of the present invention there is provided a method of detecting an inflammatory disease in a subject comprising detecting in a biological sample of the subject a presence and/or a level of the polynucleotide, wherein the presence and/or level of the polynucleotide in the biological sample is indicative of the inflammatory disease in the subject.

According to still a further aspect of the present invention there is provided a method of detecting an inflammatory disease in a subject comprising detecting in a biological sample of the subject a presence and/or a level of the polypeptide, wherein the presence and/or level of the polypeptide in the biological sample is indicative of the inflammatory disease in the subject.

According to still a further aspect of the present invention there is provided a method of treating an inflammatory disease in a subject in need thereof, the method comprising administering to the subject a therapeutically effective amount of an agent capable of down-regulating activity or expression of the polypeptide, thereby treating the inflammatory disease in the subject.

According to still further features in the described preferred embodiments the agent is selected from the group consisting of:

(i) an oligonucleotide directed to an endogenous nucleic acid sequence expressing the polypeptide;

(ii) a polypeptide comprising an antigen recognition domain capable of specifically binding an endogenous amino acid sequence of the polypeptide; and (iii) a mucosal tolerance-inducing amount of a peptide derived from the polypeptide.

According to still further features in the described preferred embodiments the inflammatory disease is an autoimmune disease.

According to still further features in the described preferred embodiments the autoimmune disease is rheumatoid arthritis.

According to still a further aspect of the present invention there is provided a kit for diagnosing an inflammatory disease or a predisposition thereto in a subject, the kit comprising the polypeptide and at least one reagent for detecting complexes including the polypeptide.

According to still further features in the described preferred embodiments detecting the complexes is effected by an assay selected from the group consisting of immunohistochemistry, ELISA, RIA, Western blot analysis, FACS analysis, an immunofluorescence assay, and a light emission immunoassay.

According to still a further aspect of the present invention there is provided a kit for diagnosing an inflammatory disease or a predisposition thereto in a subject, the kit comprising the oligonucleotide and at least one reagent for detecting hybridization of the oligonucleotide.

According to still further features in the described preferred embodiments the at least one reagent is selected suitable for detecting hybridization via an assay selected from the group consisting of PCR, RT-PCR, chip hybridization, RNase protection, in-situ hybridization, primer extension, Southern blot, Northern blot and dot blot analysis.

The present invention successfully addresses the shortcomings of the presently known configurations by providing CD44 polypeptides, polynucleotides encoding same, antibodies directed thereagainst and method of using same for the diagnosis and treatment of inflammatory diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 8:
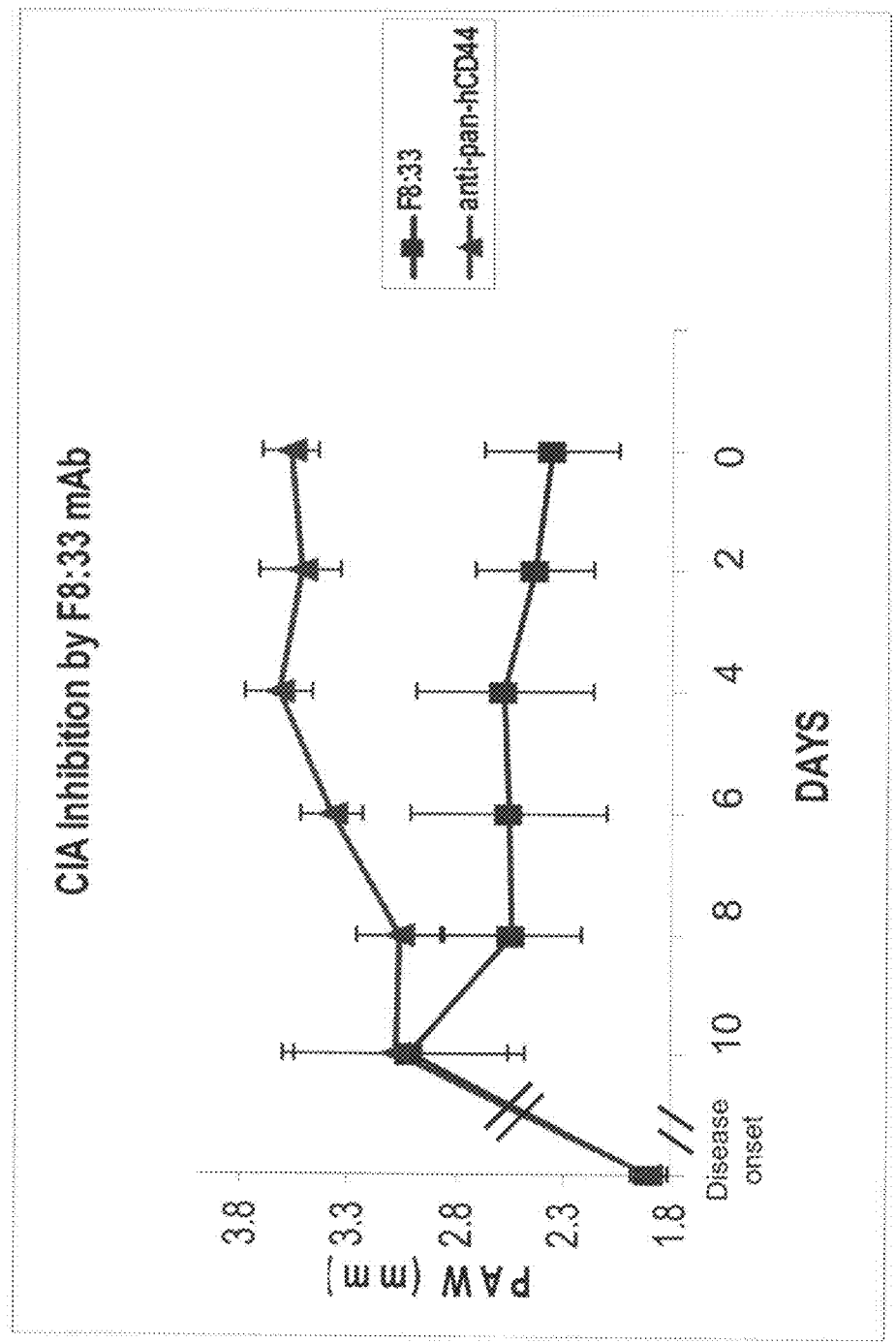

The patent or application file contains at least one drawing executed in color. Copies of this patent or patent application publication with color drawing(s) will be provided by the Office upon request and payment of the necessary fee.

FIGS. 1A-D show the genomic structure of CD44 (FIGS. 1A-B); agarose gel electrophoresis of primers representing the constant coding region of CD44 (FIG. 1C); and the partial nucleic acid sequence (exons 4 and 5) of RA-CD44 and CD44v3-v10, and the corresponding amino acid sequence, when the sequences are optionally aligned (FIG. 1D).

FIGS. 2A-B show histograms of fluorescence activated cell sorting (FACS) analysis of different Namalwa cells transfectants (as indicated), incubated with anti-pan-CD44 or anti-CD44v6 (FIG. 2A); the ability of mAb produced by F8:33 hybridoma to bind, at different concentrations, to the different Namalwa transfectants was also evaluated (FIG. 2B), wherein the binding of a fluorescein-coupled secondary antibody (IIAb) was used as the control.

FIGS. 3A-C show the results of ELISA (enzyme-linked immunosorbent assay) analysis of F8:33 derived anti-CD44vRA mAb binding to microwells coated with soluble CD44vRA, CD44v3-v10, CD44s (CD44vRA-Fc, CD44v3-v10-Fc, CD44s-Fc, respectively), while microwells coated with BSA served as the control (FIG. 3A). Binding of F8:33 derived anti-CD44 mAb was compared to that of anti-pan-CD44 mAb (FIG. 3B); FIG. 3C shows a Western Blot analysis of the different CD44 products (CD44s, CD44v3-v10 and CD44vRA, from the left Lanes I, II and III, respectively) immunoblotted with 3G5 anti-pan-human-CD44s mAb (Hermes 3, IgG1, ATCC).

FIGS. 4A-B show FACS analysis of the binding of commercial anti-pan-CD44 and anti-variant (anti-CD44v6 or anti-CD44v9) mAb to synovial fluid cells from the joint of an RA patient and to primary human keratinocytes provided from two individuals designated donor M and donor L (FIG. 4A) as well as flow cytometry analysis of the selective binding of F8:33 derived anti-CD44vRA (at two concentrations, 4 µg/ml and 2 µg/ml) to primary keratinocytes from the same two individuals and to synovial fluid cells (FIG. 4B).

FIGS. 5A-B show graphs of cell migration assays performed in the presence or absence of F8:33 anti-CD44vRA mAb (FIG. 5A) or of anti-pan CD44 mAb and according to which Namalwa transfectants were analyzed, in the absence or the presence of F8:33 anti-CD44vRA mAb (FIG. 5A) or anti-pan CD44 mAb (FIG. 5B) for their ability to cross HA-coated filters in a transwell migration assay and the percentage of cell migration was calculated by the number of cells that crossed the membrane in the presence of antibody, divided by the number of cells that crossed the membrane in its absence, ×100.

FIGS. 6A-B show graphs of cell migration assays performed in the presence or absence of F8:33 derived anti-CD44vRA mAb (FIG. 6A) or of anti-pan CD44 mAb (FIG. 6B) using synovial fluid cells from a joint of an RA patient, or primary keratinocytes, and evaluating their ability to cross HA-coated filters in a transwell migration assay. (The percentage of cell migration was calculated as in FIG. 5B).

FIGS. 7A-E show FACS analysis of the binding of F8:33-6-8-10 derived anti-CD44vRA mAbs to Namalwa-pcDNA3.1 cells, Namalwa-CD44s cells, Namalwa-CD44v3-v10 cells or Namalwa-CD44vRA cells. The antibody was present in the following concentrations: 1.2 mg/ml (FIG. 7A), 120 µg/ml (FIG. 7B), 12 µg/ml (FIG. 7C), 1.2 µg/ml (FIG. 7D) and 120 ng/ml (FIG. 7E).

FIG. 8 shows the effect of an anti-CD44vRA mAb (F8:33, squares) on Collagen-induced arthritis (CIA) in mice. Arthritis development was monitored for 10 days by measuring paw swelling. The values are the mean±SEM. Anti-pan-hCD44 was used as control (triangles).

Figure 9:
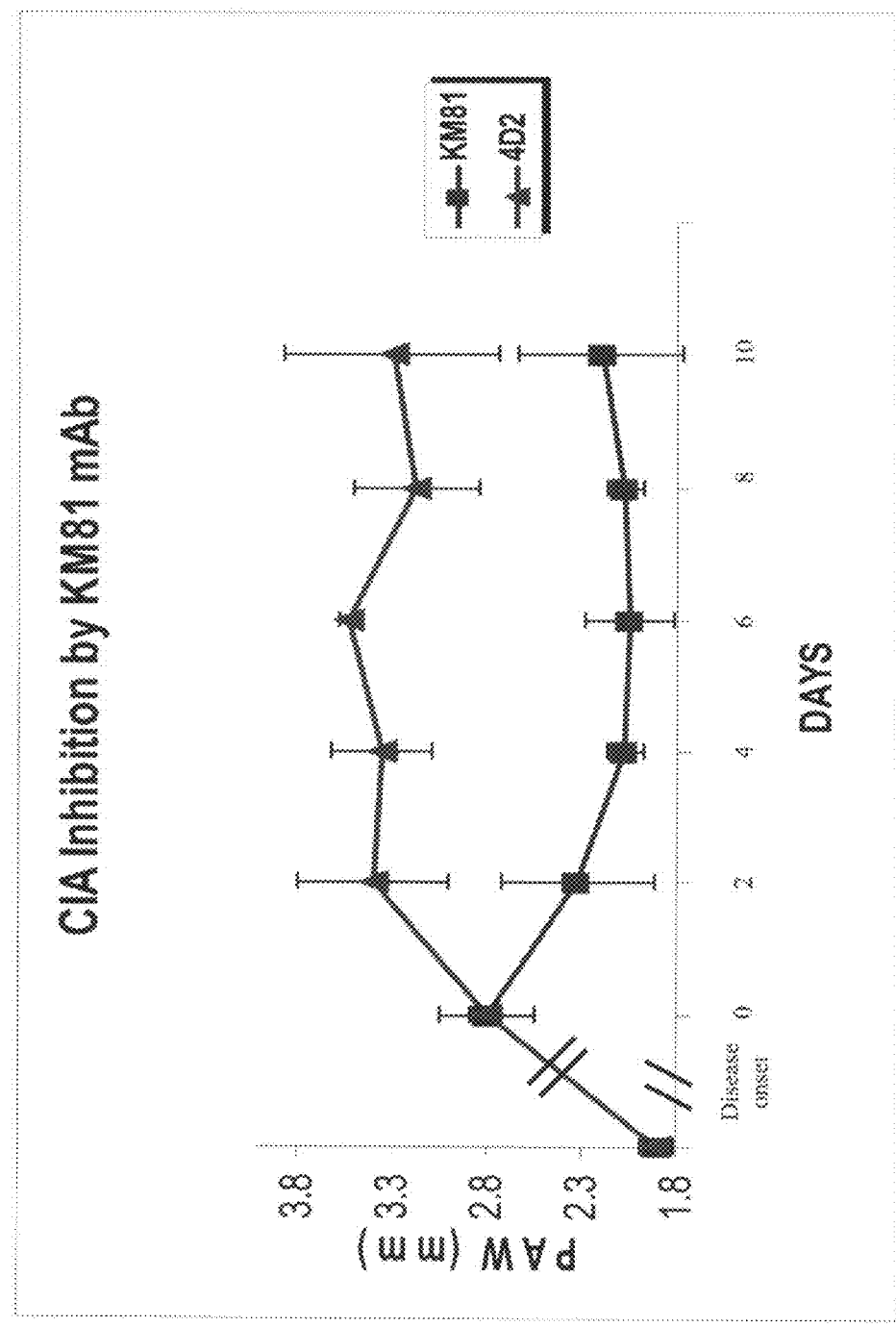

FIG. 9 shows the effect of KM81 (anti-pan mouse-CD44, squares) and 4D2 (control isotype-matched antibody, triangles) on CIA in mice. The values are the mean±SEM.

FIGS. 10A-H show FACS analysis of the binding of F8:33 anti-CD44vRA monoclonal antibody to peripheral blood lymphocytes (PBLs) of healthy individuals and to synovial fluid cells (SFCs) of an Rheumatoid Arthritis (RA) patient.

Figure 11:
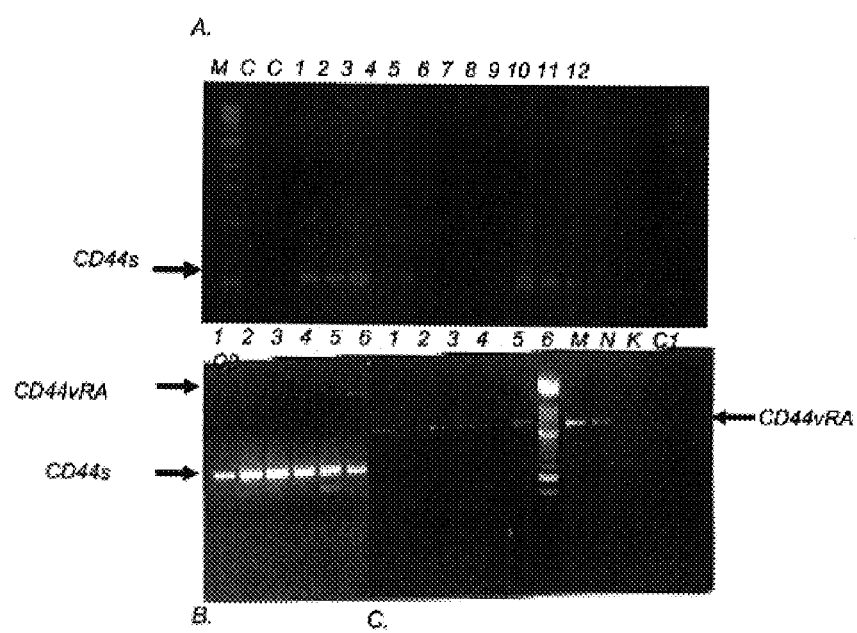

FIGS. 11A-C are agarose gel images showing RT-PCR analyses of CD44 variant expression in PBLs from healthy individuals. FIGS. 11A-C are agarose gel images showing RT-PCR analysis of CD44 molecules expression in PBLs from healthy individuals (11A) and in synovial fluid cells from RA patients (FIGS. 11B and 11C). FIG. 11B shows RT-PCR analysis using primers from constant regions of human CD44 molecule. FIG. 11C shows RT-PCR analysis using sense primer from variant exon 3 (v3).

Figure 12:
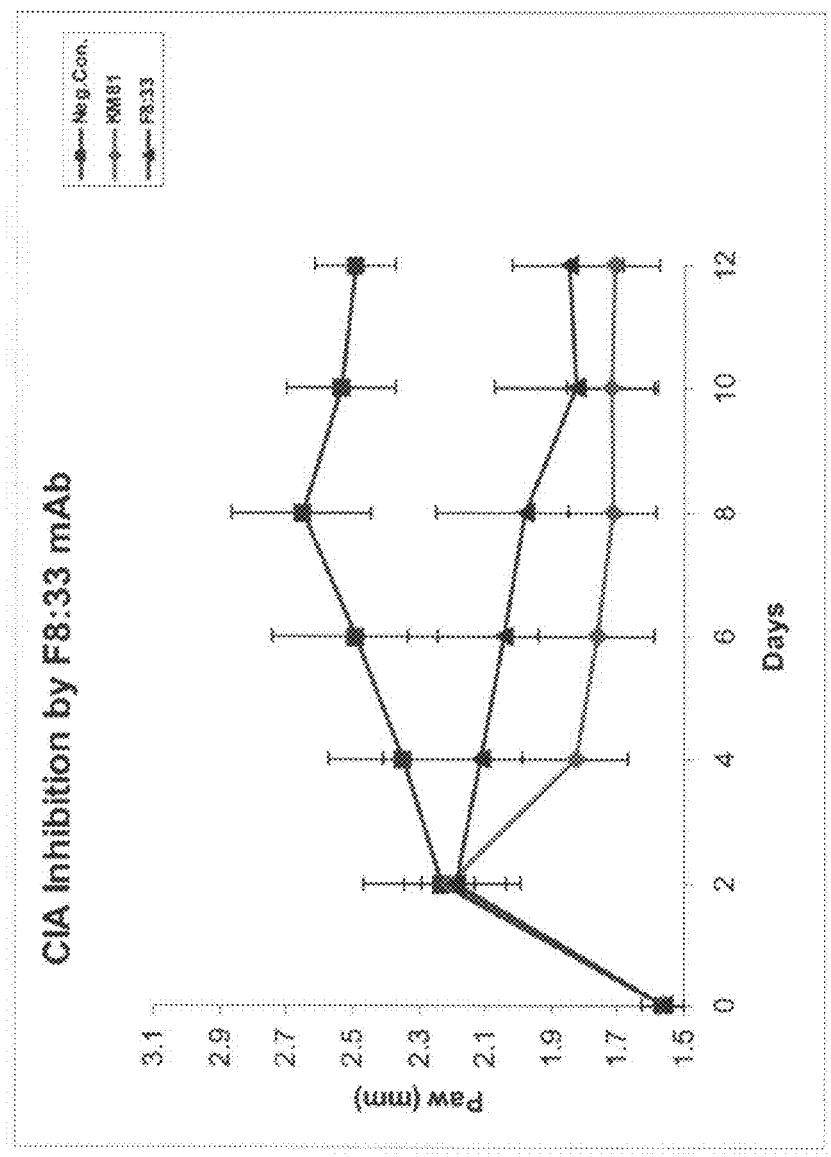

FIG. 12 is a graph depicting the therapeutic effect of anti CD44vRA antibody on collagen induced arthritis (CIA) of DBA/1 mice. Results are demonstrated by paw swelling.

FIGS. 13A-J show FACS analysis of the binding of various anti CD44 antibodies to arthritic and non-arthritic cells.

FIGS. 14A-D are graphs depicting apoptosis and survival of spleen cells from arthritic and non-arthritic mice treated with anti-CD44vRA mAb (F8:33).

Figure 15:
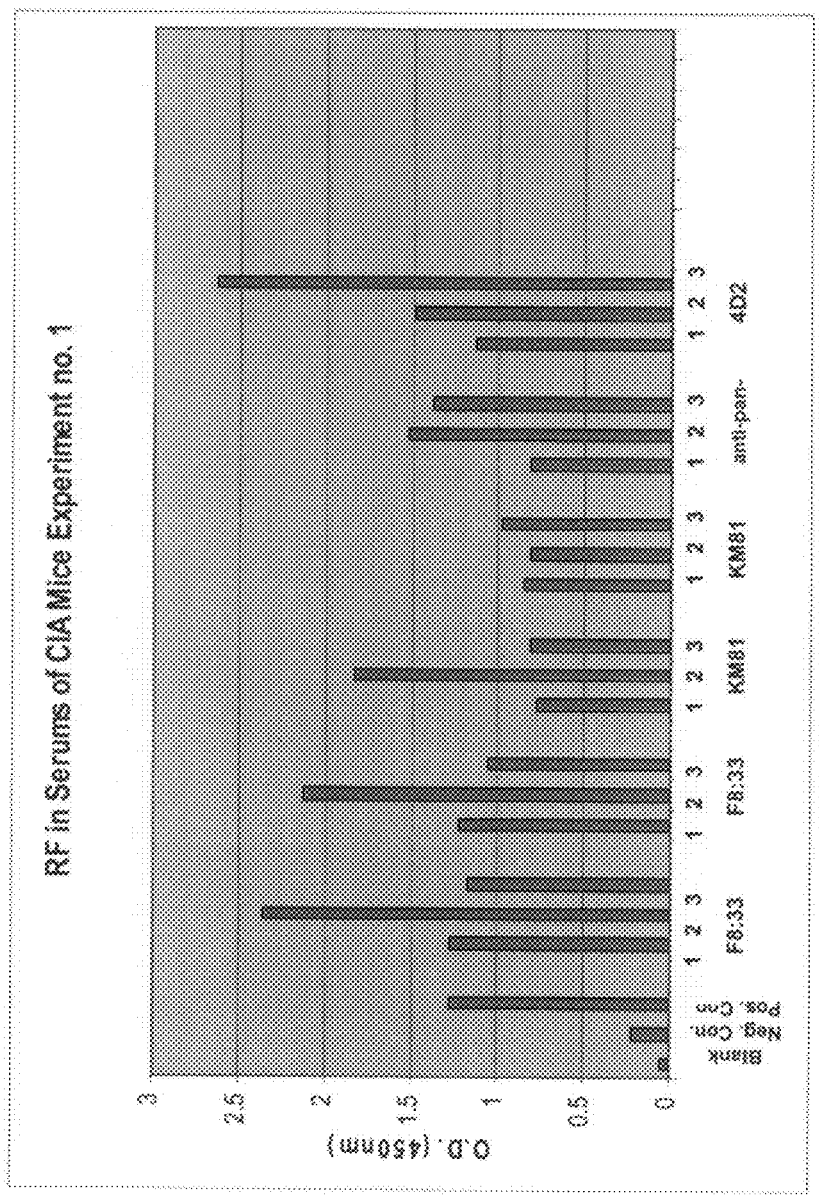
Figure 16:
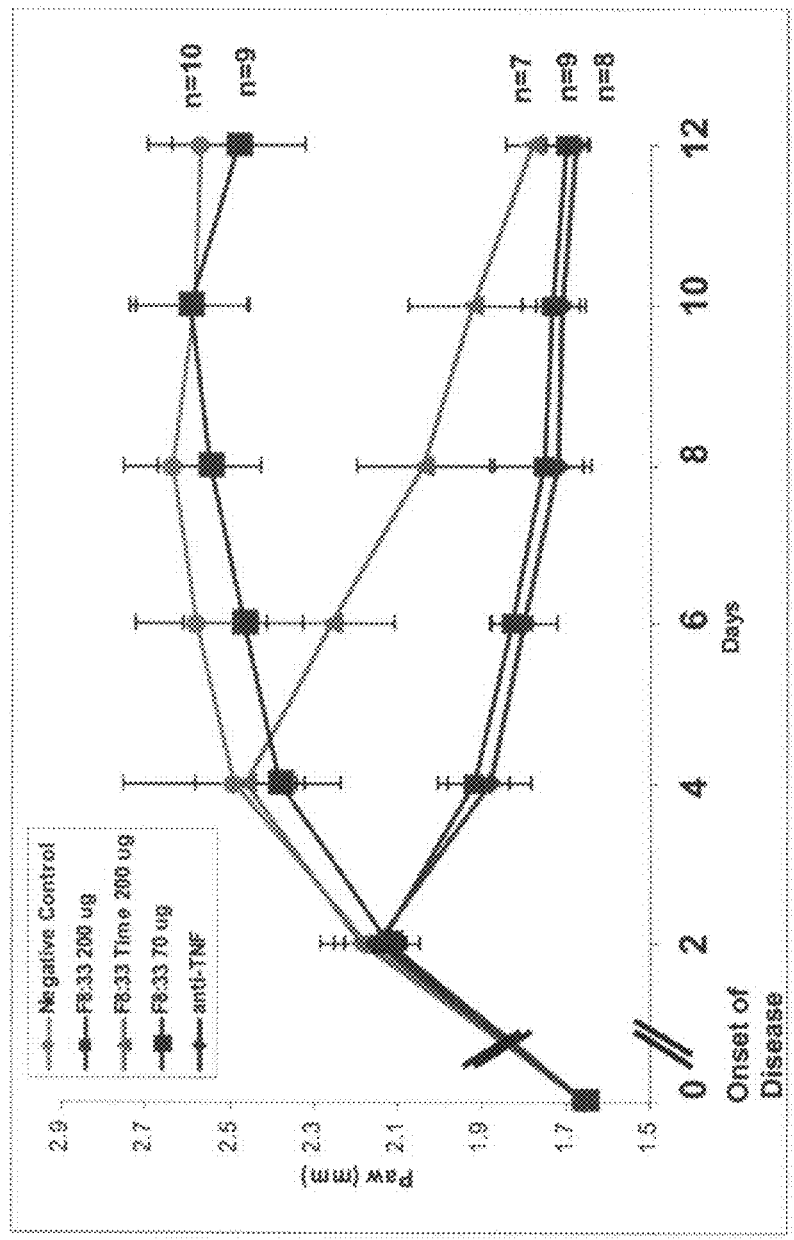

FIG. 15 is a bar graph depicting rheumatoid factor (RF) levels in CIA mice treated with rat anti-mouse cell surface immunoglobulin idiotype obtained from hybridoma 4D2 (negative control), F8:33 anti-human CD44vRA mAb or KM81-anti-mouse pan CD44 mAb. Levels of RF are indicated prior to disease induction (1) two days following disease onset (2) and 14 days following disease onset FIG. 16 is a graph depicting the therapeutic effect of various doses of anti CD44vRA antibody on arthritic mice as compared to treatment with Remicade™. Results are demonstrated by paw swelling.

Figure 17:
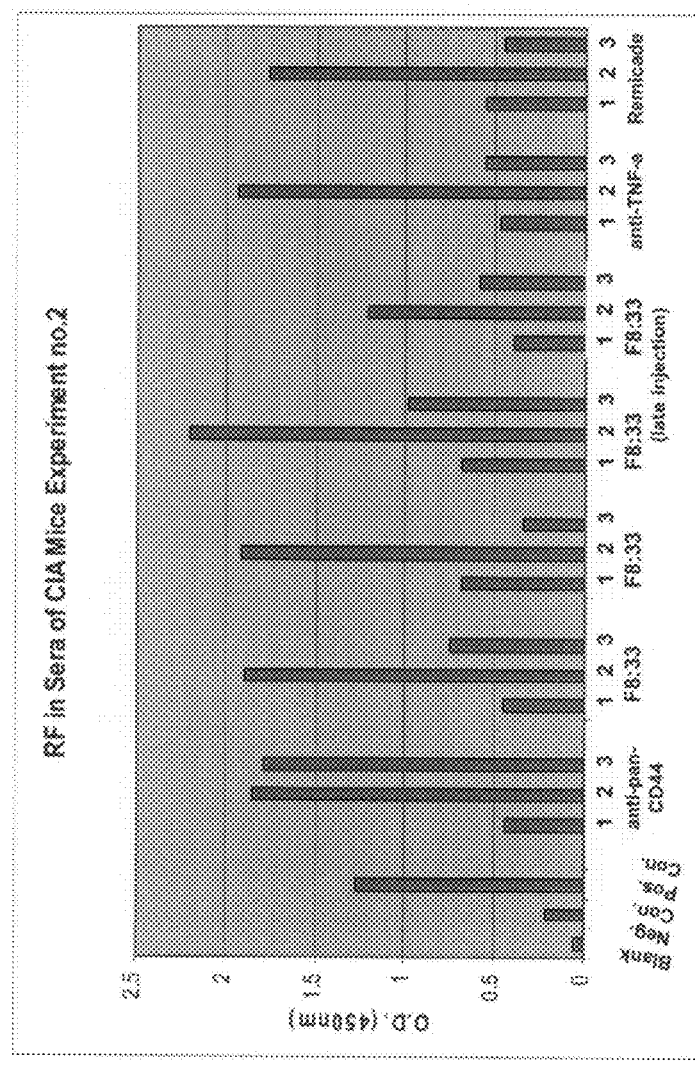

FIG. 17 is a bar graph depicting RF levels in mice treated as described in FIG. 16.

FIGS. 18A-L are nucleic acid and amino acid sequences of heavy and light chains of F8:33, F8:33-6-8-10 and MF1-16-11. FIG. 18A depicts the nucleic acid sequence of F8:33 mAb heavy chain (SEQ ID NO: 21). FIG. 18B depicts the amino acid sequence of F8:33 mAb heavy chain. CDRs 1, 2, 3 (SEQ ID NOs: 22, 23 and 24) as well as Framework regions are highlighted. FIG. 18C depicts the nucleic acid sequence of F8:33 mAb light chain (SEQ ID NO: 25). FIG. 18D depicts the amino acid sequence of F8:33 mAb light chain. CDRs 1, 2, 3 (SEQ ID NOs: 26, 27 and 28) as well as Framework regions are highlighted. FIG. 18E depicts the nucleic acid sequence of F8:33-6-8-10 mAb heavy chain (SEQ ID NO: 29). FIG. 18F depicts the amino acid sequence of F8:33-6-8-10 mAb heavy chain. CDRs 1, 2, 3 (SEQ ID NOs: 30, 31 and 32) as well as Framework regions are highlighted. FIG. 18G depicts the nucleic acid sequence of F8:33-6-8-10 mAb light chain (SEQ ID NO: 33). FIG. 18H depicts the amino acid sequence of F8:33-6-8-10 mAb light chain. CDRs 1, 2, 3 (SEQ ID NOs: 34, 35, 36) as well as Framework regions are highlighted. FIG. 18I depicts the nucleic acid sequence of MF 1-6-11 mAb heavy chain (SEQ ID NO: 37). FIG. 18J depicts the amino acid sequence of MF 1-16-11 mAb heavy chain. CDRs 1, 2, 3 (SEQ ID NOs: 38, 39 and 40) as well as Framework regions are highlighted. FIG. 18K depicts the nucleic acid sequence of MF 1-16-11 mAb light chain (SEQ ID NO: 41). FIG. 18L depicts the amino acid sequence of MF 1-16-11 mAb light chain. CDRs 1, 2, 3 (SEQ ID NOs: 42, 43, 44) as well as Framework regions are highlighted.

DESCRIPTION OF THE PREFERRED EMBODIMENTS

The present invention is of CD44 polypeptides, polynucleotides encoding same and antibodies and oligonucleotides directed thereagainst which can be used in the diagnosis and treatment of inflammatory diseases, such as rheumatoid arthritis.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CD44 is a multistructural and multifunctional cell surface molecule involved in cell proliferation, cell differentiation, cell migration, angiogenesis, presentation of cytokines, chemokines, and growth factors to the corresponding receptors, and docking of proteases at the cell membrane, as well as in signaling for cell survival or apoptosis. The genomic sequence of human CD44 includes 5 constant exons at the 5' terminus and 5 constant exons at the 3' terminus, as well as 9 variant exons encompassed therebetween. To date several dozens of splice variants of CD44 are known.

While reducing the present invention to practice, the present inventors have uncovered a novel variant mRNA transcript of CD44 (herein CD44-RA, SEQ ID NO: 1) from synovial cells of rheumatoid arthritis (RA) patients. This novel transcript contains the known CD44 constant and variant exons but also comprises three additional nucleotides (CAG) that are transcribed from the end of the intron bridging Exon v4 to Exon v5 and are inserted at the 5' end of Exon v5. This extra CAG sequence results in the insertion of a new codon for the amino acid alanine (SEQ ID NO: 2, see FIGS. 1A-D) while leaving the reading frame intact.

While further reducing the present invention to practice, the present inventors have developed antibodies which specifically bind the CD44 variant of the present invention but not other CD44 variants (e.g., SEQ ID NOs: 3 and 4) and as such can be used in the diagnosis, prognosis, prevention and treatment of RA and other diseases in which the variant CD44 transcript is involved and other disorders which are dependent on this CD44 variant for onset or progression.

As is illustrated hereinbelow and in the Examples section which follows, the present inventors have successfully shown that a specific antibody recognizing CD44vRA is capable of preventing and treating collagen-induced arthritis (CIA), in a mouse model of RA. This antibody exhibited a comparable therapeutic efficacy as compared to a known anti-RA drug, Remicade™.

Terminology

The isolated polynucleotide described above is also referred to "Rheumatoid Arthritis-CD44 (RA-CD44) variant nucleic acid coding sequence" interchangeably referred to also as the "RA-CD44 variant coding sequence", "CD44vRA" or "RA CD44 variant", refers to nucleic acid molecules having the sequence shown in SEQ ID NO: 1, nucleic acid molecules having at least 90% identity (see below) to said sequence and fragments (see below) of the above molecules of, at least 6 nucleotides, at least 8 nucleotides, at least 10 nucleotides, at least 12 nucleotides, at least 14 nucleotides, at least 16 nucleotides, at least 18 nucleotides, at least 20 nucleotides long. These molecules comprise sequences coding for a novel, naturally occurring, alternative splice variant of the native and known CD44 transcript. It should be emphasized that a novel variant of the present invention is a naturally occurring mature mRNA sequence resulting from alternative splicing of the primary pre-mRNA transcript and not merely a truncated, mutated or fragmented form of the known sequence.

This RA-CD44 variant sequence comprises Exons 1-5, 15-17 and 19 of the constant part of the CD44 gene as well as Exons 7-14 (v3-v10) of the variable region of the gene (Screaton et al, supra). The variant coding sequence comprises three additional bases (CAG) at the 5' end of Exon v5 as explained below.

"RA-CD44 Variant product—also referred at times as "variant product," "RA-CD44 variant protein," "variant protein" "RA-CD44 variant peptide" or "CD44vRA variant peptide" or "CD44 variant polypeptide"—is a polypeptide having an amino acid sequence encoded by the RA-CD44 variant coding sequence. By "polypeptide" is intended a peptide or protein, as well as peptides or proteins having chemically modified amino acids (see below) such as a glycopeptide or glycoprotein. The amino acid sequence of a preferred RA-CD44 variant product is shown in SEQ ID NO:2 "RA-CD44 variant product" also includes homologues (see below) of said amino acid sequence in which one or more amino acids has been added, deleted, substituted (see below) or chemically modified (see below) as well as fragments (see below) of this sequence having at least 6 amino acids.

"Nucleic acid molecule" or "nucleic acid" or "polynucleotide"—a single-stranded or double-stranded polymer composed of DNA nucleotides, RNA nucleotides or a combination of both types and may include natural nucleotides, chemically modified nucleotides and synthetic nucleotides.

"An isolated polynucleotide" refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

"Complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

"Genomic polynucleotide sequence" refers to a sequence derived (isolated) from a chromosome and thus it represents a contiguous portion of a chromosome.

"Composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

"Amino acid sequence"—a sequence composed of any one of the 20 naturally occuring amino acids, amino acids which have been chemically modified (see below), or synthetic amino acids.

"Fragment of RA CD44 variant nucleic acid coding sequence"—a fragment of at least 20 nucleotides of a RA-CD44 variant nucleic acid coding sequence having the sequence of, SEQ ID NO:1, or a fragment of at least 20 nucleotides of a RA-CD44 nucleic acid coding sequence having a sequence that is 90% identical to the sequence of SEQ ID NO:1, which at least 20 nucleotides does not appear as a continuous stretch in the original nucleic acid sequence (see below). The fragment will preferably comprise at least 30 nucleotides, more preferably at least 50 nucleotides, most preferably at least 100 nucleotides of the RA-CD44 sequence. At a minimum, the fragment will comprise the region corresponding to the variant splice junction site which corresponds to nucleotides 908-910 in SEQ ID NO: 1 (see explanation below). The fragment may be a sequence which was previously described in the context of the published CD44 RNA and which affects the amino acid sequence encoded by the known gene. In the case of the sequence of SEQ ID NO:1, the variant nucleic acid sequence, includes a sequence which was not included in the original CD44, sequence, (a sequence which was in the intron in the original sequence) and the fragment may be that additional sequence itself.

"Fragment of RA-CD44 variant products"—fragment of at least 6 amino acids of the RA-CD44 variant polypeptide having the amino acid sequence of SEQ ID NO:2, or fragments of at least 6 amino acids of a homologue of said polypeptide. The fragments will preferably comprise at least 10 amino acids, more preferably at least 20 amino acids, most preferably at least 30 amino acids, of said RA-CD44 variant (CD44vRA) polypeptide, or said homologue at a minimum, the fragment will comprise the region encoded by the variant splice junction site which corresponds to amino acid residue 303 in SEQ ID NO:2.

"Homologue of variant"—polypeptide having an amino acid sequence, that is at least 90% identical to the sequence of SEQ ID NO:2, or at least 90% identical to a fragment of at least 6 amino acids of the sequence of SEQ ID NO:2. The variation in amino acid sequence between the homologue and the sequence of SEQ ID NO:2 or a fragment thereof, arises from the addition, deletion, substitution or chemical modification of one or more amino acids of the sequence of SEQ ID NO:2. Where the homologue contains a substitution, the substitution is preferably a conservative one. The addition, deletion or substitution may be in regions or adjacent to regions where the RA-CD44 variant product differs from the original protein sequence (see below), however, a homologue will preferably retain the additional alanine residue (corresponding to residue 303 of SEQ ID NO:2) characteristic of the RA-CD44 variant product.

"Conservative substitution"—refers to the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution "Non-conservative substitution"—refers to the substitution of an amino acid in one class with an amino acid from another class; for example, substitution of an Ala, a class II residue, with a class III residue such as Asp, Asn, Glu, or Gln.

"Chemically modified"—when referring to the product of the invention, means a product (protein) where at least one of its amino acid residues is modified either by natural processes, such as processing or other post-translational modifications, or by chemical modification techniques which are well known in the art. Among the numerous known modifications typical, but not exclusive examples include: acetylation, acylation, amidation, ADP-ribosylation, glycosylation, glycosaminoglycanation, GPI anchor formation, covalent attachment of a lipid or lipid derivative, methylation, myristlyation, pegylation, prenylation, phosphorylation, ubiquitination, or any similar process. A preferred modification for the polypeptides of the present invention is pegylation.

"Optimal alignment"—is defined as an alignment giving the highest percent identity score. Such alignment can be performed using a variety of commercially available sequence analysis programs, such as the local alignment program LALIGN, using a ktup, of 1 default parameters and the default PAM.

"Having at least 90% identity"—with respect to two sets of amino acid or nucleic acid sequences, refers to the percentage of residues that are identical in the two sequences when the sequences are optimally aligned. Thus, at least 90% amino acid sequence identity means that at least 90% of the amino acids in two or more optimally aligned polypeptide sequences are identical, however this definition explicitly excludes sequences which are 100% identical with the original nucleic acid sequence or original protein sequence from which the variant of the invention was varied.

"Being at least 90% homologous"—refers to an amino acid sequence being at least 90%, at least 91% homologous, at least 92% homologous, at least 93% homologous, at least 94% homologous, at least 95% homologous, at least 96% homologous, at least 97% homologous, at least 98% homologous, at least 99% homologous, or more, say 100% homologous to SEQ ID NO: 2, as determined using BlastP software of the National Center of Biotechnology Information (NCBI) using default parameters.

"Expression vector"—refers to vectors that have the ability to incorporate and express heterologous DNA fragments in a foreign cell. Many prokaryotic and eukaryotic expression vectors are known and/or commercially available. Selection of appropriate expression vectors is within the knowledge of those having skill in the art.

The term "oligonucleotide" refers to a single-stranded or double-stranded oligomer or polymer of ribonucleic acid (RNA) or deoxyribonucleic acid (DNA) or mimetics thereof. This term includes oligonucleotides composed of naturally occurring bases, sugars, and covalent internucleoside linkages (e.g., backbone), as well as oligonucleotides having non-naturally occurring portions, which function similarly to respective naturally occurring portions.

"Deletion"—is a change in either nucleotide or amino acid sequence in which one or more nucleotides or amino acid residues, respectively, are absent as compared to the naturally occurring sequence.

"Insertion" or "addition"—is that change in a nucleotide or amino acid sequence which has resulted in the addition of one or more nucleotides or amino acid residues, respectively, as compared to the naturally occurring sequence.

"Substitution"—replacement of one or more nucleotides or amino acids by different nucleotides or amino acids, respectively as compared to the naturally occurring sequence. As regards amino acid sequences, the substitution may be conservative or non-conservative.

"An isolated polypeptide comprising an antigen recognition domain capable of speficically binding the CD44 polypeptide of the present invention" preferably refers to an antibody or an antibody fragment.

As used herein the term "diagnosing"/"detecting" refers to classifying a disease or a symptom, determining a severity of a disease, monitoring disease progression, forecasting an outcome of a disease and/or prospects of recovery.

"Biological sample"—The biological sample used in the methods of the invention can be any appropriate body-derived fluid sample including whole blood, peripheral blood monocytes, leukocytes, etc., preferably the biological sample will comprise synovial fluid cells (synovicytes, SFCs) or synovial fluid, or cellular extracts thereof.

The term "antibody" refers to antibodies of any of the classes IgG, IgM, IgD, IgA, and IgE antibody. The definition includes polyclonal antibodies or monoclonal antibodies. This term refers to whole antibodies or fragments of the antibodies comprising the antigen-binding domain of the anti-variant product antibodies, e.g. scFv, Fab, F(ab')2, other antibodies without the Fc portion, single chain antibodies, bispecific antibodies, diabodies, other fragments consisting of essentially only the variable, antigen-binding domain of the antibody, etc., which substantially retain the antigen-binding characteristics of the whole antibody from which they were derived. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

The term "substantially retain the antigen binding characteristics of the whole antibody" should be understood to mean that the antibody fragment, derivative or the recombinant antibody molecule specifically binds the CD44vRA product and that the affinity for the CD44vRA product as determined by Scatchard analysis or biacore analysis (as described below) is at least 30% of the binding affinity of the whole antibody (from which the fragment, derivative or recombinant antibody molecule was derived). In preferred embodiments, the binding affinity of the antibody fragment, derivative or recombinant antibody molecule for the CD44vRA product is at least 50% of the binding affinity of the whole antibody.

"Anti-CD44vRA antibody" or "Anti-CD44-RA variant antibody" refers to an antibody that specifically binds to the CD44vRA protein. The antibody may include polyclonal or monoclonal antibodies, antibody fragments, antibody derivatives and homologues and recombinant antibody molecules all derived from the monoclonal or polyclonal anti-CD44vRA antibody. Anti-CD44vRA antibodies particularly include the monoclonal antibodies (mAbs) produced by the particular hybridoma described herein (referred to herein by the terms "F8:33 mAb" and "F8:33-6-8-10 mAb" or "MF-1-16-11 mAb") as well as other antibodies that specifically bind to the CD44vRA protein (referred to as anti-CD44vRA mAbs).

"Recombinant antibody molecule"—refers to an antibody molecule that results from manipulation of a monoclonal antibody, typically at the nucleic acid level (i.e., gene, mRNA, etc.), by standard genetic engineering techniques. The recombinant antibody molecule will be referred to as "derived from" the monoclonal antibody. Recombinant antibody molecules include, for example, chimeric, humanized, primatized, single chain antibodies and fusion proteins. The recombinant antibody molecule substantially retains the antigen binding characteristics of the monoclonal antibody from which it was derived.

"Antibody fragment"—includes a fragment of at least 6 amino acids of the anti-CD44vRA antibody or fragments of at least 6 amino acids of a derivative of said polypeptide. The fragments will preferably comprise at least 10 amino acids, more preferably at least 20 amino acids, most preferably at least 30 amino acids, of said anti-CD44vRA antibody, or said homologue.

"Derivative of a monoclonal antibody (mAb)"—includes recombinant antibody molecules (as defined above) derived from the original mAb, as well as mAbs that are chemically modified (as defined above), and also includes mAb labeled with radioactive agents, fluorescent moieties, toxins, antibiotics, etc.

"Homologue of a monoclonal antibody (mAb)"—includes a protein having an amino acid sequence that is at least 90% identical to the sequence of the original mAb, or at least 90% identical to a fragment of at least 6 amino acids forming the original mAb. The variation in amino acid sequence between the homologue and the original mAb or a fragment thereof, arises from the addition, deletion, substitution or chemical modification of one or more amino acids of the original sequence. Where the homologue contains a substitution, the substitution is preferably a conservative one.

"Agonist"—as used herein, refers to a molecule which mimics the effect of the natural RA-CD44 variant product or has enhanced activity compared with the natural RA-CD44 variant product, or at times even increases or prolongs the duration of the biological activity of said variant product, as compared to that induced by the variant product itself. The mechanism may be by any mechanism known to prolonging activities of biological molecules such as binding to receptors; prolonging the lifetime of the molecules; increasing the activity of the molecules on its target; increasing the affinity of molecules to its receptor; inhibiting degradation or proteolysis of the molecules, etc. Agonists may be polypeptides, nucleic acids, carbohydrates, lipids, or derivatives thereof, or any other molecules which can positively modulate the activity of the variant product.

"Antagonist"—refers to a molecule which inhibits shortens the duration of the biological activity of the natural RA-CD44 variant product. This may be done by any mechanism known to deactivate or inhibit biological molecules such as blocking of the receptor, blocking of an active site, competition on a binding site, enhancement of degradation, etc. Antagonists may be polypeptides (e.g., antibodies), nucleic acids, carbohydrates, lipids, or derivatives thereof, or any other molecules which can negatively modulate the activity of said product.

"Treating a disease"—refers to administering a therapeutic substance effective to ameliorate symptoms associated with a disease, to lessen the severity or cure the disease, or to prevent the disease from occurring, to prevent the manifestation of symptoms associated with a disease before they occur, to slow down the progression of the disease or the deterioration of the symptoms associated therewith, to enhance the onset of the remission period, to slow down the irreversible damage caused in the progressive chronic stage of the disease, to delay the onset of said progressive stage, to improve survival rate or more rapid recovery, or a combination of two or more of the above.

The treatment regimen will depend on the type of disease to be treated and may be determined by various considerations known to those skilled in the art of medicine, e.g. the physicians. A preferred disease to be treated according to the invention is Rheumatoid Arthritis.

"Detection"—refers, in some aspects of the invention, to a method of detection of a disease, disorder, pathological or normal condition. This term may refer to detection of a predisposition to a disease as well as for establishing the prognosis of the patient by determining the severity of the disease.

"Probe" also referred to herein as "oligonucleotide (probe)"—a nucleic acid molecule comprising the variant coding sequence, or a sequence complementary therewith, when used to detect presence of other similar sequences in a sample. The detection is carried out by identification of hybridization complexes between the probe and the assayed sequence. The probe, in some embodiments, may be attached to a solid support or to a detectable label. The probe will generally be single stranded and will generally be between 5 even 10 and 100 nucleotides. The particular properties of a probe will depend upon the particular use and are readily within the competence of one of ordinary skill in the art to determine. Oligonucleotide modifications which are preferably used for in vivo diagnosis and treatment of diseases of the present invention are further described hereinbelow.

"Primer pair"—a set of two nucleic acid sequences ("primers"), each of which can serve to prime template-directed polymerization by a polymerase or transcriptase, which primers hybridize to the opposite strands of a double stranded nucleic acid sequence ("template") in such manner as to direct the polymerization (and amplification) of the double-stranded sequence nucleotide sequence located between regions of primer hybridization. Such a primer pair can be used in the well known polymerase chain reaction (PCR). The design of primers pairs is well known in the art and will depend upon the particular sequence to be amplified. In general, the primers are single-stranded, between 10 and 40 bases in length and hybridize to regions of the template sequence located between 50 and 2000 bases apart.

"Original nucleic acid sequence"—the nucleic acid sequence of the CD44 transcript present in synovial cells of non-rheumatoid arthritis individuals (such as osteoarthritic patients), having exons 1-5,7-17 and 19, with splice junctions as described in Screaton et al. (1992) see SEQ ID NO: 5, the entire contents of which is incorporated by reference herein.

"Original protein sequence"—the amino acid sequence of the CD44 protein encoded by the original nucleic acid sequence (i.e., SEQ ID NO: 6 Screaton et al. 1992).

As mentioned and in accordance with the present invention, it has been found that synovial cells removed from the joints of rheumatoid arthritis (RA) patients express a variant mRNA transcript of CD44 that is not found in synovial cells from healthy (that is, non-RA) individuals. This variant CD44 transcript has not previously been described. This CD44 variant will be referred to herein interchangeably as "RA-CD44 variant nucleic acid coding sequence" or "variant coding sequence" or "RA-CD44" or "RAvCD44".

In accordance with the invention, it was found that the novel RA-CD44 mRNA transcript which contains the constant Exons 1-5, 15-17 and 19 and variant Exons 7-14 (v3-v10) (as described by Screaton et al., 1992) also comprises three additional nucleotides (CAG) that are transcribed from the end of the intron bridging Exon v4 to Exon v5 and inserted at the 5' end of Exon v5 in positions 908-910 of SEQ ID NO:1. This extra CAG sequence results in an insertion of a new codon for the amino acid alanine. The last 3' original nucleotide "G" of Exon v4 (in position 907 of SEQ ID NO:1) together with the new "CA" nucleotides at the 5'end of the Exon v5 (positions 908 and 909 of SEQ ID NO:1) form an additional codon "GCA" which encodes the amino acid alanine (in position 303 of SEQ ID NO:2). The translation at both sides of the new insert is not changed as the original "GAT" codon (which encodes the amino acid aspartic acid) is preserved (by the new nucleotide "G" in position 910 of SEQ ID NO:1 and the next two original nucleotides "AT" in positions 911 and 912 of SEQ ID NO:1) as well as all the other codons of Exon v4 and v5. The generation of the extra CAG in the CD44 transcript from the SFCs of an RA patient is shown FIG. 1A:

As shown in Example 6 of the Examples section which follows, CD44vRA of the present invention is detected on synovial fluid cells of RA patients (in about 80% of the 49 patients examined) and to a lower extent (only 10%) on the (peripheral blood lymphocytes) PBLs of these patients. CD44vRA is not detected on the PBLs of healthy individuals. Cumulatively, these findings suggest that the expression of CD44vRA is confined to the inflammation site.

The above findings of a novel RA-CD44 coding variant open the way for diagnosis, prognosis, prevention and treatment of RA and other diseases in which the variant CD44 of the invention is involved.

The novel RA-CD44 variant of the invention is a naturally occurring sequence which has not been detected in cells of healthy individuals but only, in those of individuals suffering from rheumatoid arthritis. The RA-CD44 variant is presumably produced alternative splicing of the primary transcript of the known CD44 gene which occurs in cells of such patients and does not arise from truncation or mutation of the known CD44 gene.

The present invention provides by a first aspect, an isolated polynucleotide comprising a nucleic acid sequence encoding a CD44 variant polypeptide, which comprises, contiguously, a first amino acid sequence being at least 90% homologous to amino acid coordinates 1-302 of SEQ ID NO: 2, an alanine residue and a second amino acid sequence being at least 90% homologous to amino acid coordinates 304-700 of SEQ ID NO:2.

The above described isolated polynucleotide being an alternative splice variant selected from the group consisting of:

(a) a nucleic acid molecule comprising or consisting of the coding sequence SEQ ID NO:1;

(b) a nucleic acid molecule having at least 90% identity to the sequence of (a) and that differs from the original nucleic acid sequence from which the sequence of (a) was varied;

(c) fragments of (a) or (b) having at least 20 nucleotides and containing a sequence which is not present, as a continuous stretch of nucleotides, in the original nucleic acid sequence from which the sequence of (a) was varied. All of the above nuclei acid molecules will retain the nucleotide region corresponding to nucleotides 908-910 of SEQ ID NO:1.

The RA-CD44 nucleic acid molecule of the invention additionally includes nucleic acid molecules that are complementary to any of the above mentioned. The isolated polynucleotide/nucleic acid molecule may be in the form of DNA or in the form of RNA and include DNA, cDNA and genomic DNA and mRNA, synthetic DNA or RNA. The DNA may be doubled stranded or single stranded and, if single stranded may be the coding strand or the non-coding strand.

The RA-CD44 nucleic acid molecule may include the RA-CD44 variant coding sequence only or, alternatively, the coding region may be in combination with additional coding sequences such as those coding for fusion protein or signal peptides. In addition it may be combined with non-coding sequences such as introns and control elements.

Fragments as defined above are also within the scope of the present invention. Such fragments, typically comprise at least 20 bases which correspond to a region of the variant coding sequence. Preferably, the fragment comprises at least 30, 40, 50, 60, 70, 80, 90 or 100 or more, nucleotides which correspond to a region of the variant coding sequence.

As mentioned, the novel RA-CD44 transcript discovered by the present inventors differs from the previously described CD44 transcript by a variation of the splice site junction between exon 8 and exon 9 (Screaton et al., supra). This splice site variation results in the insertion of three additional nucleotides, "CAG" in the sense strand, at the splice junction between exons 8 and 9. Accordingly, the nucleic acid molecule of the invention, whether comprising the sequence of SEQ ID NO:1, or a complement or a fragment thereof, or sequences that are, ate least 90% identical to the sequence of SEQ ID NO:1, or a complement or fragment of thereof, will comprise at a minimum, the three nucleotides corresponding to the variant splice junction site.

A preferred embodiment, the RA-CD44 nucleic acid molecule comprises the sequence of SEQ ID NO:1 or fragments thereof or sequences having at least 90% identity to the above sequence as explained above. In addition, the RA-CD44 nucleic acid molecule includes nucleic acid sequence coding for the polypeptide of SEQ ID NO:2 or for fragments or homologues of said polypeptide. The coding sequence may be obtained by any of the methods known in the art. Typically screening of cDNA libraries using oligonucleotide probes which can hybridize to or PCR-amplify nucleic acid sequences which encode the variant products of the invention. A variety of cDNA libraries are commercially available and the procedures for screening and isolating cDNA clones are within the scope of a person skilled in the art. Such techniques are described in, for example, Sambrook et al., (1989) Molecular Cloning: A Laboratory Manual (2.sup.nd Edition), Cold Spring Harbor Press, Plain View; N.Y. Preferably, the cDNA library is prepared from synovial fluid cells.

The nucleic acid molecules can also be synthetically prepared in accordance with chemical synthesis methods known in the art. Alternatively, the nucleic acid molecules can be prepared recombinantly.

In addition, the variant nucleic acid molecule of the invention may be prepared by extracting cellular RNA from cells expressing the variant product. Such cells may, for example, be synovial fluid cells of RA patients. The RNA is then subjected to reverse transcriptase polymerase chain reaction (RT-PCR) in accordance with methods known in the art such as those described in Sambrook et al, supra. The amplification products of the PCR reaction are purified and sequenced.

Due to the degenerate nature of the genetic code, a plurality of alternative nucleic acid sequences other than that depicted in SEQ ID NO:1 can code for the polypeptide of the invention. Thus, the present invention further provides nucleic acid molecules comprising or consisting of a sequence which encodes the polypeptides of the invention. Alternative nucleic acid sequences coding for the same amino acid sequences coded by the sequence of SEQ ID NO:1 are also an aspect of the present invention.

The complete known sequence of the CD44 gene has been published and can be found for example in Screaton et al, 1992, supra, which also describes the location of exon-intron junctions. Comparison of the coding sequence of the invention to the known CD44 sequence may be carried out by any of the available computer programs.

The present invention also includes recombinant constructs comprising one or more of the RA-CD44 variant nucleic acid molecules described above. The constructs comprise a vector, such as a plasmid or viral vector, into which a nucleic acid molecule of the invention has been inserted, in a forward or reverse orientation. In a preferred aspect of this embodiment, the construct further comprises regulatory sequences, including, for example, a promoter, operably linked to the RA-CD44 sequence. Large numbers of suitable vectors and promoters are known to those of skill in the art, and are commercially available. Appropriate cloning and expression vectors for use with prokaryotic and eukaryotic hosts are also described in Sambrook, et al., (supra).

The present invention also relates to host cells which comprise vectors of the invention as well as to the production of the RA-CD44 variant product of the invention, by recombinant techniques. Host cells are genetically engineered (i.e., transduced, transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media, modified as appropriate for activating promoters, selecting transformants or amplifying the expression of the variant nucleic acid sequence. The culture conditions, such as temperature, pH and the like, are those previously used with the host cell selected for expression, and will be apparent to those skilled in the art.

The RA-CD44 variant nucleic acid coding sequences of the present invention may be included in any one of a variety of expression vectors for expressing a product. Such vectors include chromosomal, nonchromosomal and synthetic DNA sequences, e.g., derivatives of SV40; bacterial plasmids; phage DNA; baculovirus; yeast plasmids; vectors derived, from combinations of plasmids and phage DNA, viral DNA such as vaccinia, adenovirus, fowl pox virus, and pseudorabies. However, any other vector may be used as long as it is replicable and viable in the host. The appropriate RA-CD44 variant DNA sequence may be inserted into the vector by a variety of procedures. In general, the DNA sequence is inserted into an appropriate restriction endonuclease site(s) by procedures known in the art. Such procedures and related sub-cloning procedures are deemed to be within the scope of those skilled in the art.

The RA-CD44 variant coding sequence in the expression vector is operatively linked to an appropriate transcription control sequence (promoter) to direct mRNA synthesis. Examples of such promoters include: LTR or SV40 promoter, the E. coli lac or tip promoter, the phage lambda PL promoter, and other promoters known to control expression of genes in prokaryotic or eukaryotic cells or in viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate RA-CD44 variant DNA sequence as described above, as well as an appropriate promoter or control sequence, may be employed to-transfect or transform an appropriate host to permit the host to express the RA-CD44 variant protein. Examples of appropriate expression hosts include: bacterial cells, such as E. coli, Streptomyces, Salmonella typhimurium; fungal cells, such as yeast; insect cells such as Drosophila and Spodoptera Sf9; animal cells such as CHO, COS, HEK 293 or Bowes melanoma; adenoviruses; plant cells, etc. The selection of an appropriate host is deemed to be within the scope of those skilled in the art from the teachings herein. The invention is not limited by the host cells employed In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., and Battey, I. (1986) Basic Methods in Molecular Biology). Cell-free translation systems can also be employed to produce polypeptides using RNAs derived from the DNA constructs of the present invention.

The variant products can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Protein refolding steps can be used, as necessary, in completing configuration of the mature protein. Finally, high performance liquid chromatography (HPLC) can be employed for final purification steps.

The present invention further provides an isolated polypeptide comprising a CD44 variant polypeptide which comprises, contiguously, a first amino acid sequence being at least 90% homologous to amino acid coordinates 1-302 of SEQ ID NO: 2, an alanine residue and a second amino acid sequence being at least 90% homologous to amino acid coordinates 304-700 of SEQ ID NO:2.

According to an embodiment of the present invention the isolated polypeptide comprising or consisting of the amino acid sequence of SEQ ID NO:2 and fragments comprising at least-6 amino acids of the sequence of SEQ ID NO:2, homologues which are at least 90% identical to the sequence of SEQ ID NO:2, or at least 90% identical to fragments of at least 6 amino acids thereof, and fragments of the variant product, and its homologues, having at least 10 amino acids. All of the above polypeptides, fragments and homologues will retain an alanine residue corresponding to residue 303 of SEQ ID NO:2.

Due to the fact that the region which differs in the CD44 variant of the invention as compared to the original sequence is in the 5' part of exon v5, the homologues of the variant which are within the scope of the invention should be such which are derivated from the variant by a deletion, addition or substitution of an amino acid either in said region or in regions adjacent to it, but excluding deletion or substitution of the additional alanine residue.

Thus, the RA-CD44 variant product of the invention is a polypeptide encoded by the RA-CD44 variant coding sequence of the invention. The polypeptide has the amino acid sequence of the SEQ ID NO:2, or a fragment of at least 6 amino acids thereof, or a sequence homologue having at least 90% identity to the sequence of SEQ ID NO:2, or at least 90% identity to a fragment of at least 6 amino acids of SEQ ID NO:2, provided that the amino acid sequence is not identical to that of the original protein sequence from which it has been varied. The polypeptides, fragments and homologues of the invention will retain the alanine residue corresponding to amino acid 303 of SEQ ID NO:2.

The polypeptide of the invention can be made by any appropriate method including chemical or recombinant synthesis by techniques well known in the art (described above). Fragments may be obtained by enzymatic digestion (e.g. using clostrapaine) or chemical (CNBr) digestion of a longer protein. In such a case, the resulting peptides may be separated by methods known in the art such as by RP-HPLC and the separate peptides may then be used for sequencing (e.g. by Euro sequence BV).

The polypeptides in accordance with the invention may also be synthesized by methods known in the art such as on Abbymed 522 by Euro sequence BV.

The variant products may also be obtained by recombinant methods known in the art using the variant coding sequence.

The present invention additionally provides a fusion protein comprising the polypeptide having the sequence of SEQ ID NO:2, or fragments or homologues thereof, fused to another protein or peptide or a chemical moiety (e.g., drug, e.g., chemotherapy), as is well known in the art.

In view of the fact that the polypeptide of the invention contains a unique additional region which does not appear in CD44 obtained from synovial fluid cells from healthy individuals, antibodies or oligonucleotides [e.g., oligonucleotides which are specifically directed aganist nucleic acid coordinates 890-920 of SEQ ID NO: 1 and Nedvetzki et al. (2003) J. Clin. Invest. 111:1211-20] specifically directed against the RA-CD44 variant product (i.e., protein or RNA, respectively) or peptides derived therefrom may be used specifically for diagnosis, prognosis, prevention and therapy of various diseases in which cells expressing this CD44 variant molecule are involved.

By "specifically directed against" or "specifically bind" the RA-CD44 variant refers to the ability of an antigen recognition domain (e.g., such as of an antibody or antibody fragment) to specifically bind the CD44 polypeptide of the present invention (SEQ ID NO: 2) and inability to bind a prior art CD44 polypeptide such as selected from the group consisting of SEQ ID NO: 4 or 6. For example, the antibody of the present invention recognizes and binds to the RA-CD44 variant product in preference to other known CD44 proteins; in particular the anti-RA-CD44 antibodies will recognize and bind to the RA-CD44 variant (CD44vRA) product in preference to the original protein sequence. Generally, the affinity of anti-CD44vRA antibodies is at least 2-fold greater for binding to the CD44vRA than for binding to the original protein sequence or other CD44 isoforms. In a preferred embodiment, the binding affinity of anti-CD44vRA antibodies is at least 10-fold greater for binding to the CD44vRA than for binding to the original protein sequence or other CD44 isoforms. The binding affinity may be determined by a Scatchard analysis on antigens present on cell surfaces, a method that is well known in the art (see, for example, Hulmes, E. C. in *Receptor-ligand Interactions: a practical approach* Chapter 4. Rickwood and Hames, Eds. IRL Press.), as well as by Biacore analysis [e.g., van Regenmortel (2003) Dev. Biol. 112:141-51].

Specific binding may also be inferred from biological assays, such as the effect of the antibody on cell migration, therapeutic effects, the ability to induce cell aggregation, immunofluorescent studies, binding-competition assays, ability to induce apoptosis, effect thereof of CD44vRA signal transduction and the like. In such assays, an antibody would be defined as CD44vRA specific if the results using this antibody in the experimental setting differ in a statistically significant manner from those of the control antibody settings.

Thus, by an additional aspect, the present invention provides an isolated polypeptide comprising an antigen recognition domain capable of specifically binding a CD44 polypeptide as set forth in SEQ ID NO: 2 and incapable of binding a CD44 polypeptide selected from the group consisting of: SEQ ID NO: 4 or 6.

According to a preferred embodiment of this aspect of the present invention the isolated polypeptide is an antibody or an antibody fragment, such as a humanized antibody or antibody fragment.

Examples of antibodies of the present invention are those that are produced by cell hybridomas having the depository Accession No. CNCM I-3015 (F8:33 hybridoma), CNCM I-3016 (F8:33-6-8-10 hybridoma) or MF1-16-11 hybridoma.

According to another preferred embodiment of this aspect of the present invention, the polypeptide is a complementarity-determining region (CDR)-containing recombinant polypeptide. Such a polypeptide includes at least one CDR which is sufficient to mediate specific binding of the polypeptide of this aspect of the present invention to CD44vRA. It will be appreciated however, that such a polypeptide may include as much as all six CDRs combining the variable domains found in the heavy and light chains of anti CD44vRA antibodies. Examples of CDR sequences which can be implemented in the polypeptide are those set forth in SEQ ID NOs: 22, 23, 24, 26, 27, 28, 30, 31, 32, 34, 35, 36, 38, 39, 40, 42, 43 and 44.

Preferably, the polypeptides of this aspect of the present invention are neutralizing peptides, which are capable of binding CD44vRA and down-regulate at least one activity thereof (e.g., cell migration, further described hereinabove).

Anti-RA-CD44 antibodies of the present invention are selected from the group consisting of:

(a) antibodies which specifically bind the polypeptide encoded by the RA-CD44 variant nucleic acid coding sequence;

(b) fragments of the antibodies of (a) substantially retaining the antigen binding characteristics of the whole antibody; and (c) antibodies binding to an antigenic epitope bound by any one of the antibodies of (a) and (b) above.

The antibodies of the invention can be polyclonal antibodies or monoclonal. By a preferred embodiment, the antibodies of the invention are such which specifically bind the polypeptide of SEQ ID NO:2. Fragments of such antibodies substantially retaining the antigen-binding characteristics of these antibodies, antibodies binding to an antigenic epitope bound by such antibodies, as well as antibodies which bind to an antigen to which any one of the above Abs specifically bind are also within the scope of the invention. The anti-RA-CD44 antibody of the present invention will recognize an epitope of the RA-CD44 variant protein that is not present in the original protein sequence. The anti-RA-CD44 antibodies of the invention will preferably recognize an epitope comprising the alanine at residue 303 of SEQ ID NO.2. Alternatively, or in addition, the anti-RA-CD44 antibodies of the invention will recognize a neoepitope created by a change in the overall tertiary structure of the CD44 protein as a consequence of the alanine residue insertion at position 303. Such neoepitopes can be, inter alia, conformational epitopes, non-linear epitopes, carbohydrate epitopes or epitopes exposed by differential glycosylation. Epitopes recognized by the anti-RA-CD44 antibodies of the invention may include epitopes in the variant region of the peptide sequence at the beginning of the v5 exon, or the epitope may be on a different part of the molecule whose tertiary structure is altered by the insertion of the alanine residue of the variant polypeptide. Epitopes may be located in the v5 exon or one or more other exons, including, for example, the v6 exon. In some embodiments, antibodies that are specific for RA-CD44 do not bind and/or recognize an antigenic epitope on exon v6. The antibodies of the invention do not include the antibodies VFF6, VFF4, or VFF7. Antibodies that recognize the neoepitope of the RA-CD44 variant protein are useful in the diagnostic and therapeutic methods described herein. In accordance with this embodiment, the antibodies of the invention are used for diagnosis or treatment of infectious and other inflammatory diseases and autoimmune diseases, most preferably being RA as well as malignant diseases.

The present invention further provides mouse hybridoma cell lines which produce any of the monoclonal Abs of the invention. The hybridomas may be prepared by any of the methods known in the art (e.g. Kohler, G. and Milstein, C., Nature, 256:495-497, (1975). The present invention further provides recombinant-cell lines or transgenic animals expressing human or humanized anti-RA-CD44 antibodies of the invention.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (1972)]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single or more complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boemer et al., J. Immunol., 147(1):86-95 (1991)]. Similarly, human antibodies can be made by introduction of human immunoglobulin gene loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

It will be appreciated that targeting of particular compartment within the cell can be achieved using intracellular antibodies (also known as "intrabodies"). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-

7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269: 23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

For cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CHl region of the heavy chain such that a Fab fragment is expressed intracellularly. In another embodiment, the vector encodes a single chain antibody (scFv) wherein the variable regions of the light and heavy chains are linked by a flexible peptide linker [e.g., $(Gly_4Ser)_3$ and expressed as a single chain molecule. To inhibit marker activity in a cell, the expression vector encoding the intracellular antibody is introduced into the cell by standard transfection methods, as discussed hereinbefore.

Following is a description of specific hybridomas obtained according to the teachings of the present invention.

In accordance with the present invention, a hybridoma cell line has now been isolated that produces monoclonal antibodies (mAbs) which specifically bind to the CD44vRA product (CD44vRA) present in synovial fluid cells of individuals having rheumatoid arthritis (RA) but not present in the synovial fluid cells of non-RA individuals. Because the mAbs are specific for the CD44vRA product in preference to the original, wild type protein sequence (CD44v3-v10) or other isoforms of CD44, the monoclonal antibodies are useful, inter alia, in a variety of methods requiring the identification, isolation or targeting of the CD44vRA product.

The present invention further provides mouse hybridoma cell lines having the depository Accession Nos. CNCM I-3015 (for hybridoma F8:33) and CNCM I-3016 (for hybridoma F8:33-6-8-10), (referred to herein as the F8:33 and F8:33-6-8-10 hybridoma cell lines), deposited with the Collection Nationale De Cultures De Microorganismes (CNCM), Institut Pasteur, Paris, France, on Apr. 16, 2003) and mAbs produced by said cell line, clones and subclones. The hybridomas may be produced by any of the methods known in the art [e.g. Kohler, G., and Milstein C. Nature 256:495-497 (1975)]. The supernatants of the hybridoma cells are typically screened for antibody binding activity by any one of the methods known in the art such as flow cytometry or by enzyme linked immunosorbent assay (ELISA) or radio-immunoassay (RIA). The supernatants can be screened for production of mAbs capable of binding to any of the CD44vRA products (including fragments, derivatives or homologues thereof) or to cells expressing said products.

The monoclonal antibodies are typically produced by culturing the hybridoma cells under conditions suitable to produce the monoclonal antibody and isolating the mAb from the cell culture by well known techniques. Such conditions and techniques are well known in the art and are described in Mammalian cell biotechnology: a practical approach (Butler, M. Ed, IRL Press). The anti-CD44vRA antibodies of the invention may also be produced by recombinant genetic methods well known to a person skilled in the art; for example, as described in DNA Cloning 4: a practical approach, Chapter 3 (Glover, D. and Hames, B. Eds. IRL Press) and Bebbington et al. [Bio/Technology 10:169 (1992)].

As indicated hereinbefore, the recombinant antibody molecules include, for example, chimeric antibodies [Morrison S. L, Science 229:1202 (1985)], humanized antibodies [as described by, for example, Shin S. U. and Morrison S. L., Methods Enzymol., 178:459-476, (1989); Gussow D. and Seemann G., Methods Enzymol. 203:99-121 (1991)], bispecific antibodies [as described by, for example, Weiner L. M. et al., J. Immunol. 151:2877-2886 (1993); Goodwin D. A., Int. J. Rad. Appl. Instrum. 16:645-651 (1989)], single chain antibodies (scFv, as described by, for example, gritzapis A. D., et al. Br. J. Cancer 88:1292-1300, (2003)]), complete or fragmentary immunoglobulins [as described by, for example, Coloma M. J., et al., J. Immunol. Methods, 152:89:104, (1992); Nesbit M., et al., J. Immunol. Methods, 151:201-208 (1992); Barbas C. F., et al., Proc. Natl. Acad. Sci. USA, 89:10164:10168, (1992)], or antibodies generated by chain shuffling [as described by, for example, Winter G., et al., Annu. Rev. Immunol, 12:433-455, (1994)]. Humanized antibodies may be produced, for example, by CDR grafting (e.g. as described in published European patent application No. 0239400). Framework regions may also be modified (e.g. as described in European patent application No. 0519596). To humanize antibodies, methods such as PCR (for example, as described in European patent application Nos. 0368684; 0438310; or in international patent publication No. WO 92/07075) or computer modeling (for example, as described in international patent publication No. WO 92/22653) may be used. Fusion proteins, e.g. single chain antibody/toxin fusion proteins [as described, for example, by Chaudhary V. K., et al., Proc. Natl. Acad. Sci. USA, 87:9491-9494 (1990); Friedman P. N. et al., Cancer Res. 53:334-339, (1993)] may also be produced and thus also form part of the present invention.

The hybridoma cell line of the present invention comprises a nucleic acid encoding the monoclonal antibodies and such nucleic acid is also within the scope of the present invention. Nucleic acid encoding the anti-CD44vRA antibodies can be isolated from hybridoma cell lines by techniques that are well known in the art including those described in Antibody engineering: a practical approach McCafferty et al., Eds. IRL Press). Such nucleic acids are useful for preparation of additional cell lines or transgenic animals expressing the anti-CD44vRA antibodies or may be used in the preparation of recombinant antibody molecules.

The anti-CD44vRA Abs of the present invention include the monoclonal antibodies expressed by the hybridoma cell line of the present invention, whether actually produced in the hybridoma cells or produced by other techniques as are well known in the art; for example, produced in other cell types by transfer of the appropriate genetic material from the hybridoma cell (see for example *Monoclonal antibodies: the second generation*. Zola, H. Ed. BIOS Scientific, Chapters 4-9). Accordingly, there is also provided a monoclonal antibody as defined above, i.e. that reacts, similarly to the F8:33 derived mAb, with specificity to CD44vRA or to a fragment of said CD44vRA, the CD44vRA fragment comprising an amino acid sequence translated from the region flanking exon v4 to exon v5 of CD44vRA coding sequence or from part of said region and comprising an Ala residue which is not present in a corresponding fragment of CD44v3-v10 when CD44vRA and CD44v3-v10 are optimally aligned.

The present invention also concerns homologues, fragments and derivatives (such as chemically modified derivatives, radiolabeled derivatives, derivatives coupled to toxin or antibiotic molecules, and the like) of the antibodies as defined, all recognizing the antigenically distinct epitope (that includes the additional Ala) and thus substantially retaining the antigen binding specificity of the monoclonal antibodies. Also, recombinant antibody molecules that are derived from the monoclonal antibodies produced by the hybridoma cell lines F8:33, F8:33-6-8-10 or MF1-16-11 as well as additional hybridomas producing anti-CD44vRA mAbs and their clones and subclones that substantially retain the antigen binding characteristics of the monoclonal antibody are explicitly included in the present invention. It is within the skills of the average artisan to prepare homologues, fragments and derivatives of the antibody of the invention or, starting from a sequence analysis of the antibody and/or by use of the hybridoma cell line producing this antibody, to prepare recombinant antibody molecules with the same idiotype, i.e. antibody molecules having the same amino acid sequence in the region of the antigen binding site (complementarity-determining regions, CDR) as the antibody from hybridoma cell lines F8:33, F8:33-6-8-10 or MF1-16-11 as well as other hybridomas producing mAbs recognizing CD44vRA and their clones and subclones.

As indicated above, the anti-CD44vRA antibody of the present invention will recognize an epitope of the CD44vRA product that is not present in the original, wild type protein sequence (CD44v3-v10). The anti-CD44vRA antibodies of the invention preferably recognize an epitope comprising the Ala at residue 303 of SEQ ID NO:2. Alternatively, or in addition, the anti-CD44vRA antibodies of the invention recognize a neo-epitope created by a change in the overall tertiary structure of the CD44 protein as a consequence of the Ala residue insertion at position 303. Such neo-epitopes can be conformational epitopes, non-linear epitopes, carbohydrate epitopes or epitopes exposed by differential glycosylation. Epitopes may include the variant region of the peptide sequence flanking v5 exon or the epitope may be on a different part of the molecule whose tertiary structure is altered by the insertion of the Ala residue of the variant polypeptide.

Various hosts can be used for production of antibodies by the hybridoma technique including rats, mice, etc. The animals may be immunized by injecting the CD44vRA product (including said fragments, derivatives or homologues). Various adjuvants may be used to increase the immunological response such as Freund's, mineral gels, aluminum hydroxide, etc. The animals may also be immunized or challenged with cells, for example human Namalwa cells, that have been transfected with vectors carrying genetic material encoding the CD44vRA products (including fragments, derivatives or homologues thereof) as described herein.

In addition to the hybridoma technique mentioned above, clones and subclones of this hybridoma as well as continuous cell lines which produce antibodies obtained by additional techniques may also be used such as, for example, the EBV-hybridoma technique [Cole et al., Mol. Cell Biol. 62:109 (1984)].

The present invention also provides a nucleic acid molecule comprising or consisting of a non-coding sequence which is complementary to that of SEQ ID NO:1 or complementary to a sequence having at least 90% identity to said sequence, (under the conditions defined above) or a fragment of said two sequences (according to the above definition of fragment) also referred to herein as oligonucleotide. The complementary sequence may be a DNA sequence which hybridizes with the sequence of SEQ of ID NO:1 or hybridizes to a portion of that sequence having a length sufficient to inhibit the transcription of the complementary sequence. The complementary sequence may be a DNA sequence which can be transcribed into an mRNA being an antisense to the mRNA transcribed from SEQ ID NO:1 or into an mRNA which is an antisense to a fragment of the mRNA transcribed from SEQ ID NO:1 which has a length sufficient to hybridize with the mRNA transcribed from SEQ ID NO:1, so as to inhibit its translation. The complementary sequence may also be the mRNA or the fragment of the mRNA itself. Such complementary sequences may be used for various diagnostic and therapeutic indications as explained below.

Moderate to stringent hybridization conditions are characterized by a hybridization solution such as containing 10% dextrane sulfate, 1 M NaCl, 1% SDS and $5 \times 10^6$ cpm $^{32}$P labeled probe, at 65° C., with a final wash solution of 0.2× SSC and 0.1% SDS and final wash at 65° C. and whereas moderate hybridization is effected using a hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 50° C.

Oligonucleotides designed according to the teachings of the present invention can be generated according to any oligonucleotide synthesis method known in the art, such as enzymatic synthesis or solid-phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes 1-111, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The oligonucleotide of the present invention is of at least 17, at least 18, at least 19, at least 20, at least 22, at least 25, at least 30 or at least 40, bases specifically hybridizable with sequence alterations described hereinabove.

The oligonucleotides of the present invention may comprise heterocylic nucleosides consisting of purines and the pyrimidines bases, bonded in a 3'-to-5' phosphodiester linkage.

Preferably used oligonucleotides are those modified either in backbone, internucleoside linkages, or bases, as is broadly described hereinunder.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

Oligonucleotides of the present invention can be used to down-regulate expression of CD44vRA in a subject in need thereof (further described hereinbelow), in siRNA protocols, antisense, ribozyme and the like.

The present invention also provides peptides derived from the CD44 variant of the present invention. These peptides may be at least about 8 amino acids long, at least about 10 amino acids long, at least about 12 amino acids long, at least about 14 amino acids long, at least about 16 amino acids long, at least about 18 amino acids long, at least about 20 amino acids long, at least about 22 amino acids long, at least about 24 amino acids long, at least about 26 amino acids long, at least about 28 amino acids long, at least about 30 amino acids long (see e.g., SEQ ID NO: 14 and SEQ ID NOs. 15-18). Such peptides may be used for vaccination or inducing mucosal tolerance which was shown beneficial in the treatment of auto-immune diseases, such as RA. Such treatments are described, for example, in U.S. Pat. Nos. 5,935,577, 6,019, 970, 6,790,447, 6,703,361, 6,645,504, 5,961,977, 6,077,509, to Weiner et al., U.S. Pat. No. 5,843,449 to Boots et al., and U.S. patent application Ser. Nos. 10/451,370, 10/989,724, 09/944,592, 09/806,400, PCT Nos. IL99/00519 and IL02/00005 and Israel Patent Application No. 126447 to Harats et al., and in George et al., "Suppression of early atherosclerosis in LDL receptor deficient mice by oral tolerance with beta2 glycoprotein I", Cardiovascular Research 2004; 62:603-09, (which are incorporated herein by reference, as if fully set forth). Alternatively, such peptides may be used for generating antibodies which are specific for CD44vRA. Identification of antibodies which bind specifically to alanine 303 can be effected using methods known in the art, such as by affinity columns to which the immunizing peptides are bound and corresponding peptides which do not include the alanine are used as control.

Agents of the present invention which are capable of down-regulating activity or level of CD44 in a subject in need thereof (e.g., the above described antibodies, oligonucleotides and peptides) can be used to treat diseases which are dependent on CD44 (activity or expression) for their onset or progression, such as for the treatment of inflammatory diseases, such as, autoimmune diseases, preferably RA.

Thus, the present invention provides a method of treating an inflammatory disease in a subject in need thereof, the method comprising administering to the subject a therapeutically effective amount of an agent capable of down-regulating activity or expression of the CD44vRA, thereby treating the inflammatory disease in the subject.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II and type III hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8): 1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad. Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala 0. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3): 139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus. Note that several same diseases are can be classiffied to different classes of hypersensitivity, because the heterogeneity of these diseases.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt HO. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E.

et al., Electroencephalogr Clin Neurophysiol Suppl 1999; 50:419); acquired neuromyotonia, arthrogryposis multiplex congenita (Vincent A. et al., Ann N Y Acad. Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Agents (e.g., antibodies, oligonucleotides, peptides) capable of down-regualting activity or level of CD44 of the present invention can be provided to the subject per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include transmucosal, transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the preparation in a local rather than systemic manner, for example, via injection of the preparation directly into a specific region of a patient's body. Thus, for example, the preparation may be directly injected into a joint of an RA patient by intra-articular administration.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans. The estimate of the dosage can be also based by comparing with other equivalent drugs already in use (e.g., Remicade).

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the therapeutic agents of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Administration of such combination therapy can be simulataneous, such as in a single capsule having a fixed ration of these active agents, or in multiple capsules for each agent.

Thus, for example, the agents of the present invention can be administered along with nonsteroidal anti-inflammatory drugs (NSAID), disease-modifying antirheumatic drugs (DMARDS), corticosteroids, analgesics, Fibromyalgia medications, chemotherapeutic agents and others.

In accordance with the diagnostic aspect of the invention, there is provided a method of detecting an inflammatory disease in a subject. The method comprising detecting in a biological sample of the subject a presence and/or a level of the CD44vRA, wherein the presence and/or level of the polypeptide in the biological sample is indicative of the inflammatory disease in the subject.

Procedures for obtaining biological samples (i.e., biopsying) from individuals are well known in the art. Such procedures include, but are not limited to, bone biopsy, lymph node biopsy, pleural biopsy, skin biopsy, thyroid biopsy, CT-guided biopsy, joint biopsy, needle aspiration biopsy and breast biopsy. These and other procedures for obtaining tissue or fluid biopsies are described in details in healthatoz.com/healthatoz/Atoz/search.asp.

Specifically, a joint biopsy refers to joint or synovial biopsy. In the procedure a sample of the joint lining or synovial membrane or fluid is taken. Briefly, the procedure is effected in a clinical facility by a surgeon. A number of approaches are available to perform this biopsy: such as through an incision in the joint; with a scope inserted in the joint; or, more typically, by the insertion of a sharp instrument through the skin. The sample can be taken from any joint, typically the examined joint is the knee. A sharp instrument (trocar) is pushed into the joint space. A needle with an attached syringe is inserted into the joint to withdraw fluid for laboratory analysis. The surgeon may instill analgesic compounds into the joint and along the needle track before the needle is withdrawn. The trocar and then the biopsy needle is inserted and specimens taken. After the specimen is taken, both the trocar and the biopsy needle are removed.

Regardless of the procedure employed, once the biological sample is obtained, the presence of the CD44vRA variant in the sample is determined.

As mentioned above, determination of the level of CD44vRA variant in the biological sample can be effected at the transcriptional level (i.e., mRNA) using an oligonucleotide probe (such as described above), which is capable of specifically hybridizing under conditions allowing hybridization to said RA-CD44 variant coding sequence transcript and the formation of detectable probe-transcript hybridization complexes; and detecting said probe-transcript hybridization complexes, wherein the presence of said complexes indicates a high probability that the tested individual from which the sample was obtained has one of the diseases or disorders involving cells which comprise the RA-CD44 variant coding sequence transcript.

The above example method which is described as a qualitative one (i.e., presence), may also be quantitative (i.e., level). In accordance with such a quantitative method, the level of hybridization complexes in healthy individuals as well as the level of the complexes formed in individuals suffering from a specific disorder or disease involving cells which comprise the RA-CD44 variant RNA transcript is first determined. The level of the complexes detected in the tested individual is then compared to the known calibrated levels of the transcripts.

By quantization of the level of hybridization complexes and calibrating the quantified results it is possible also to detect the level of the transcript in the sample.

According to this same aspect, another method is provided for identifying subject having a disease or disorder involving cells which comprise the RA-CD44 variant coding sequence transcript, which method comprises the steps of (a) obtaining a biological sample from the tested individual;

(b) providing a primer pair capable of priming the amplification of a region of the RA-CD44 variant coding sequence transcript;

(c) contacting the biological sample with the primer pair under conditions allowing amplification of the RA-CD44 variant coding sequence transcript and the formation of detectable amplification product;

(d) detecting the amplification product, wherein the presence of the amplification product indicates a high probability that the tested individual from which the sample was obtained has one of the diseases or disorders involving cells which comprise the RA-CD44 variant coding sequence transcript.

Amplification of the RA-CD44 variant coding sequence transcript can conveniently be accomplished using the well known polymerase chain reaction (PCR) technique (Saiki et al. Science 230: 1350(1995); Mullis et al. Methods Enzymol. 155:335 (1987), Erlich et al. Nature (London) 331; 461 (1988)). A primer pair is chosen to amplify an appropriate portion of the RA-CD44 variant coding sequence transcript as is well within the competence of one of ordinary skill in the art. The primer pair will typically amplify a portion of the RA-CD44 variant coding sequence transcript in the region in which the variant transcript differs from the original nucleic acid sequence.

By a preferred embodiment, the above diagnostic or prognostic methods are used for diagnosis or prognosis of RA or for following up the disease in a tested-indivdual. According to this embodiment, the nucleic acid probe contacted with the sample is such which is able to specifically detect the presence of an mRNA transcribed from the variant coding sequence having the sequence of SEQ ID NO:1, or the primer pair is such as to amplify a portion of the mRNA transcribed from the variant coding sequence having the sequence of SEQ ID NO:1. In particular, the nucleic acid probe or the primer pair will be such as to allow detection of the presence of an mRNA transcribed from the variant coding sequence having the sequence of SEQ ID NO:1, in preference to detection of an mRNA transcript having the original nucleic acid sequence. In accordance with the findings of the present invention, a qualitative method may be sufficient to identify an individual suffering from RA since the novel coding sequence has been identified in such patients only. However, various degrees of the disease as well as other related diseases or disorders may be identified using a quantitative method as described above.

It will be appreciated that in accordance with the diagnostic aspect of the invention, detection of CD44vRA presence or level can also be effected at the protein level, such as by using the above-described antibodies or antibody-fragments.

Detection of the antibody-antigen complexes can be carried out by any of a number of techniques well known in the art, including, without limitation those described in Harlow and Lane, Antibodies: A Laboratory Manual, Cold Spring Harbor Laboratory, 1988.

As described with regards to the diagnostic assays based on the detection of the coding sequence mRNA transcript, in this case as well, the method may be quantitzed to determine the level or amount of the variant product in the sample which may be indicative of the kind of disease or the extent of the disease from which the tested individual is suffering.

By a preferred embodiment, the above diagnostic method is used for identifying an individual having a disorder or disease involving cells which express the RA-CD44 variant product. However, the method may also be used for identifying an individual having a disease involving cells which express isoforms of the CD44 protein other than the RA-CD44 variant of the invention.

As indicated above, this method as well can be quantitized to determine the level or the amount of the RA-CD44 variant product in the sample, alone or in comparison to the level of the original protein sequence.

The diagnostic reagents described hereinabove can also be included in kits. Such kits comprise an additional aspect of the invention. Diagnostic kits, for example, would typically include one or more of the Abs of the invention, a conjugate of a specific binding partner for the Abs, a label capable of producing a detectable signal and directions for its use. A kit for diagnosing predisposition to, or presence of a disease associated with the CD44vRA of the present invention in a subject can include an antibody (e.g., labeled) of the present invention in a one container and a solid phase for attaching multiple biological samples packaged in a second container with appropriate buffers and preservatives and used for diagnosis.

The following summarizes methods of determining levels of biomolecules (i.e., RNA or protein) of interest in biological samples.

The expression level of the RNA in the cells of the present invention can be determined using methods known in the art.

Northern Blot Analysis

This method involves the detection of a particular RNA in a mixture of RNAs.

An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radioisotopes or enzyme-linked nucleotides. Detection may be performed by autoradiography, colorimetric reaction, or chemiluminescence. This method allows for both quantitation of an amount of a particular RNA molecule and determination of its identity by a relative position on the membrane which is indicative of a migration distance in the gel during electrophoresis.

RT-PCR Analysis

This method uses PCR amplification of relatively rare RNA molecules. First, RNA molecules are purified from cells and converted into complementary DNA (cDNA) using a reverse transcriptase enzyme (such as an MMLV-RT) and primers such as oligo-dT, random hexamers, or gene-specific primers. Then by applying gene-specific primers and Taq DNA polymerase, a PCR amplification reaction is carried out in a PCR machine. Those of ordinary skill in the art are capable of selecting the length and sequence of the gene-specific primers and the PCR conditions (i.e., annealing temperatures, number of cycles, and the like) that are suitable for detecting specific RNA molecules. It will be appreciated that a semi-quantitative RT-PCR reaction can be employed, by adjusting the number of PCR cycles and comparing the amplification product to known controls.

RNA In Situ Hybridization Stain

In this method DNA or RNA probes are attached to the RNA molecules present in the cells. Generally, the cells are first fixed to microscopic slides to preserve the cellular structure and to prevent the RNA molecules from being degraded, and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those skilled in the art are capable of adjusting hybridization conditions (i.e., temperature, concentration of salts and formamide, and the like) for specific probes and types of cells. Following hybridization, any unbound probe is washed off and the slide is subjected to either a photographic emulsion, which reveals signals generated using radio-labeled probes, or to a colorimetric reaction, which reveals signals generated using enzyme-linked labeled probes.

In Situ RT-PCR Stain

This method is described by: Nuovo, G. J. et al. (1993). Intracellular localization of polymerase chain reaction (PCR)-amplified hepatitis C cDNA. Am J Surg Pathol 17, 683-690); and Komminoth, P. et al. (1994) Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract 190, 1017-1025). Briefly, the RT-PCR reaction on fixed cells involves the incorporation of labeled nucleotides in the reaction. The reaction is effected using a specific in situ RT-PCR apparatus, such as the laser-capture microdissection PixCell II™ Laser Capture Microdissection (LCM) system available from Arcturus Engineering (Mountainview, Calif., USA).

Oligonucleotide Microarray

In this method, oligonucleotide probes capable of specifically hybridizing with the polynucleotides of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., blood cells), RNA is extracted from the cell sample using methods known in the art (using, e.g., a TRIZOL® solution, Gibco-BRL™, USA). Hybridization can take place using either labeled oligonucleotide probes (e.g., 5'-biotinylated probes) or labeled fragments of complementary DNA (cDNA) or RNA (cRNA). Briefly, double-stranded cDNA is prepared from the RNA using reverse transcriptase (RT) (e.g., Superscript™ II RT), DNA ligase, and DNA polymerase I, all according to the manufacturer's instructions (Invitrogen Life Technologies, Frederick, Md., USA). To prepare labeled cRNA, the double-stranded cDNA is subjected to an in vitro transcription reaction in the presence of biotinylated nucleotides using, e.g., the BioArray™ HighYield™ RNA Transcript Labeling Kit (Enzo Diagnostics, Inc., Farmingdale, N.Y., USA). For efficient hybridization the labeled cRNA can be fragmented by incubating the RNA in 40 mM Tris Acetate (pH 8.1), 100 mM potassium acetate, and 30 mM magnesium acetate, for 35 minutes at 94° C. Following hybridization, the microarray is washed and the hybridization signal is scanned using a confocal laser fluorescence scanner, which measures fluorescence intensity emitted by the labeled cRNA bound to the probe arrays.

For example, in the Affymetrix® GeneChip® Microarray (Affymetrix, Inc., Santa Clara, Calif., USA), each gene on the array is represented by a series of different oligonucleotide probes, of which each probe pair consists of a perfect-match oligonucleotide and a mismatch oligonucleotide. While the perfect-match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent DNA Microarray Scanner™ (Agilent Technologies, USA) and the Microarray Suite™ (MAS) (Affymetrix, Inc.) software subtracts the non-specific signal of the mismatch probe from the signal resulting from the perfect-match probe.

Alternatively, expression level of proteins expressed in cells can be determined using methods known in the art. Activity of CD44vRA can be determined using a cell migration assay such as described in the Examples section which follows.

Enzyme-Linked Immunosorbent Assay (ELISA)

This method involves fixation of a sample containing a protein substrate (e.g., fixed cells or a proteinaceous solution) to a surface such as a well of a microtiter plate. A substrate-specific antibody coupled to an enzyme is applied and allowed to bind to the substrate. Presence of the antibody is then detected and quantitated by a calorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western Blot

This method involves separation of a substrate from other protein by means of an acrylamide gel followed by transfer of the substrate to a membrane (e.g., nitrocellulose, nylon, or PVDF). Presence of the substrate is then detected by antibodies specific to the substrate, which are in turn detected by antibody-binding reagents. Antibody-binding reagents may be, for example, protein A or secondary antibodies. Antibody-binding reagents may be radiolabeled or enzyme-linked, as described hereinabove. Detection may be by autoradiography, calorimetric reaction, or chemiluminescence. This method allows both quantitation of an amount of substrate and determination of its identity by a relative position on the membrane indicative of the protein's migration distance in the acrylamide gel during electrophoresis, resulting from the size and other characteristics of the protein.

Radioimmunoassay (RIA)

In one version, this method involves precipitation of the desired protein (i.e., the substrate) with a specific antibody and radiolabeled antibody-binding protein (e.g., protein A labeled with $I^{125}$) immobilized on a precipitable carrier such as agarose beads. The radio-signal detected in the precipitated pellet is proportional to the amount of substrate bound.

In an alternate version of RIA, a labeled substrate and an unlabelled antibody-binding protein are employed. A sample containing an unknown amount of substrate is added in varying amounts. The number of radio counts from the labeled substrate-bound precipitated pellet is proportional to the amount of substrate in the added sample.

Fluorescence-Activated Cell Sorting (FACS)

This method involves detection of a substrate in situ in cells bound by substrate-specific, fluorescently labeled antibodies. The substrate-specific antibodies are linked to fluorophores. Detection is by means of a cell-sorting machine, which reads the wavelength of light emitted from each cell as it passes through a light beam. This method may employ two or more antibodies simultaneously.

Immunohistochemical Analysis

This method involves detection of a substrate in situ in fixed cells by substrate-specific antibodies. The substrate specific antibodies may be enzyme-linked or linked to fluorophores. Detection is by microscopy, and is either subjective or by automatic evaluation. With enzyme-linked antibodies, a calorimetric reaction may be required. It will be appreciated that immunohistochemistry is often followed by counter-staining of the cell nuclei, using, for example, Hematoxyline or Giemsa stain.

The present invention also envisages a method for identifying candidate agonist or antagonist compounds of the RA-CD44 variant product comprising: providing a polypeptide comprising an amino acid sequence substantially as depicted in SEQ ID NO:2, or a fragment of such a sequence; contacting a tested candidate compound with said polypeptide; measuring the effect of said candidate compound on the activity of said polypeptide and selecting those compounds which show at least 70%, preferably 90%, reduction of the level or duration of said activity (antagonists) or at least 70%, preferably 90%, increase in the level or duration of said activity (agonists). Any assay measuring a known activity of CD44 may be used to test the effect of the candidate compound such as for example, cell adhesion, rolling, extravasation or migration of cells.

Wherein the candidate agonist is one that has an activity which is essentially identical to the activity of RA-CD44, the method for identifying it will comprise the following steps: providing a polypeptide comprising an amino acid sequence substantially as depicted in SEQ ID NO:2, or a fragment of such a sequence; measuring the activity of said polypeptide in a test assay; measuring the activity of said candidate compound in said test assay; comparing the above measured activities, wherein an activity measured for the candidate being at least 70%, preferably 90%, of the activity measured for the polypeptide indicating that said candidate compound is a compound having an activity which is essentially identical to the activity of the RA-CD44 variant product.

The test assay in the above methods may be any assay in which the activity of RA-CD44 may be measured such as for example, the assays measuring activities mentioned above.

The present invention also concerns compounds identified by the above methods

In accordance with yet another aspect of the invention, peptide ligands which bind to the RA-CD44 variant product of the invention are identified. The identification of such ligands may be carried out, for example, by using phage display peptide libraries. Methods involving use of such libraries are described, for example in Nissim A.; EMBO J., 13:692 (1994) The phage libraries used may be antibody libraries as well as peptide libraries.

Thus a method is provided for the identification of a peptide which binds to the RA-CD44 variant product comprising: incubating cells expressing the RA-CD44 variant product with a phage display peptide library; washing the cells to remove unbound phages; eluting bound phage from the cells; amplifying the resulting bound phage; determining the display peptide sequence of the bound phage.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning and Expression of CD44-RA Variant Generation of Antibodies there Against and Effect Thereof on Cell Migration and Arthritis Progression Materials and Experimental Procedures Cloning and transfection of human CD44vRA, CD44v3-10 and CD44s—For cloning human CD44vRA cDNA, the total synovial fluid cell population of RA patients undergoing joint aspiration was isolated. RNA was separated with a commercial kit (Promega, Madison, Wis.), CD44vRA cDNA was prepared by RT-PCR (PTC-100™ Programmable Thermal Controller, MJ Research, Watertown, Mass.), using the following primers representing the constant coding regions of CD44 (FIG. 1A):

Ex1-sense,
(SEQ ID NO:7)
5'-GAATTCGCCG CCACCATGGA CAAGTTTTGG TGG-3';

Ex19-antisense,
(SEQ ID NO:8)
5'-TCTAGATTAC ACCCCAATCT TCATG-3;

PCR product size was confirmed by agarose gel electrophoresis and sequencing (ABI PRISM 310, Perkin-Elmer, Wellesley, Mass.) and PstI (New England BioLabs, Beverly, Mass.) digestion (the nucleotide insertion in CD44vRA introduces a PstI digestion site).

The PCR product was excised from the gel, purified and subcloned into a pGEM vector (Promega). Positive clones were selected by white/blue screening. Plasmids were purified with a commercial kit (Promega), subjected in EcoRI/XbaI-double digestion and cloned into the pcDNA3.1 vector (Invitrogen, Paisley, UK) in which the gene product was expressed. The plasmid was transfected into the CD44-negative Namalwa Burkett lymphoma cell line (ATCC, Manassas, Va., ATCC No: CRL-1432) as described [Zhang Z et al. *J. Biol. Chem.* 276:41921-42929 (2001)]. For cloning of human CD44v3-10, RNA was isolated from human keratinocytes (Hadassah University Hospital, Jerusalem), and for cloning of human CD44s, RNA was isolated from the HeLa cervical cancer cell line (obtained from ATCC, Manassas, Va., ATCC No: CCL-2), using the above-described protocol. Transfection of CD44v3-v10 and CD44s cDNAs as well as of the pcDNA3.1 vector ("empty vector") was performed as described above. Accordingly, the transfected Namalwa cells were designated Namalwa-CD44vRA, Namalwa-CD44v3-v10, Namalwa-CD44s and Namalwa-Neo (empty), respectively.

Preparation of soluble hCD44v3-10, hCD44vRA and hCD44s plasmids—The soluble CD44v3-10 cDNA was cloned from total RNA of primary human keratinocyte by RT-PCR amplification, using two primers assigned from the published CD44 sequence;

Ex1s:
(SEQ ID NO:9)
5'-TATCTAGAGC CGCCACCATG GACAAGTTTT GGTGG-3'

Ex16/17as:
(SEQ ID NO:10)
5'-TATCTAGAGCC ATTCTGGAAT TTGGGGTGT-3'

Both primers contained a XbaI recognition site. The PCR products were digested with XbaI enzyme and pCXFc zeovector was digested with NheI enzyme. After digestion, the PCR products were ligated into the pCXFc zeovector to generate CD44v3-v10-immunoglobulin (Ig)-Fc recombinant. Using the same protocol, the soluble CD44vRA and soluble CD44s cDNAs were cloned from synovial cells of rheumatoid arthritis patients. The soluble CD44 fragments were assigned from the published sequence of CD44 (1-1824 bases) [Screaton, G. R., et al., (1992) ibid.].

Transient transfection of the soluble CD44 plasmids into 293T cells—A quantity of 3 µg of each one of the above-indicated Fc containing plasmids was incubated for 20 min with 12 µl of FuGene (Roche). The mixture was added into 15 cm cell plates containing 70% confluent 293T cells. Supernatant was collected after 48 h and 72 h. The CD44-Ig Fc fragmented proteoglycans were purified on protein-G column and analyzed for their accurate size by SDS-PAGE and immunoblotting with anti-pan-CD44 mAb (Hermes-3, ATCC Manassas, Va., ATCC No: HB-9480).

Reverse transcriptase-polymerase chain reaction (RT-PCR)—RNA was extracted from synovial fluid cells of RA patients, primary human keratinocytes or Namalwa-CD44vRA cells, using RNA-BEE reagent (RNA isolation solvent, Tel-Test Inc., Friendswood, Tex.) according to the manufacturer's instructions. Reverse transcription was performed with 5 units of AMV reverse transcriptase (Promega, Medison, Wis.) in a 20 µl reaction volume containing 50 mM Tris-HCl, pH 8.3, 50 mM KCL, 10 mM $MgCl_2$, 10 mM dithiothreitol (DTT) and 20 units RNasin (Promega, Medison, Wis.), using 500 ng of RNA and 100 ng of oligo d(T)18 primer (Promega, Medison, Wis.). Reaction samples were incubated for 1 hour at 41° C. and then the reverse transcriptase was inactivated by heating the mixture for 10 minutes at 65° C. The amplification was performed in a microprocessor-controlled incubator (MiniCycler™, MJ Research, Watertown, Mass.), using 0.5 µl of the reverse transcriptase reaction product (cDNA) in a final volume of 50 µl containing 50 mM KCl, 1.5 mM $MgCl_2$, 10 mM Tris-HCl, pH 9.0, 250 µM dNTPs and 2.5 units Taq DNA polymerase (Promega, Medison, Wis.). The following primers (FIG. 1A) were added to reaction mixture:

```
hs5' sense:
5'-GATGGAGAAAGCTCTGAGCATC-3';    (SEQ ID NO:11)

pv3I sense:
5'-ACGTCTTCAAATACCATCTC-3';      (SEQ ID NO:12)

hs3' anti-sense:
5'-TTTGCTCCACCTTCTTGACTCC-3';    (SEQ ID NO:13)
```

The CD44 amplification was carried out for 30 cycles with denaturation at 94° C. for 1 minute, annealing at 50° C. for 1 minute and extension at 72° C. for 2 minutes, followed by 10 minutes final extension at 72° C. The amplified products were resolved on 1.5% agarose gel. Determination of the cellular CD44 isoform transcripts was based on the position of the band in relation to the markers' ladder, and on the expected bp size of the different CD44 variants.

Generation of monoclonal antibody secreting Hybridomas—Thirty mer CD44vRA peptide: SNPEVLLQTT TRMTADVDRNGTTAYEGNWN (SEQ ID NO:14) obtained from Corixa (Seattle, Wash.), and/or 100 µg/ml soluble CD44vRA produced as described above, both emulsified in complete Freund's adjuvant (CFA) (Sigma), were used to immunize subcutaneously or intramuscularly 8-week-old female C75BL/6 mice. The immunization was repeated on days 14 and 28 and two weeks later the mice were bled and their sera were tested by flow cytometry for their ability to bind to Namalwa cells expressing CD44. The animals with highest polyclonal anti-CD44 antibody titers were selected and boosted intraperitoneally (i.p.) with $10^8$ Namalwa-CD44vRA cells. After 72 h, spleen cells from the mice were harvested and fused with SP 2/0 myeloma cells according to Kohler and Milstein [Kohler, G., and Milstein C. Nature 256:495-497 (1975)]. After one day of incubation in enriched RPMI 1640 (Sigma) containing L-glutamine, penicillin-streptomycin solution, sodium pyruvate and MEM-eagle non-essential amino acids (Biological Industries Ltd., Israel) and 20% fetal bovine serum (FBS) (Sigma), the hybridomas were grown in ClonaCell™-HY Hybridoma Selection Medium (medium D, StemCell Technologies Inc.). Between days 10 to 14, isolated hybridoma colonies were collected from the semi-solid agar and grown in 96-well plates (Costar) in enriched RPMI 1640 medium containing HAT media supplement (Sigma) and 20% of FBS. At day 7 after plating, the supernatants from isolated hybridoma clones were screened by flow cytometry for their ability to bind to Namalwa-Neo, Namalwa-CD44v3-10 or Namalwa-CD44vRA cells. Hybridoma whose supernatants bound selectively or preferentially to Namalwa-CD44vRA were cloned by limiting dilution and then re-cloned for additional three cycles. The isolated hybridoma were maintained in enriched RPMI 1640 containing HAT media supplement and 20% FBS. The isotype of the CD44vRA-positive hybridoma supernatant was determined by ELISA using Clonotype System-HRP (Southern Biotechnology Associates, Inc.).

Fluorescence activated cell sorting (FACS) analysis—A quantity of $10^6$ cells were incubated with 3G5 anti-pan-CD44s (Hermes 3, IgG1) F-10-44-2 anti-pan-CD44 mAb (IgG2b, Serotec, Oxford, UK, known also as anti-CD44s mAb) or VFF7 anti-CD44v6 mAb (IgG1, Bender MedSystem, Vienna, Austria) for 45 min on ice. After extensive washing, the cells were incubated with fluorescein isothiocyanate (FITC)-conjugated secondary anti-Ig antibody (Jackson ImmunoResearch, West Grove, Pa.) for 30 min on ice. The cells were then washed and analyzed with a Flow Cytometer (Beckton Dickinson, San Jose, Calif.).

RF analysis—Was effected using ELISA commercial kit: mouse rheumatoid factor cat. no. 6200 of Wirostats Inc., USA according to Manufacturer instructions.

Enzyme-linked immunosorbent assay (ELISA)—Polystyrene plates of 96 wells (Nunc) were coated with purified CD44vRA-IgFc, CD44v3-v10-IgFc, CD44s-IgFc soluble proteins or with BSA (100 µg/ml per well diluted in 100 µl sodium acetate buffer, pH 7.0). After overnight incubation at 4° C., the plates were washed three times with phosphate-buffered saline (PBS), pH 7.4, containing 0.05% Tween 20 (PBS/T). Following blocking with 10% milk in PBS at 37° C. for 2 h, different concentrations of F8:33 anti-CD44vRA mAb or anti-pan-CD44 (Hermes 3) mAb were added to the wells. The plates were incubated at 37° C. for 1 h, washed and a secondary goat anti-mouse polyvalent peroxidase-conjugated antibody (Jackson ImmunoResearch) was added for an additional 1 h. The enzyme reaction was developed with 0.04% $H_2O_2$ and 0.04% O-phenylenediamine in phosphate-citrate buffer, pH 5.0. The optical density was measured at 405 nm on a microplate reader MRX (Dynatech Laboratories) and values above 0.100 were considered positive.

Western Blot analysis—Cells were lysed in NP-40 buffer and 100 µg of proteins were run on denaturing SDS-PAGE and transferred to a PVDF membrane (Millipore, Bedford, Mass.). Blots were blocked with 1% BSA in PBS containing 0.1% Tween-20 (PBS-T), and incubated for 1 h with 1 µg/ml Hermes-3 anti-pan-CD44 mAb, which was obtained from the ATCC hybridoma (ATCC No: HB-9480) supernatant and purified on a protein-G column. The blots were rewashed in PBS-T, incubated with the appropriate HRP-conjugated anti-Ig secondary antibody (1:10,000 dilution) (Jackson ImmunoResearch) for 45 min, rewashed in PBS-T and developed with ECL reagent (Amersham Biosciences, Buckinghamshire, UK).

Transwell migration assay—Migration assays were performed in transwell plates (Costar, Cambridge, Mass.) of 6.5 mm diameter. The upper and lower compartments of the transwells were separated by a 5 µM pore polycarbonate filter coated overnight at 4° C. with 0.5 mg/ml hyaluronic acid (HA; H1876, Sigma) in PBS, and then washed 3 times with RPMI 1640. A quantity of $5 \times 10^5$ transfected Namalwa cells or human primary keratinocytes suspended in RPMI 1640 was added to the upper compartment and 293 T cell supernatant diluted in RPMI or stromal cell-derived factor-1 (SDF-1) (400 ng/ml diluted in RPMI; R&D systems) was added to the lower compartment. To evaluate the anti-migratory capacity of the antibody, F8:33 anti-CD44vRA mAb or anti-pan-CD44 (F10-44-2) mAb was added, in different concentrations, to the transwell plates, which were then incubated at 37° C. with 5% $CO_2$ for 4 hours. Cells that migrated to the lower compartment were counted at the end of the incubation period by fluorescence-activated cell sorter (FACS; Becton Dickinson, San Jose Calif.) on high speed for one minute and values of cell number/min were recorded.

Inhibition of Collagen-induced arthritis in mice—The following mAbs were used: rat anti-mouse CD44 constant region (rat, IgG2b) obtained from hybridoma KM81 (ATCC, TIB-241; 22); rat anti-mouse cell surface immunoglobulin idiotype (rat, IgG2b) obtained from hybridoma 4D2 (provided by J. Haimovich, Tel-Aviv University, Maloney et. al., Hybridoma 4:191-209, 1985) was used as an irrelevant isotype control for KM81 mAb; mouse anti-human CD44vRA (mouse, IgG2a) obtained from hybridoma F8:33 (our developed hybridoma); mouse anti-human CD44 constant region (mouse, IgG2a) obtained from hybridoma F10-44-2 (was purchase from Serotec Company) was used as a non-biofunctional isotype control for F8:33 mAb.

In order to induce arthritis in mice, Male DBA/1 mice (8-12 weeks old) were injected intradermally at the base of the tail with 200 μg type II collagen purified from bovine articular cartilage and emulsified in complete Freund's adjuvant (CFA; Difco Laboratories, Detroit, Mich., USA) as described in Williams et. al., Proc. Natl. Acad. Sci. USA 89:9784-9788, 1992. The mice received a booster injection of 200 μg type II collagen emulsified in CFA, 3 weeks after the first dose. The mice were inspected daily and each animal with erythema and/or swelling in one or more limbs was randomly assigned to one of 4 groups, which received intraperitoneal (i.p.) injections of KM81 anti-mouse CD44 mAb, 4D2 isotype matched control mAb, F8:33 anti-human CD44vRA mAb or F10-44-2 non-biofunctional isotype control anti-human CD44 mAb. Each mouse was injected on the day of disease onset (day 0) and then every other day for 10 days with 200 μg antibody in 100 μl PBS. Arthritis was monitored over the 10 days treatment period by measuring paw swelling. In order to measure paw swelling, the thickness of each affected hind paw was measured with microcalipers. The results are expressed as a direct measure of paw width in millimeters.

Statistical analysis—Data were analyzed using microcomputer programs for one-way ANOVA, followed by Student's t-test for unpaired values. $P<0.05$ was considered significant. The results are expressed as the mean±s.e.m. Each experiment was repeated at least 3 times, all showing similar results.

Example 1 mRNA of CD44 Expressed on Synovial Fluid Cells of Rheumatoid Arthritis (RA) Patients Contains an Intron-Derived Extra Trinucleotide Synovial fluid cells from RA patients were isolated following joint aspiration. Their total RNA was reverse transcribed and subjected to PCR, using primers representing the constant coding regions of CD44.

FIG. 1B shows the RT-PCR of synovial fluid cells derived from the joint of representative RA patients. Two major signals were detected: a fast-migrating band (571 bp) corresponds to CD44s, and a slow-migrating band (1714 bp) corresponds to CD44v3-v10, which is also expressed on keratinocytes. These findings were confirmed by direct sequencing (data not shown).

A CD44 variant was detected in synovial fluid cells derived from 52 of 55 RA patients and from 12 of 14 patients with psoriatic arthritis (PSA). Five of 12 samples from synovial fluid cells of osteoarthritis (OA) patients also displayed the CD44 variant.

The CD44 variant RT-PCR products from 29 of 55 RA patients and 8 of 14 PSO patients were sequenced. An extra trinucleotide (CAG) was detected between exon v4 and exon v5 (FIG. 1C) in 23 (of 29) RA patients and 7 (of 8) PSA patients following computerized alignment versus the wild type variant-CD44v3-v10 (FIG. 1C). The CAG trinucleotide was transcribed from the extreme end of the intron bridging exon v4 to exon v5, precisely at the splicing junction. This trinucleotide allows the translation of alanine (Ala) without interfering with the entire reading frame of CD44 transcript. Rheumatoid arthritis-derived CD44 variant with extra CAG was designated CD44vRA.

Example 2

Production of Anti-CD44vRA mAb

Expression of extra Ala in CD44vRA appeared to induce a configuration change, allowing the generation of mAbs able to discriminate between the RA variant and the wild-type isoform-CD44v3-v10 (or the standard isoform CD44s). CD44vRA, CD44v3-v10 (derived from human keratinocytes) and CD44s (derived from HeLa cells) cDNAs were transfected into CD44-negative Namalwa Burkett lymphoma cell line. CD44 transfectants expressing high levels of CD44s, as well as CD44v3-v10 and CD44vRA transfectants expressing equal levels of v6-containing CD44 variant were selected (FIG. 2A). The transfectants were designated Namalwa-CD44s, Namalwa-CD44v3-v10 and Namalwa-CD44vRA, respectively. Namalwa cells transfected with an empty vector were designated Namalwa-Neo.

C57BL/6 mice were immunized with soluble CD44vRA, incorporated into CFA and challenged with Namalwa-CD44vRA cells as described in Materials and Methods. Splenocytes from mice showing polyclonal anti-CD4vRA antibodies in their serum were fused with SP2/0 myeloma cells. Hybridoma cell clones were selected according to the ability of their supernatants to bind to Namalwa-CD44vRA, but substantially not to Namalwa-CD44v3-v10, Namalwa-CD44s or to Namalwa-Neo, as indicated by flow cytometry. Clones and sub-clones were established from positive hybridoma cell colonies, and they were stable in culture for over 8 months. Anti-CD44vRA mAbs from supernatants of positive hybridomas, designated F8:33, were purified on G protein column. Flow cytometry further revealed (FIG. 2B) that at a concentration of 0.4 μg/ml, F8:33 anti-CD44vRA mAb interacted with Namalwa-CD44vRA, but not with the other transfectants, including the wild type-CD44v3-v10. At a concentration of 2 μg/ml or higher (Table 1) F8:33 cross-reacted with Namalwa-CD44v3-v10 (FIG. 2B) and at even higher concentrations (>100 μg/ml)—with Namalwa-CD44s and Namalwa-Neo cells as well (not shown).

TABLE 1

Binding of F8:33 anti-CD44vRA mAb to Cells

| F8:33 mAb Concentration | Namalwa-CD44vRA | Namalwa-CD44v3-10 | RA synovial fluid cells | Human Keratinocytes |
|---|---|---|---|---|
| 0.2 µg/ml | + | − | + | − |
| 0.4 µg/ml | + | − | + | − |
| 2 µg/ml | + | + | + | − |
| 4 µg/ml | + | + | + | − |
| 20 µg/ml | + | + | + | − |
| 40 µg/ml | + | + | + | − |
| 100 µg/ml | + | + | + | − |
| 200 µg/ml | + | + | + | + |

+ binding;
− no binding;
N.D. not done

The above findings were confirmed by ELISA showing that F8:33 mAb bound, in a dose-dependent manner, to CD44vRA-coated microwells at higher rates than to CD44v3-v10 or CD44s-coated microwells (FIG. 3A). In contrast, anti-pan CD44 mAb bound to a similar extent to CD44vRA and CD44v3-v10 (FIG. 3B), while it did not bind to CD44s, presumably due to its inability to recognize the relevant epitope. The identity of the soluble CD44 proteins was verified by Western Blot (FIG. 3C).

The antibodies bound to CD44vRA coated on microwells or expressed on Namalwa cells at higher rates than to the corresponding wild type molecule-CD44v3-v10 or to CD44s. Notably, CD44vRA and CD44v3-v10 are expressed to a similar extent on Namalwa cells, while CD44s is expressed on these cells at an even higher level, indicating that the preferential binding of F8:33 to Namalwa-CD44vRA is not quantitatively dictated. The selective binding of F8:33 anti-CD44vRA mAb to Namalwa-CD44vRA was detected at concentrations equal to or lower than 0.4 µg/ml. At increasing concentrations, F8:33 first cross-reacts with Namalwa-CD44v3-v10 and then with Namalwa-CD44s, implying differential binding affinity, the highest to cell surface CD44vRA and the lowest to cell surface CD44s.

Example 3

Selective Targeting of RA Synovial Fluid Cells by F8:33 Anti-CD44vRA mAb

The Namalwa transfectants are, in fact, an artificial model for evaluating the binding capacity and bioactivity of anti-CD44vRA mAbs. To obtain a more realistic assessment, the interaction of F8:33 with primary RA synoviocytes and primary keratinocytes was examined. Keratinocytes were chosen as a reference group, because they are known expressors of CD44v3-v10, the wild type counterpart of CD44vRA. Flow cytometry analysis revealed slightly higher expression of CD44s on synovial fluid cells of an RA patient than on keratinocytes derived from two donors, with variations in expression of v6-containing CD44. It was also noted that keratinocytes expressed v9-containing CD44 molecules (in which CD44v3-v10 is included) at much higher levels than RA synoviocytes (FIG. 4A). Even so, at concentrations of 2 and 4 µg/ml, F8:33 anti-CD44vRA mAb interacted with synovial fluid cells, but not with keratinocytes as indicated by flow cytometry (FIG. 4B). Even at as high a concentration as 100 µg/ml, F8:33 selectively bound to RA synoviocytes, while at a concentration of 200 µg/ml F8:33 cross-reacted with keratinocytes (Table 1). Synovial fluid cells were identified as CD44vRA-positive cells by PstI digestion of their cDNA. Keratinocytes constitutively express CD44v3-v10.

Example 4

The CD44vRA-Dependence of Transwell Cell Migration

The question whether the interaction between F8:33 anti-CD44vRA mAb and RA synovial fluid cells displays a bioactivity was investigated. To this end, the ability of F8:33 anti-CD44vRA to inhibit the migration of Namalwa transfectants as well as RA synovial fluid cells and keratinocytes in transwell migration assay was determined.

F8:33 anti-CD44vRA reduced, in a dose-dependent manner, the ability of Namalwa-CD44vRA cells to cross the HA-coated membrane more effectively than that of Namalwa-CD44v3-v10 (FIG. 5A). This antibody could not display any inhibitory effect on the migration of Namalwa-CD44s and Namalwa-Neo cells (at a concentration of 1 µg/ml, F8:33 enhanced the migration of Namalwa-Neo cells). Isotype-matched anti-pan-CD44 mAb (recognizing a constant epitope on all CD44 isoforms) slightly influenced, at the highest concentration only, the migration of all CD44 transfectants (FIG. 5B), implying the selective anti-migratory effect of F8:33.

F8:33 anti-CD44vRA mAb also reduced, in a dose-dependent manner, the ability of CD44vRA-positive RA synovial fluid cells, but not keratinocytes, to cross the HA-coated membrane as indicated by transwell migration assay (FIG. 6A). In contrast, the anti-pan-CD44 mAb did not interfere with the cell migration of both cell types (FIG. 6B).

F8:33-6-10-8 is also highly specific for the CD44vRA product (FIG. 7A-7E). Antibodies derived from the F8:33-6-10-8 hybridoma were incubated with Namalwa cells expressing empty vector (Namalwa-pcDNA3.1), standard CD44 (Namalwa-CD44std.), CD44v3-v10 product (Namalwa-CD44v3-v10) or CD44vRA product (Namalwa-CD44vRA). Already at a concentration of 1.2 µg/ml (FIG. 7D), the F8:33-6-10-8 antibodies react specifically with the CD44vRA expressing cells, whereas they do not bind to the other cells. Even at a concentration of 1.2 mg/ml (FIG. 7A), the F8:33-6-10-8 antibodies bind to the CD44vRA-expressing cells with a higher affinity than to the other cells.

Example 5

Inhibition of Collagen-Induced Arthritis in Mice

The anti-CD44vRA, F8:33 mAb was tested in the mouse in vivo assay of collagen-induced arthritis (CIA). Collagen-induced arthritis (CIA) is the animal analogue of rheumatoid arthritis (RA), a recurrent, systemic disease characterized by chronic inflammation within the joints, associated with synovitis and erosion of cartilage and bone.

As can be seen in FIG. 8, Collagen-induced arthritis (CIA) is inhibited by treatment with the anti-CD44vRA mAb F8:33, as indicated by reduction in paw swelling. In contrast, the control antibody, anti-pan human CD44 monoclonal antibody F 10-44-2, was not able to reduce the arthritic activity.

As a positive control, KM81, anti-pan mouse CD44 antibody was used (FIG. 9). This antibody was also able to reduce paw swelling caused by CIA. In contrast, 4D2 monoclonal antibody, a mouse isotype-matched unrelated mAb, which was used as a negative control, did not change the course of CIA.

To summarize, F8:33 shows of in vivo biological activity, as indicated by its ability to reduce arthritic activity in mice.

Example 6

Expression Analysis of CDvRA

Figure 10:
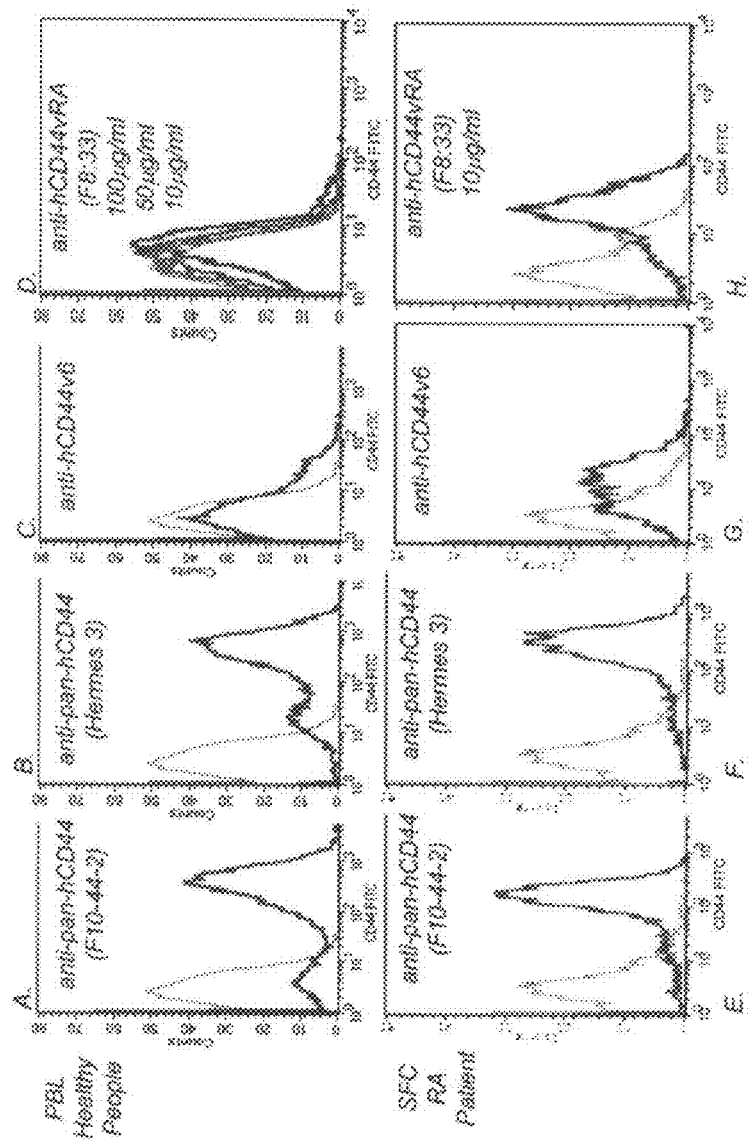

Expression of CDvRA in PBLs was analyzed as follows.
Materials and Experimental Procedures
Flow cytometry analysis of F8:33 anti-CD44vRA mAb binding to PBL of healthy individuals—Peripheral white blood cells of 62 healthy donors were isolated by a Ficoll gradient and analyzed by flow cytometry, using commercial anti-human-pan-CD44 mAbs (Hermes 3 and F10-44-2) and anti-human CD44v6 mAb, as well as F8:33 anti-CD44vRA, as described above.
RT-PCR—Effected as described above.
Results
PBLs from healthy donors express only the standard CD44 (CD44s), as indicated by their immunostaining with Hermes 3 and F10-44-2 (FIG. 10 A-B). Anti-human v6 mAb did not bind to the normal PBL (FIG. 10C), indicating that these cells do not express v6-containing CD44 variants. Furthermore, F8:33 did not bind to normal PBL, even at the highest concentration (100 μg/ml; FIG. 10D) used. Synovial fluid cells from RA patients served as positive control for immunostaining with F8:33. FIGS. 10E-H clearly shows similar expression of CD44 on both normal PBLs and RA synovial fluid cells, as indicated by staining with anti-human-pan-CD44 mAbs. Further, RA synovial fluid cells (but not normal PBLs) express CD44v6, as indicated by staining with anti-human CD44v6 mAb (FIG. 10G). F8:33 anti-CD44vRA mAb bound exclusively to the synovial fluid cells of RA patients (FIG. 10H).

The above described FACS results were further substantiated by RT-PCR analysis. As shown in FIGS. 11A-C, only CD44s transcripts were detected in normal PBLs (representative results from 12 healthy individuals are shown in FIG. 11A). In contrast, the mRNA of RA synovial fluid cells (6 representative samples) contained the expected CD44s, as shown when primers from the constant regions were used (FIG. 11B) and a CD44 variant of CD44vRA size, as shown when primers from variant regions were used (FIG. 11C).

In conclusion, CD44vRA was detected on synovial fluid cells of RA patients (in about 80% of the 49 patients examined) and to a lower extent (only 10%) on the PBLs of these patients. CD44vRA was not detected on the PBLs of healthy individuals. Cumulatively, these findings suggest that the expression of CD44vRA is confined to the inflammation site.

Example 7

Therapeutic Effect of F8:33 Anti-Human CDvRA

Experimental Procedures
As stated above, CIA is considered an animal model of human RA. The joint inflammatory disease was induced by two subcutaneous (s.c.) injections (into the base of the tail) of type II collagen at three week intervals. Joint inflammation, which appears several days after the last collagen injection, causes enhanced foot pad swelling, as well as swelling of other joints. The thickness of nonarthritic footpads is 1.5 to 1.7 mm. A footpad thickness of 1.9 to 2.0 mm was arbitrarily set as disease onset. Footpad thickness gradually increased, reaching a plateau at day 8. Antibodies (200 μg per injection) were injected at disease onset and then every other day for 12 days. The antibody effect on footpad thickness was determined by a double blind assay, using an electronic microcaliper to measure the thickness of the joints. The mice were bled prior to disease induction, following disease onset and upon termination of the experiment (around day 12). The sera were stored and later analyzed for the presence of rheumatoid factor (RF). The mice were sacrificed upon termination of the experiment and joints were removed from some of the animals for histopathological examination, immunohistochemical staining and RT-PCR analysis.

Results
The results of the clinical experiment, which included 3 groups, 10 mice in each group, were recorded and shown in FIG. 12. As shown, injection of KM81 anti-mouse-pan-CD44 mAb (positive control), which recognizes the constant CD44 epitope, markedly reduced arthritic inflammatory joint swelling in the DBA/1 mice, as previously shown by the present inventors (J. Autoimmun. 13, 39-47, 1999). Injection of F8:33 anti-human CD44vRA mAb also reduced the arthritic activity in the DBA/1 mice, albeit slightly less than KM81 (the difference was, however, insignificant). Injection of isotype-matched control antibodies (negative control: 4D2 served as control for KM81, F10-44-2 served as control for F8:33) did not influence the course of the disease in the DBA/1 mice.

In conclusion, anti-CD44vRA, F8:33 antibody, reduced joint inflammation by almost 80% when compared with the negative control group. Its effect was close to that of the KM81 anti-mouse mAb (positive control), showing its efficient bioactivity.

The above-described clinical results were further substantiated by histopathological examinations. The rear footpad joints of 2 arthritic mice treated with isotype-matched control mAb (negative control), 2 arthritic mice treated with KM-81 anti-mouse-pan CD44 mAb (positive control) and 2 arthritic mice treated with F8:33 anti-human-CD44vRA mAb, were histopathologically examined (Patho-Lab, Kiryat Weizmann, Rehovot). The pathological report (not shown) confirmed the clinical findings described here in above and in FIG. 13. The mouse joints from arthritic mice treated with KM81 and F8:33 recovered, at least partly, when compared with joints from arthritic mice treated with isotype-matched control mAbs (negative control).

Flow cytometry analysis of F8:33 binding to spleen cells from arthritic and nonarthritic mice. As is evident from FIG. 5, F8:33 bound to spleen cells from arthritic mice, but not to spleen cells from nonarthritic mice, whereas anti-human-pan CD44 mAb (Hermes 3) and anti-mouse pan-CD44 mAb (KM81) bound to both cell types. Anti-mouse-CD44v6 mAb showed marginal binding to arthritic cells, but did not bind to nonarthritic cells (FIG. 5). In the context of these findings it should be stressed that arthritic splenocytes express both CD44s and v6-containing CD44 variants, as indicated by FACS analysis and RT-FCR, whereas nonarthritic splenocytes express standard CD44 only. The above results suggest that F8:33 exclusively identifies and binds to spleen cells of arthritic mice.

The ability of F8:33 to induce apoptosis of spleen cells was then determined. For this purpose, a two-dimensional flow cytometry immunostaining with annexin V and propidium iodide was effected. The findings shown in FIGS. 14A-D exhibit a correlation between the ability of increasing concentrations of F8:33 to bind to arthritic splenocytes (FIGS. 11 and 12) and their ability to induce apoptosis (FIGS. 14A-D). Furthermore, F8:33 induced apoptosis (FIG. 14A) or decreased survival (FIG. 14B) of arthritic splenocytes (from mice with CIA), but not of nonarthritic splenocytes (FIGS. 14C and D). In contrast, anti-pan-CD44 mAbs (directed against either human or mouse CD44) did induce apoptosis or even protected the splenocytes from apoptosis (see FIG. 14C). In conclusion, F8:33 anti-CD44vRA mAb shows in vitro bioactivity, as implied by its ability to induce apoptosis selectively in arthritic splenocytes. In contrast, anti-pan-CD44 mAbs does not exhibit such selectivity.

The expression of Rheumatoid Factor (RF) was then analyzed as follows. Randomly selected mice from the different treatment groups were bled prior to disease induction with collagen (FIG. 15, bars marked by 1), two days following onset of disease (or the first day of antibody treatment) (FIG. 15, bars marked by 2), as well as 14 days following disease onset, i.e., upon termination of the experiment (FIG. 15, bars marked by 3). The sera were analyzed, using a commercial kit, for RF levels, an accepted assay for human RA diagnosis. The findings confirmed the clinical data relating to footpad swelling, as shown in FIG. 12 and the histopathological analysis. Thus, injection of F8:33 anti-human CD44vRA mAb or KM81-anti-mouse-pan CD44 mAb reverted or preserved the preimmunization levels of RF detected in the sera before treatment with the antibody. After injection of isotype-matched control mAbs the levels of RF were enhanced (FIG. 15).

The above-described clinical results were validated at various kinetics and doses of F8:33 and the therapeutic efficacy of the antibody was compared to that of a known anti-RA drug, anti-human TNF mAb (Ramicade).

43 mice included in this experiment were divided into 5 experimental groups and the results were recorded (FIG. 16). Systemic injection (starting at CIA onset) of anti-mouse TNFα mAb (5 mice) or anti-human TNFα mAb (3 mice), adhering to the standard protocol (i.e., 200 μg antibody/mouse every other day for 12 days) markedly reduced the CIA activity in DBA/1 mice (total, 8 mice), as indicated by tracing footpad swelling. Systemic injection of F8:33 anti-CD44vRA mAb according to the standard protocol (i.e., first injection at disease onset) substantially reduced the CIA activity in the DBA/1 mice (9 mice, F8:33 200 μg), confirming the above-described clinical findings (FIG. 12). Systemic injection of 70 μg per dose of F8:33, instead of 200 μg per dose, did not influence the course of CIA in the DBA/1 mice (9 mice, F8:33 70 μg). Systemic injection of F8:33, starting at full blown CIA, rather than at disease onset, reduced joint inflammation in the DBA/1 mice (7 mice; F8:33 200 μg per dose), albeit at a later phase of the disease. Furthermore, on day 12 identical reduction of inflammation was recorded for both groups of mice. Systemic injection of 4D2 isotype-matched control mAb for KM81 (5 mice) and F10-44-2 isotype-matched control anti-pan-CD44 mAb for F8:33 (5 mice) did not influence the course of CIA in the DBA/1 mice.

In conclusion, F8:33 anti-CD44vRA was as effective as anti-TNFα mAb. Furthermore, this antibody reduced CIA activity even when injected almost at the peak of the joint inflammatory response. Finally, it should be noted that the therapeutic dose of F8:33 (200 μg per injection) is equivalent to the therapeutic dose of Remicade in RA patients (10 mg/kg).

The RF level in sera of of mice tested as shown in FIG. 16 was determined. As shown in FIG. 17, F8:33, anti-mouse TNFα and Remicade (bars marked by 3) caused the RF to revert to the pre-immunization levels detected in the sera of the individual mice before treatment with the antibody (bars marked by 1), whereas isotype-matched control mAb (anti-human CD44 mAb) did not affect the enhanced levels of RF detected shortly after disease onset (bars marked by 2), thus substantiating the clinical data.

The therapeutic effect of F8:33 was challenged in a different mouse model, which enables, unlike the conventional CIA model, the synchronized appearance of arthritis and the unlimited use of all mouse strains. In this experiment BALB/c mice were subjected to a cocktail of four different anti-collagen monoclonal antibodies and two days later they were inoculated i.p. with LPS. The mice simultaneously developed arthritis, as indicated by footpad swelling. Injection of F8:33 after disease onset (5 mice) significantly reduced the arthritic inflammation when compared with that in mice that received PBS (4 mice, data not shown).

Example 8

Cloning of the heavy ($V_H$) and light ($V_L$) chains of F8:33, F8:33-6-8-10 and MF1-16-11 murine mAbs The CDRs of F8:33, F8:33-6-8-10 and MF1-16-11 murine mAbs were cloned and sequenced.

Experimental Procedures

Approximately 1-2 million mAb-secreting hybridoma cells were collected and total RNA was isolated using RNA-sol kit according to the manufacturer's instructions (BioLab). cDNA was produced by reverse transcription, using RNA template, an 18 base oligo-dT primer and SuperScript II reverse transcriptase (Invitrogen). Reaction samples were incubated at 42° C. for 1 hour. The resulting cDNA was used as a template for PCR amplification using Taq polymerase (Invitrogen) and mix of various 5' and 3' primers (Pharmacia Biotec) specific for murine VH and VL genes. PCR reaction samples were incubated at 94° C. for 2 min followed by 30 cycles of 94° C. for 1 min, 56° C. for 1 min and 72° C. for 2 min. A final extension at 72° C. for 10 min completed the reactions. Approximately 1 to 5 μg of the PCR products were resolved on 1% agarose gels and stained with ethidium bromide. PCR products of the appropriate size (300-350 base pairs) were inserted into the Invitrogen pCR2.1-TOPO-TA™ vector and transformed into IHV αF1 *E. coli* bacterial cells, according to the manufacturer's instructions. Colonies containing the plasmid with insert were selected by overnight growth, at 37° C. on Luria-Bertani agar plates containing ampicillin (100 μg/ml) and X-gal (80 μg/ml). White (positive) colonies were incubated over night under shaking at 37° C. in 5 ml of Luria-Bertani broth containing ampicillin (100 μg/ml) and plasmids were isolated using QIAprep Spin Miniprep DNA isolation kits, according to the manufacturer's instructions (QIAGEN). EcoRI digestion of 1 to 5 μg of the resulting plasmids and resolution of the products by agarose gel electrophoresis, as described above, confirmed the presence of the appropriate size inserts. 1 to 5 putative positive clones were sequenced with T7 (5'-TAA TAC GAC TCA CTA TAG GG-3', SEQ ID NO: 19) and M13Rev (5'-CAG GAA ACA GCT ATG AC-3', SEQ ID NO: 20) primers, using ABI Prism BigDye™ terminator cycle sequencing kits and ABI Prism 3100 Genetic Analyzer (Perkin Elmer). Consensus sequences were generated using the DNASTAR software suite (DNASTAR Inc.). GenBank Accession Numbers are AY605265 to AY605273 for $V_H$ sequences, and AY605274 to AY605282 for the $V_L$.

Identification of Ig germline sequences and assignment of relevant regions—Consensus nucleotide sequences were compared against the *Mus musculus* immunoglobulin (Ig) set database using IMGT/V-Quest (Lefranc, 2003; imgt.cines.fr/home.html). The sequences were concurrently compared against the *Mus musculus* Ig germline V-gene database using IgBlast (Aitschul et al., 1990; ncbi.nlm.nih.gov/igblast/). This allowed the identification of the complementary determining region (CDR) and framework (FR) regions of the $V_H$ and $V_L$ sequences, and provided numbering to the inferred amino acid sequences according to Kabat et al. (1991). Similarly, the IgBlast results allowed the identification of the most closely related murine Ig germline V-genes currently available in these databases. In all cases, the entire sequence, including those at the 5' end of each sequence imposed by the specific primers used in the original PCR amplification, were examined.

Results

Analysis of the $V_H$ and $V_L$ sequences of F8:33, F8:33-6-8-10 and MF1-16-11 murine mAbs is shown in FIGS. 18A-L.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

SEQUENCE LISTING

```
<160> NUMBER OF SEQ ID NOS: 44

<210> SEQ ID NO 1
<211> LENGTH: 2100
<212> TYPE: DNA
<213> ORGANISM: Homo sapiens

<400> SEQUENCE: 1
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt     120
cgctacagca tctctcggac ggaggccgct gacctctgca aggctttcaa tagcaccttg     180
cccacaatgg cccagatgga gaaagctctg agcatcggat ttgagacctg caggtatggg     240
ttcatagaag ggcacgtggt gattcccgg atccacccca actccatctg tgcagcaaac     300
aacacagggg tgtacatcct cacatccaac acctcccagt atgacacata ttgcttcaat     360
gcttcagctc cacctgaaga agattgtaca tcagtcacag acctgcccaa tgcctttgat     420
ggaccaatta ccataactat tgttaaccgt gatggcaccc gctatgtcca gaaggagaa     480 tacagaacga atcctgaaga catctacccc agcaacccta ctgatgatga cgtgagcagc     540
ggctcctcca gtgaaaggag cagcacttca ggaggttaca tcttttacac cttttctact     600
gtacacccca tcccagacga agacagtccc tggatcaccg acagcacaga cagaatccct     660
gctaccagta cgtcttcaaa taccatctca gcaggctggg agccaaatga agaaaatgaa     720
gatgaaagag acagacacct cagttttct ggatcaggca ttgatgatga tgaagatttt     780
atctccagca ccatttcaac cacaccacgg gcttttgacc acacaaaaca gaaccaggac     840
tggacccagt ggaacccaag ccattcaaat ccggaagtgc tacttcagac aaccacaagg     900
atgactgcag atgtagacag aaatggcacc actgcttatg aaggaaactg gaacccagaa     960
gcacaccctc ccctcattca ccatgagcat catgaggaag aagagacccc acattctaca    1020
agcacaatcc aggcaactcc tagtagtaca acggaagaaa cagctaccca gaaggaacag    1080
tggtttggca acagatggca tgagggatat cgccaaacac ccagagaaga ctcccattcg    1140
acaacaggga cagctgcagc ctcagctcat accagccatc caatgcaagg aaggacaaca    1200
ccaagcccag aggacagttc ctggactgat ttcttcaacc caatctcaca ccccatggga    1260
cgaggtcatc aagcaggaag aaggatggat atggactcca gtcatagtac aacgcttcag    1320
cctactgcaa atccaaacac aggtttggtg gaagatttgg acaggacagg acctctttca    1380
```

-continued

```
atgacaacgc agcagagtaa ttctcagagc ttctctacat cacatgaagg cttggaagaa    1440
gataaagacc atccaacaac ttctactctg acatcaagca ataggaatga tgtcacaggt    1500
ggaagaagag acccaaatca ttctgaaggc tcaactactt tactggaagg ttatacctct    1560
cattacccac acacgaagga aagcaggacc ttcatcccag tgacctcagc taagactggg    1620
tcctttggag ttactgcagt tactgttgga gattccaact ctaatgtcaa tcgttcctta    1680
tcaggagacc aagacacatt ccaccccagt gggggtccc ataccactca tggatctgaa     1740
tcagatggac actcacatgg gagtcaagaa ggtggagcaa acacaacctc tggtcctata    1800
aggacacccc aaattccaga atggctgatc atcttggcat ccctcttggc cttggctttg    1860
attcttgcag tttgcattgc agtcaacagt cgaagaaggt gtgggcagaa gaaaaagcta    1920
gtgatcaaca gtggcaatgg agctgtggag acagaaagc caagtggact caacggagag     1980
gccagcaagt ctcaggaaat ggtgcatttg gtgaacaagg agtcgtcaga aactccagac    2040
cagtttatga cagctgatga gacaaggaac ctgcagaatg tggacatgaa gattggggtg    2100
```

<210> SEQ ID NO 2
<211> LENGTH: 700
<212> TYPE: PRT
<213> ORGANISM: Homo sapiens

<400> SEQUENCE: 2

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
                20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
        50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Thr
    210                 215                 220

Ser Ser Asn Thr Ile Ser Ala Gly Trp Glu Pro Asn Glu Glu Asn Glu
225                 230                 235                 240

Asp Glu Arg Asp Arg His Leu Ser Phe Ser Gly Ser Gly Ile Asp Asp
```

```
                    245                 250                 255
Asp Glu Asp Phe Ile Ser Ser Thr Ile Ser Thr Thr Pro Arg Ala Phe
                260                 265                 270
Asp His Thr Lys Gln Asn Gln Asp Trp Thr Gln Trp Asn Pro Ser His
            275                 280                 285
Ser Asn Pro Glu Val Leu Leu Gln Thr Thr Thr Arg Met Thr Ala Asp
        290                 295                 300
Val Asp Arg Asn Gly Thr Thr Ala Tyr Glu Gly Asn Trp Asn Pro Glu
305                 310                 315                 320
Ala His Pro Pro Leu Ile His His Glu His His Glu Glu Glu Thr
                325                 330                 335
Pro His Ser Thr Ser Thr Ile Gln Ala Thr Pro Ser Ser Thr Thr Glu
                340                 345                 350
Glu Thr Ala Thr Gln Lys Glu Gln Trp Phe Gly Asn Arg Trp His Glu
            355                 360                 365
Gly Tyr Arg Gln Thr Pro Arg Glu Asp Ser His Ser Thr Thr Gly Thr
        370                 375                 380
Ala Ala Ala Ser Ala His Thr Ser His Pro Met Gln Gly Arg Thr Thr
385                 390                 395                 400
Pro Ser Pro Glu Asp Ser Ser Trp Thr Asp Phe Phe Asn Pro Ile Ser
                405                 410                 415
His Pro Met Gly Arg Gly His Gln Ala Gly Arg Arg Met Asp Met Asp
                420                 425                 430
Ser Ser His Ser Thr Thr Leu Gln Pro Thr Ala Asn Pro Asn Thr Gly
            435                 440                 445
Leu Val Glu Asp Leu Asp Arg Thr Gly Pro Leu Ser Met Thr Thr Gln
        450                 455                 460
Gln Ser Asn Ser Gln Ser Phe Ser Thr Ser His Glu Gly Leu Glu Glu
465                 470                 475                 480
Asp Lys Asp His Pro Thr Thr Ser Thr Leu Thr Ser Ser Asn Arg Asn
                485                 490                 495
Asp Val Thr Gly Gly Arg Arg Asp Pro Asn His Ser Glu Gly Ser Thr
                500                 505                 510
Thr Leu Leu Glu Gly Tyr Thr Ser His Tyr Pro His Thr Lys Glu Ser
            515                 520                 525
Arg Thr Phe Ile Pro Val Thr Ser Ala Lys Thr Gly Ser Phe Gly Val
        530                 535                 540
Thr Ala Val Thr Val Gly Asp Ser Asn Ser Asn Val Asn Arg Ser Leu
545                 550                 555                 560
Ser Gly Asp Gln Asp Thr Phe His Pro Ser Gly Gly Ser His Thr Thr
                565                 570                 575
His Gly Ser Glu Ser Asp Gly His Ser His Gly Ser Gln Glu Gly Gly
                580                 585                 590
Ala Asn Thr Thr Ser Gly Pro Ile Arg Thr Pro Gln Ile Pro Glu Trp
            595                 600                 605
Leu Ile Ile Leu Ala Ser Leu Leu Ala Leu Ala Leu Ile Leu Ala Val
        610                 615                 620
Cys Ile Ala Val Asn Ser Arg Arg Arg Cys Gly Gln Lys Lys Lys Leu
625                 630                 635                 640
Val Ile Asn Ser Gly Asn Gly Ala Val Glu Asp Arg Lys Pro Ser Gly
                645                 650                 655
Leu Asn Gly Glu Ala Ser Lys Ser Gln Glu Met Val His Leu Val Asn
                660                 665                 670
```

```
Lys Glu Ser Ser Glu Thr Pro Asp Gln Phe Met Thr Ala Asp Glu Thr
        675                 680                 685

Arg Asn Leu Gln Asn Val Asp Met Lys Ile Gly Val
        690                 695                 700

<210> SEQ ID NO 3
<211> LENGTH: 2097
<212> TYPE: DNA
<213> ORGANISM: Homo sapiens

<400> SEQUENCE: 3
atggacaagt tttggtggca cgcagcctgg ggactctgcc tcgtgccgct gagcctggcg      60
cagatcgatt tgaatataac ctgccgcttt gcaggtgtat tccacgtgga gaaaaatggt     120
cgctacagca tctctcggac ggaggccgct gacctctgca aggctttcaa tagcaccttg     180
cccacaatgg cccagatgga gaaagctctg agcatcggat ttgagacctg caggtatggg     240
ttcatagaag ggcacgtggt gattccccgg atccacccca actccatctg tgcagcaaac     300
aacacagggg tgtacatcct cacatccaac acctcccagt atgacacata ttgcttcaat     360
gcttcagctc cacctgaaga agattgtaca tcagtcacag acctgcccaa tgcctttgat     420
ggaccaatta ccataactat tgttaaccgt gatggcaccc gctatgtcca aaaggagaa      480 tacagaacga atcctgaaga catctacccc agcaaccta ctgatgatga cgtgagcagc     540
ggctcctcca gtgaaaggag cagcacttca ggaggttaca tcttttacac cttttctact     600
gtacacccca tcccagacga agacagtccc tggatcaccg acagcacaga cagaatccct     660
gctaccagta cgtcttcaaa taccatctca gcaggctggg agccaaatga agaaaatgaa     720
gatgaaagag acagacacct cagttttct ggatcaggca ttgatgatga tgaagatttt     780
atctccagca ccatttcaac cacaccacgg gcttttgacc acacaaaaca gaaccaggac     840
tggacccagt ggaacccaag ccattcaaat ccggaagtgc tacttcagac aaccacaagg     900
atgactgatg tagacagaaa tggcaccact gcttatgaag gaaactggaa cccagaagca     960
caccctcccc tcattcacca tgagcatcat gaggaagaag agaccccaca ttctacaagc    1020
acaatccagg caactcctag tagtacaacg gaagaaacag ctacccagaa ggaacagtgg    1080
tttggcaaca gatggcatga gggatatcgc caaacaccca gaagactcc ccattcgaca    1140 acagggacag ctgcagcctc agctcatacc agccatccaa tgcaaggaag acaacacca    1200 agcccagagg acagttcctg gactgatttc ttcaacccaa tctcacaccc catgggacga    1260
ggtcatcaag caggaagaag gatggatatg gactccagtc atagtacaac gcttcagcct    1320
actgcaaatc caaacacagg tttggtggaa gatttggaca ggacaggacc tctttcaatg    1380
acaacgcagc agagtaattc tcagagcttc tctacatcac atgaaggctt ggaagaagat    1440
aaagaccatc caacaacttc tactctgaca tcaagcaata ggaatgatgt cacaggtgga    1500
agaagagacc caaatcattc tgaaggctca actactttac tggaaggtta tacctctcat    1560
tacccacaca cgaaggaaag caggaccttc atcccagtga cctcagctaa gactgggtcc    1620
tttggagtta ctgcagttac tgttggagat ccaactcta atgtcaatcg ttccttatca    1680
ggagaccaag acacattcca ccccagtggg ggtcccata ccactcatgg atctgaatca    1740 gatgacacact cacatgggag tcaagaaggt ggagcaaaca aacctctgg tcctataagg    1800 acacccaaa ttccagaatg gctgatcatc ttggcatccc tcttggcctt ggctttgatt    1860
cttgcagttt gcattgcagt caacagtcga agaaggtgtg gcagaagaa aaagctagtg    1920
```

```
atcaacagtg gcaatggagc tgtggaggac agaaagccaa gtggactcaa cggagaggcc    1980
agcaagtctc aggaaatggt gcatttggtg aacaaggagt cgtcagaaac tccagaccag    2040
tttatgacag ctgatgagac aaggaacctg cagaatgtgg acatgaagat tggggtg       2097
```

<210> SEQ ID NO 4
<211> LENGTH: 699
<212> TYPE: PRT
<213> ORGANISM: Homo sapiens

<400> SEQUENCE: 4

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Thr
    210                 215                 220

Ser Ser Asn Thr Ile Ser Ala Gly Trp Glu Pro Asn Glu Glu Asn Glu
225                 230                 235                 240

Asp Glu Arg Asp Arg His Leu Ser Phe Ser Gly Ser Gly Ile Asp Asp
                245                 250                 255

Asp Glu Asp Phe Ile Ser Ser Thr Ile Ser Thr Thr Pro Arg Ala Phe
            260                 265                 270

Asp His Thr Lys Gln Asn Gln Asp Trp Thr Gln Trp Asn Pro Ser His
        275                 280                 285

Ser Asn Pro Glu Val Leu Leu Gln Thr Thr Thr Arg Met Thr Asp Val
    290                 295                 300

Asp Arg Asn Gly Thr Thr Ala Tyr Glu Gly Asn Trp Asn Pro Glu Ala
305                 310                 315                 320

His Pro Pro Leu Ile His His Glu His His Glu Glu Glu Glu Thr Pro
                325                 330                 335

His Ser Thr Ser Thr Ile Gln Ala Thr Pro Ser Ser Thr Thr Glu Glu
            340                 345                 350
```

```
Thr Ala Thr Gln Lys Glu Gln Trp Phe Gly Asn Arg Trp His Glu Gly
        355                 360                 365
Tyr Arg Gln Thr Pro Arg Glu Asp Ser His Ser Thr Gly Thr Ala
    370                 375                 380
Ala Ala Ser Ala His Thr Ser His Pro Met Gln Gly Arg Thr Thr Pro
385                 390                 395                 400
Ser Pro Glu Asp Ser Ser Trp Thr Asp Phe Phe Asn Pro Ile Ser His
                405                 410                 415
Pro Met Gly Arg Gly His Gln Ala Gly Arg Arg Met Asp Met Asp Ser
            420                 425                 430
Ser His Ser Thr Thr Leu Gln Pro Thr Ala Asn Pro Asn Thr Gly Leu
        435                 440                 445
Val Glu Asp Leu Asp Arg Thr Gly Pro Leu Ser Met Thr Thr Gln Gln
    450                 455                 460
Ser Asn Ser Gln Ser Phe Ser Thr Ser His Glu Gly Leu Glu Glu Asp
465                 470                 475                 480
Lys Asp His Pro Thr Thr Ser Thr Leu Thr Ser Ser Asn Arg Asn Asp
                485                 490                 495
Val Thr Gly Gly Arg Arg Asp Pro Asn His Ser Glu Gly Ser Thr Thr
            500                 505                 510
Leu Leu Glu Gly Tyr Thr Ser His Tyr Pro His Thr Lys Glu Ser Arg
        515                 520                 525
Thr Phe Ile Pro Val Thr Ser Ala Lys Thr Gly Ser Phe Gly Val Thr
    530                 535                 540
Ala Val Thr Val Gly Asp Ser Asn Ser Asn Val Asn Arg Ser Leu Ser
545                 550                 555                 560
Gly Asp Gln Asp Thr Phe His Pro Ser Gly Gly Ser His Thr Thr His
                565                 570                 575
Gly Ser Glu Ser Asp Gly His Ser His Gly Ser Gln Glu Gly Gly Ala
            580                 585                 590
Asn Thr Thr Ser Gly Pro Ile Arg Thr Pro Gln Ile Pro Glu Trp Leu
        595                 600                 605
Ile Ile Leu Ala Ser Leu Leu Ala Leu Ala Leu Ile Leu Ala Val Cys
    610                 615                 620
Ile Ala Val Asn Ser Arg Arg Arg Cys Gly Gln Lys Lys Lys Leu Val
625                 630                 635                 640
Ile Asn Ser Gly Asn Gly Ala Val Glu Asp Arg Lys Pro Ser Gly Leu
                645                 650                 655
Asn Gly Glu Ala Ser Lys Ser Gln Glu Met Val His Leu Val Asn Lys
            660                 665                 670
Glu Ser Ser Glu Thr Pro Asp Gln Phe Met Thr Ala Asp Glu Thr Arg
        675                 680                 685
Asn Leu Gln Asn Val Asp Met Lys Ile Gly Val
        690                 695

<210> SEQ ID NO 5
<211> LENGTH: 1083
<212> TYPE: DNA
<213> ORGANISM: Homo sapiens

<400> SEQUENCE: 5
atggacaagt tttggtggca cgcagcctgg ggactctgcc tcgtgccgct gagcctggcg      60
cagatcgatt tgaatataac ctgccgcttt gcaggtgtat ccacgtggga gaaaaatggt     120
```

```
cgctacagca tctctcggac ggaggccgct gacctctgca aggctttcaa tagcaccttg      180
cccacaatgg cccagatgga gaaagctctg agcatcggat tgagacctg caggtatggg       240
ttcatagaag ggcacgtggt gattccccgg atccacccca actccatctg tgcagcaaac      300
aacacagggg tgtacatcct cacatccaac acctcccagt atgacacata ttgcttcaat      360
gcttcagctc cacctgaaga agattgtaca tcagtcacag acctgcccaa tgcctttgat      420
ggaccaatta ccataactat tgttaaccgt gatggcaccc gctatgtcca gaaggagaa       480
tacagaacga atcctgaaga catctacccc agcaaccccta ctgatgatga cgtgagcagc    540
ggctcctcca gtgaaaggag cagcacttca ggaggttaca tcttttacac ctttctact      600
gtacaccca tcccagacga agacagtccc tggatcaccg acagcacaga cagaatccct      660
gctaccagag accaagacac attccacccc agtgggggt cccataccac tcatggatct      720
gaatcagatg acactcaca tgggagtcaa gaaggtggag caaacacaac ctctggtcct      780
ataaggacac cccaaattcc agaatggctg atcatcttgg catccctctt ggccttggct      840
ttgattcttg cagtttgcat tgcagtcaac agtcgaagaa ggtgtgggca agaaaaag       900
ctagtgatca acagtggcaa tggagctgtg gaggacagaa agccaagtgg actcaacgga     960
gaggccagca agtctcagga atggtgcat ttggtgaaca aggagtcgtc agaaactcca     1020
gaccagttta tgacagctga tgagacaagg aacctgcaga atgtggacat gaagattggg    1080
gtg                                                                  1083

<210> SEQ ID NO 6
<211> LENGTH: 361
<212> TYPE: PRT
<213> ORGANISM: Homo sapiens

<400> SEQUENCE: 6

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
    130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Glu Arg Ser Ser Thr Ser Gly Gly
            180                 185                 190

Tyr Ile Phe Tyr Thr Phe Ser Thr Val His Pro Ile Pro Asp Glu Asp
```

-continued

```
               195                 200                 205

Ser Pro Trp Ile Thr Asp Ser Thr Asp Arg Ile Pro Ala Thr Thr Asp
    210                 215                 220

Gln Asp Thr Phe His Pro Ser Gly Gly Ser His Thr Thr His Gly Ser
225                 230                 235                 240

Glu Ser Asp Gly His Ser His Gly Ser Gln Glu Gly Gly Ala Asn Thr
                245                 250                 255

Thr Ser Gly Pro Ile Arg Thr Pro Gln Ile Pro Glu Trp Leu Ile Ile
                260                 265                 270

Leu Ala Ser Leu Leu Ala Leu Ala Leu Ile Leu Ala Val Cys Ile Ala
            275                 280                 285

Val Asn Ser Arg Arg Cys Gly Gln Lys Lys Lys Leu Val Ile Asn
    290                 295                 300

Ser Gly Asn Gly Ala Val Glu Asp Arg Lys Pro Ser Gly Leu Asn Gly
305                 310                 315                 320

Glu Ala Ser Lys Ser Gln Glu Met Val His Leu Val Asn Lys Glu Ser
                325                 330                 335

Ser Glu Thr Pro Asp Gln Phe Met Thr Ala Asp Glu Thr Arg Asn Leu
            340                 345                 350

Gln Asn Val Asp Met Lys Ile Gly Val
        355                 360
```

<210> SEQ ID NO 7
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 7
gaattcgccg ccaccatgga caagttttgg tgg                                    33

<210> SEQ ID NO 8
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 8
tctagattac accccaatct tcatg                                             25

<210> SEQ ID NO 9
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 9
tatctagagc cgccaccatg gacaagtttt ggtgg                                  35

<210> SEQ ID NO 10
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 10
tatctagagc cattctggaa tttggggtgt                                        30

```
<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
gatggagaaa gctctgagca tc                                              22

<210> SEQ ID NO 12
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 12
cgtcttcaaa taccatctc                                                  19

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
tttgctccac cttcttgact cc                                              22

<210> SEQ ID NO 14
<211> LENGTH: 30
<212> TYPE: PRT
<213> ORGANISM: Artificial sequence
<220> FEATURE:
<223> OTHER INFORMATION: Synthetic peptide

<400> SEQUENCE: 14

Ser Asn Pro Glu Val Leu Leu Gln Thr Thr Thr Arg Met Thr Ala Asp
1               5                   10                  15

Val Asp Arg Asn Gly Thr Thr Ala Tyr Glu Gly Asn Trp Asn
            20                  25                  30

<210> SEQ ID NO 15
<211> LENGTH: 10
<212> TYPE: PRT
<213> ORGANISM: Artificial sequence
<220> FEATURE:
<223> OTHER INFORMATION: Synthetis peptide

<400> SEQUENCE: 15

Thr Arg Met Thr Ala Asp Val Asp Arg Asn
1               5                   10

<210> SEQ ID NO 16
<211> LENGTH: 12
<212> TYPE: PRT
<213> ORGANISM: Artificial sequence
<220> FEATURE:
<223> OTHER INFORMATION: Synthetis peptide

<400> SEQUENCE: 16

Leu Gln Thr Thr Thr Arg Met Thr Ala Asp Val Asp
1               5                   10
```

-continued

<210> SEQ ID NO 17
<211> LENGTH: 11
<212> TYPE: PRT
<213> ORGANISM: Artificial sequence
<220> FEATURE:
<223> OTHER INFORMATION: Synthetis peptide

<400> SEQUENCE: 17

Met Thr Ala Asp Val Asp Arg Asn Gly Thr Thr
1               5                   10

<210> SEQ ID NO 18
<211> LENGTH: 17
<212> TYPE: PRT
<213> ORGANISM: Artificial sequence
<220> FEATURE:
<223> OTHER INFORMATION: Synthetis peptide

<400> SEQUENCE: 18

Leu Gln Thr Thr Thr Arg Met Thr Ala Asp Val Asp Arg Asn Gly Thr
1               5                   10                  15

Thr

<210> SEQ ID NO 19
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 19
taatacgact cactataggg                                               20

<210> SEQ ID NO 20
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 20
caggaaacag ctatgac                                                  17

<210> SEQ ID NO 21
<211> LENGTH: 366
<212> TYPE: DNA
<213> ORGANISM: Artificial sequence
<220> FEATURE:
<223> OTHER INFORMATION: F8:33 mAb heavy chain

<400> SEQUENCE: 21
gtcggcttag gtgaaactgc agcagtcagg cctggcctgg tggcgccctc acagagcctg    60
tccatcagtt gcactgtctc tgggttttca ttaaccagct atggtgttga ctggttcgc    120 cagcctccag gaaagggtct ggagtggctg ggagtaatat ggggtggtgg aagcacaaat   180
tataattcag ctctcatgtc cagactgagc atcagcaaag acaactccaa gagccaagtt   240
ttcttaaaaa tgaacagtct gcaaactgat gacacagcca tgtactactg tgccaaacat   300
aatagtaact acgggggtt tgcttactgg ggccaaggga ccacggtcac cgtctcctca    360
aaagcc                                                              366

<210> SEQ ID NO 22
<211> LENGTH: 5

```
<212> TYPE: PRT
<213> ORGANISM: Artificial sequence
<220> FEATURE:
<223> OTHER INFORMATION: F8:33 mAb heavy chain CDR1

<400> SEQUENCE: 22

Ser Tyr Gly Val Asp
1               5

<210> SEQ ID NO 23
<211> LENGTH: 16
<212> TYPE: PRT
<213> ORGANISM: Artificial sequence
<220> FEATURE:
<223> OTHER INFORMATION: F8:33 mAb heavy chain CDR2

<400> SEQUENCE: 23

Val Ile Trp Gly Gly Gly Ser Thr Asn Tyr Asn Ser Ala Leu Met Ser
1               5                   10                  15

<210> SEQ ID NO 24
<211> LENGTH: 10
<212> TYPE: PRT
<213> ORGANISM: Artificial sequence
<220> FEATURE:
<223> OTHER INFORMATION: F8:33 mAb heavy chain CDR3

<400> SEQUENCE: 24

His Asn Ser Asn Tyr Gly Gly Phe Ala Tyr
1               5                   10

<210> SEQ ID NO 25
<211> LENGTH: 327
<212> TYPE: DNA
<213> ORGANISM: Artificial sequence
<220> FEATURE:
<223> OTHER INFORMATION: F8:33 mAb light chain

<400> SEQUENCE: 25
cttgacatcc agatgacaca gtctccagca atcatgtctg catctccagg ggagagggtc      60
accatgacct gcagtgccag ctcaagtata cgttacatat attggtacca acagaagcct     120
ggatcctccc ccagactcct gatttatgac acatccaacg tggctcctgg agtccctttt     180
cgcttcagtg gcagtgggtc tgggacttct tattctctca caatcaaccg aatggaggct     240
gaggatgctg ccacttatta ctgccaggag tggagtggtt atccgtacac gttcggaggg     300
gggaccaagc tggagctgaa acggaag                                         327

<210> SEQ ID NO 26
<211> LENGTH: 10
<212> TYPE: PRT
<213> ORGANISM: Artificial sequence
<220> FEATURE:
<223> OTHER INFORMATION: F8:33 mAb light chain CDR1

<400> SEQUENCE: 26

Ser Ala Ser Ser Ser Ile Arg Tyr Ile Tyr
1               5                   10

<210> SEQ ID NO 27
<211> LENGTH: 7
<212> TYPE: PRT
<213> ORGANISM: Artificial sequence
<220> FEATURE:
<223> OTHER INFORMATION: F8:33 mAb light chain  CDR2
```

```
<400> SEQUENCE: 27

Asp Thr Ser Asn Val Ala Pro
1               5

<210> SEQ ID NO 28
<211> LENGTH: 9
<212> TYPE: PRT
<213> ORGANISM: Artificial sequence
<220> FEATURE:
<223> OTHER INFORMATION: F8:33 mAb light chain CDR3

<400> SEQUENCE: 28

Gln Glu Trp Ser Gly Tyr Pro Tyr Thr
1               5

<210> SEQ ID NO 29
<211> LENGTH: 358
<212> TYPE: DNA
<213> ORGANISM: Artificial sequence
<220> FEATURE:
<223> OTHER INFORMATION: F8:33-6-8-10 mAb heavy chain

<400> SEQUENCE: 29
ggtgaaactg caggagtctg gaactgaagt ggtaaagcct ggggcttcag tgaagttgtc      60
ctgcaaggct tctggctaca tcttcacaag ttatgatata gactgggtga ggcagacgcc     120
tgaacaggga cttgagtgga ttggatggat tttcctgga gaggggagta ctgaatacaa     180
tgagaagttc aagggcaggg ccacactgag tgtagacaag tcctccagca cagcctatat     240
ggagctcact aggctgacat ctgaggactc tgctgtctat ttctgtgcta gaggggacaa     300
ctataggcgc tactttgact ggggggccaa aggaccacg gtcaccgtct cctcaaag      358

<210> SEQ ID NO 30
<211> LENGTH: 5
<212> TYPE: PRT
<213> ORGANISM: Artificial sequence
<220> FEATURE:
<223> OTHER INFORMATION: F8:33-6-8-10 mAb heavy chain CDR1

<400> SEQUENCE: 30

Ser Tyr Asp Ile Asp
1               5

<210> SEQ ID NO 31
<211> LENGTH: 17
<212> TYPE: PRT
<213> ORGANISM: Artificial sequence
<220> FEATURE:
<223> OTHER INFORMATION: F8:33-6-8-10 mAb heavy chain CDR2

<400> SEQUENCE: 31

Trp Ile Phe Pro Gly Glu Gly Ser Thr Glu Tyr Asn Glu Lys Phe Lys
1               5                   10                  15

Gly

<210> SEQ ID NO 32
<211> LENGTH: 10
<212> TYPE: PRT
<213> ORGANISM: Artificial sequence
<220> FEATURE:
<223> OTHER INFORMATION: F8:33-6-8-10 mAb heavy chain CDR3

<400> SEQUENCE: 32

Gly Asp Asn Tyr Arg Arg Tyr Phe Asp Leu
```

<210> SEQ ID NO 33
<211> LENGTH: 327
<212> TYPE: DNA
<213> ORGANISM: Artificial sequence
<220> FEATURE:
<223> OTHER INFORMATION: F8:33-6-8-10 mAb light chain

<400> SEQUENCE: 33

```
cttgacatcc agatgacaca gtctccagca atcatgtctg catctccagg ggagagggtc    60
accatgacct gcagtgccag ctcaagtata cgttacatat attggtacca acagaagcct   120
ggatcctccc ccagactcct gatttatgac acatccaacg tggctcctgg agtcccttt    180
cgcttcagtg gcagtgggtc tgggacttct tattctctca caatcaaccg aatggaggct   240
gaggatgctg ccacttatta ctgccaggag tggagtggtt atccgtacac gttcggaggg   300
gggaccaagc tggagctgaa acggaag                                       327
```

<210> SEQ ID NO 34
<211> LENGTH: 10
<212> TYPE: PRT
<213> ORGANISM: Artificial sequence
<220> FEATURE:
<223> OTHER INFORMATION: F8:33-6-8-10 mAb light chain CDR1

<400> SEQUENCE: 34

Ser Ala Ser Ser Ser Ile Arg Tyr Ile Tyr
1               5                   10

<210> SEQ ID NO 35
<211> LENGTH: 7
<212> TYPE: PRT
<213> ORGANISM: Artificial sequence
<220> FEATURE:
<223> OTHER INFORMATION: F8:33-6-8-10 mAb light chain CDR2

<400> SEQUENCE: 35

Asp Thr Ser Asn Val Ala Pro
1               5

<210> SEQ ID NO 36
<211> LENGTH: 9
<212> TYPE: PRT
<213> ORGANISM: Artificial sequence
<220> FEATURE:
<223> OTHER INFORMATION: F8:33-6-8-10 mAb light chain CDR3

<400> SEQUENCE: 36

Gln Glu Trp Ser Gly Tyr Pro Tyr Thr
1               5

<210> SEQ ID NO 37
<211> LENGTH: 360
<212> TYPE: DNA
<213> ORGANISM: Artificial sequence
<220> FEATURE:
<223> OTHER INFORMATION: MF 1-6-11 mAb heavy chain

<400> SEQUENCE: 37

```
gctgtcaagc tgcaggagtc tggacctggc ctggtggcgc cctcacagag cctgtccatc    60
agttgcactg cttctggcta catcttcaca agttatgata tagactgggt gaggcagacg   120
cctgaacagg gacttgagtg gattggatgg atttttcctg agagggggag tactgaatac   180
```

```
aatgagaagt tcaagggcag ggccacactg agtgtagaca agtcctccag cacagcctat    240
atggagctca ctaggctgac atctgaggac tctgctgtct atttctgtgc tagaggggac    300
tactataggc gctactttga cttgtggggc aagggaccac ggtcaccgt ctcctcaaag     360
```

<210> SEQ ID NO 38
<211> LENGTH: 5
<212> TYPE: PRT
<213> ORGANISM: Artificial sequence
<220> FEATURE:
<223> OTHER INFORMATION: MF 1-6-11 mAb heavy chain CDR1

<400> SEQUENCE: 38

Ser Tyr Asp Ile Asp
1               5

<210> SEQ ID NO 39
<211> LENGTH: 17
<212> TYPE: PRT
<213> ORGANISM: Artificial sequence
<220> FEATURE:
<223> OTHER INFORMATION: MF 1-6-11 mAb heavy chain CDR2

<400> SEQUENCE: 39

Trp Ile Phe Pro Gly Glu Gly Ser Thr Glu Tyr Asn Glu Lys Phe Lys
1               5                   10                  15

Gly

<210> SEQ ID NO 40
<211> LENGTH: 10
<212> TYPE: PRT
<213> ORGANISM: Artificial sequence
<220> FEATURE:
<223> OTHER INFORMATION: MF 1-6-11 mAb heavy chain CDR3

<400> SEQUENCE: 40

Gly Asp Tyr Tyr Arg Arg Tyr Phe Asp Leu
1               5                   10

<210> SEQ ID NO 41
<211> LENGTH: 327
<212> TYPE: DNA
<213> ORGANISM: Artificial sequence
<220> FEATURE:
<223> OTHER INFORMATION: MF 1-16-11 mAb light chain

<400> SEQUENCE: 41

```
cttgacatcc agatgacaca gtctccagca atcatgtctg catctccagg ggagagggtc    60
accatgacct gcagtgccag ctcaagtata cgttacatat attggtacca acagaagcct    120
ggatcctccc ccagactcct gatttatgac acatccaacg tggctcctgg agtccctttt    180
cgcttcagtg gcagtgggtc tgggacttct tattctctca caatcaaccg aatggaggct    240
gaggatgctg ccacttatta ctgccaggag tggagtggtt atccgtacac gttcggaggg    300
gggaccaagc tggagctgaa acggaag                                        327
```

<210> SEQ ID NO 42
<211> LENGTH: 10
<212> TYPE: PRT
<213> ORGANISM: Artificial sequence
<220> FEATURE:
<223> OTHER INFORMATION: MF 1-16-11 mAb light chain CDR1

<400> SEQUENCE: 42

```
Ser Ala Ser Ser Ser Ile Arg Tyr Ile Tyr
1               5                   10
```

<210> SEQ ID NO 43
<211> LENGTH: 7
<212> TYPE: PRT
<213> ORGANISM: Artificial sequence
<220> FEATURE:
<223> OTHER INFORMATION: MF 1-16-11 mAb light chain CDR2

<400> SEQUENCE: 43

```
Asp Thr Ser Asn Val Ala Pro
1               5
```

<210> SEQ ID NO 44
<211> LENGTH: 9
<212> TYPE: PRT
<213> ORGANISM: Artificial sequence
<220> FEATURE:
<223> OTHER INFORMATION: MF 1-16-11 mAb light chain CDR3

<400> SEQUENCE: 44

```
Gln Glu Trp Ser Gly Tyr Pro Tyr Thr
1               5
```

What is claimed is:

1. An isolated antibody comprising an antigen recognition domain capable of specifically binding a CD44 polypeptide as set forth in SEQ ID NO: 2 and incapable of binding a CD44 polypeptide selected from the group consisting of: SEQ ID NOs: 4 and 6.

2. The antibody of claim 1, wherein the antibody is an antibody or an antibody fragment.

3. The antibody of claim 2, wherein said antibody or antibody fragment is humanized.

4. The antibody of claim 2, wherein said antibody or said antibody fragment is selected from the group consisting of a Fab fragment, an Fv fragment, a single chain antibody and a single domain antibody.

5. The antibody of claim 2, wherein said antibody is produced by a cell hybridoma having the depository Accession No. CNCM I-3015 (F8:33 hybridoma) or CNCM I-3016 (F8:33-6-8-10 hybridoma).

6. The antibody of claim 1, comprises a light chain variable region comprising amino acid sequences of set forth by set forth by SEQ ID NO:22 (CDR1), SEQ ID NO:23 (CDR2) and SEQ ID NO:24 (CDR3) and a heavy chain variable region comprising amino acid sequences set forth by SEQ ID NO:26 (CDR1), SEQ ID NO:27 (CDR2) and SEQ ID NO: 28 (CDR3).

7. A pharmaceutical composition comprising as an active ingredient the antibody of claim 1 and a pharmaceutically effective carrier or diluent.

8. A kit for diagnosing a rheumatoid disease in a subject, the kit comprising the antibody of claim 1 and at least one reagent for detecting complexes including the antibody.

9. The kit of claim 8, wherein detecting said complexes is effected by an assay selected from the group consisting of immunohistochemistry, ELISA, RIA, Western blot analysis, FACS analysis, an immunofluorescence assay, and a light emission immunoassay.

10. The kit of claim 8, wherein the rheumatoid disease is a rheumatoid autoimmune disease.

11. The kit of claim 8, wherein the rheumatoid disease is selected from the group consisting of rheumatoid arthritis and psoriatic arthritis.

* * * * *